United States Patent
Szymanski et al.

(10) Patent No.: US 10,620,221 B2
(45) Date of Patent: Apr. 14, 2020

(54) DEVICES AND ASSAYS FOR DIAGNOSIS OF SINUSITIS

(71) Applicant: Entvantage Diagnostics, Inc., Austin, TX (US)

(72) Inventors: Aaron Szymanski, Thomaston, CT (US); David Seebauer, Southington, CT (US); Mohan Rajasekaran, Bristol, CT (US); John Wysmuller, Wethersfield, CT (US); Michael Mennone, Litchfield, CT (US); Rishwa Baxi, Southington, CT (US); Cheng-Ling Yang, Middletown, CT (US); Scott Johnstone, Pleasant Valley, CT (US); Joseph Skraba, Austin, TX (US); Zachary Hawkins, Austin, TX (US); Oriana E. Hawkins, Fort Worth, TX (US); Soumya Mohana-Sundaram, Fort Worth, TX (US)

(73) Assignee: Entvantage Diagnostics, Inc., Austin, TX (US)

(*) Notice: Subject to any disclaimer, the term of this patent is extended or adjusted under 35 U.S.C. 154(b) by 306 days.

(21) Appl. No.: 15/470,849

(22) Filed: Mar. 27, 2017

(65) Prior Publication Data
US 2017/0199206 A1 Jul. 13, 2017
US 2018/0172706 A9 Jun. 21, 2018

Related U.S. Application Data

(63) Continuation of application No. 15/084,934, filed on Mar. 30, 2016, now Pat. No. 9,606,118.
(Continued)

(51) Int. Cl.
*A61B 5/00* (2006.01)
*G01N 33/68* (2006.01)
(Continued)

(52) U.S. Cl.
CPC ..... *G01N 33/6893* (2013.01); *A61B 5/14507* (2013.01); *A61B 5/6847* (2013.01);
(Continued)

(58) Field of Classification Search
CPC ........ G01N 33/53; G01N 1/405; A61B 5/097; A61B 5/0816; A61B 10/0038;
(Continued)

(56) References Cited

U.S. PATENT DOCUMENTS

| 1,841,607 A | 1/1932 | Kollsman |
| 2,999,389 A | 9/1961 | Granqvist |

(Continued)

FOREIGN PATENT DOCUMENTS

| JP | 62148859 A | 7/1987 |
| WO | WO2004/059280 A2 | 7/2004 |

(Continued)

OTHER PUBLICATIONS

Altschul et al., Basic local alignment search tool; J. Mol. Biol., 215(3): pp. 403-410, Oct. 1990.
(Continued)

*Primary Examiner* — May A Abouelela
(74) *Attorney, Agent, or Firm* — Shay Glenn LLP

(57) ABSTRACT

Methods and kits for sampling mucous from within a sinus to determine if a single sample includes one or more bacterial types indicating bacterial sinusitis.

22 Claims, 38 Drawing Sheets

Related U.S. Application Data

(60) Provisional application No. 62/209,712, filed on Aug. 25, 2015, provisional application No. 62/140,405, filed on Mar. 30, 2015.

(51) Int. Cl.
| | |
|---|---|
| *C12Q 1/04* | (2006.01) |
| *G01N 33/558* | (2006.01) |
| *G01N 33/569* | (2006.01) |
| *A61B 5/145* | (2006.01) |
| *A61B 10/00* | (2006.01) |

(52) U.S. Cl.
CPC ............ *A61B 10/0045* (2013.01); *C12Q 1/04* (2013.01); *G01N 33/558* (2013.01); *G01N 33/56911* (2013.01); *G01N 33/56944* (2013.01); *A61B 2010/0006* (2013.01); *G01N 2333/212* (2013.01); *G01N 2333/285* (2013.01); *G01N 2333/3156* (2013.01); *G01N 2800/14* (2013.01)

(58) Field of Classification Search
CPC ............ A61B 10/0045; A61B 10/0096; A61B 10/0275; A61B 5/6819; A61B 5/682
USPC ....... 600/106, 184, 300, 350, 570, 572, 580, 600/581, 582; 604/2, 540; 606/196
See application file for complete search history.

(56) References Cited

U.S. PATENT DOCUMENTS

| | | | |
|---|---|---|---|
| 3,160,018 A | 12/1964 | Johnston | |
| 3,218,871 A | 11/1965 | Dressler et al. | |
| 3,910,122 A | 10/1975 | Evans et al. | |
| 3,965,753 A | 6/1976 | Browning | |
| 4,157,280 A | 6/1979 | Halbert et al. | |
| 4,393,707 A | 7/1983 | Ferrar | |
| 4,941,353 A | 7/1990 | Fukatsu et al. | |
| 5,012,676 A | 5/1991 | Takahashi et al. | |
| 5,415,994 A | 5/1995 | Imrich et al. | |
| 5,656,448 A | 8/1997 | Kang et al. | |
| 5,664,567 A * | 9/1997 | Linder | A61M 27/002 128/207.18 |
| 5,763,262 A | 6/1998 | Wong et al. | |
| 5,910,421 A | 6/1999 | Small et al. | |
| 6,043,032 A | 3/2000 | Yamagishi | |
| 6,127,775 A | 10/2000 | Bergen | |
| 6,306,084 B1 | 10/2001 | Pinczower | |
| 6,514,216 B2 * | 2/2003 | Inoue | A61B 10/0045 600/573 |
| 6,626,172 B1 | 9/2003 | Karow et al. | |
| 7,700,372 B2 | 4/2010 | Nylese | |
| 7,811,589 B2 | 10/2010 | Murphy et al. | |
| 8,202,487 B2 | 6/2012 | Lee | |
| 8,652,067 B2 * | 2/2014 | Lonky | A61B 10/0291 600/569 |
| 9,086,408 B2 | 7/2015 | Egan et al. | |
| 9,568,472 B2 | 2/2017 | Das et al. | |
| 9,606,118 B2 | 3/2017 | Skraba et al. | |
| 2002/0032410 A1 * | 3/2002 | Inoue | A61B 10/0045 604/164.01 |
| 2002/0164354 A1 | 11/2002 | Barenkamp | |
| 2002/0176087 A1 | 11/2002 | Numal | |
| 2003/0162186 A1 | 8/2003 | Bejanin et al. | |
| 2004/0175695 A1 | 9/2004 | Debad et al. | |
| 2004/0211257 A1 | 10/2004 | Geen | |
| 2005/0240147 A1 * | 10/2005 | Makower | A61B 17/24 604/96.01 |
| 2005/0272106 A1 | 12/2005 | Moore et al. | |
| 2006/0210605 A1 | 9/2006 | Chang et al. | |
| 2006/0257941 A1 | 11/2006 | McDevitt et al. | |
| 2007/0141564 A1 | 6/2007 | Aberl et al. | |
| 2008/0008992 A1 | 1/2008 | Ohshiro et al. | |
| 2008/0097295 A1 | 4/2008 | Makower et al. | |
| 2008/0097463 A1 | 4/2008 | House | |
| 2008/0154250 A1 | 6/2008 | Makower et al. | |
| 2008/0254997 A1 | 10/2008 | Oku et al. | |
| 2009/0181485 A1 | 7/2009 | Baik et al. | |
| 2009/0211345 A1 | 8/2009 | Nahm et al. | |
| 2009/0280480 A1 | 11/2009 | Lindquist et al. | |
| 2010/0099115 A1 | 4/2010 | Mach et al. | |
| 2011/0004057 A1 | 1/2011 | Goldfarb et al. | |
| 2011/0151432 A1 | 6/2011 | Zappia et al. | |
| 2011/0166166 A1 | 7/2011 | Henkin | |
| 2011/0224652 A1 * | 9/2011 | Drontle | A61B 17/24 604/540 |
| 2012/0053404 A1 * | 3/2012 | Schreck | A61B 17/24 600/104 |
| 2012/0276145 A1 | 11/2012 | Webster et al. | |
| 2013/0116596 A1 * | 5/2013 | Birnboim | A61B 10/0045 600/570 |
| 2013/0231588 A1 * | 9/2013 | Fukuhara | A61B 10/0275 600/572 |
| 2014/0336488 A1 | 11/2014 | Das | |
| 2014/0336693 A1 * | 11/2014 | Goldfarb | A61M 29/02 606/196 |
| 2015/0057517 A1 * | 2/2015 | Pease | A61B 10/02 600/350 |
| 2017/0184589 A1 | 6/2017 | Das et al. | |
| 2018/0217145 A1 | 8/2018 | Skraba et al. | |
| 2019/0004046 A1 | 1/2019 | Das et al. | |

FOREIGN PATENT DOCUMENTS

| | | |
|---|---|---|
| WO | WO2005/063802 A2 | 7/2005 |
| WO | WO2006/033662 A2 | 3/2006 |
| WO | WO2007/106552 A2 | 9/2007 |
| WO | WO2010/092176 A2 | 8/2010 |
| WO | WO2011/096515 A1 | 8/2011 |
| WO | WO2014/072977 A1 | 5/2014 |
| WO | WO2016/110854 A1 | 7/2016 |

OTHER PUBLICATIONS

American Academy of Pediatrics; Diagnosis and Management of Acute Otitis Media (Clinical Practice Guideline); Pediatrics; 113(5); pp. 1451-1456; Apr. 2004.

Bakaletz et al.; Frequency of fimbriation of nontypable haemophilus influenzae and its ability to adhere to chinchilla and human respiratory epithelium; Infection and Immunity, 56(2): pp. 331-335, Feb. 1988.

Becton, Dickinson and Company; BD Veritor System (product information); retrieved from: www.bd.com/ds/veritorsystem/poctesting. asp; pgs.; retrieved/printed: May 10, 2016.

Bell et al.; Diversity of the P2 protein among nontypeable haemophilus influenzae isolates; Infection and Immunity; 62(6); pp. 2639-2643; Jun. 1, 1994.

Devereux et al., A comprehensive set of sequence analysis programs for the VAX; Nucl. Acid. Res., 12(pt1); pp. 387-395; Jan. 1984.

Engels et al.; Meta-analysis of diagnostic tests for acute sinusitis; J. Clin. Epidemiol.; 53(8); pp. 852-862; Aug. 2000.

Gallaher et al.; Identification of biofilm proteins in non-typeable haemophilus influenzae; BMC Microbiology; 6; pp. 65 (9 pgs); Jul. 2006.

Kohler et al.; Continuous cultures of fused cells secreting antibody of predefined specificity; Nature 256(5517): pp. 495-497; Aug. 1975.

Krasan et al.; Adhesin expression in matched nasopharyngeal and middle ear isolates of nontypeable haemophilus influenzae from children with acute otitis media; Infection and imunity; 67(1); pp. 449-454; Jan. 1999.

Novotny et al.; Transcutaneous immunization as preventative and therapeutic regimens to protect against experimental otitis media due to nontypeable Haemophilus influenzae; Mucosal Immunology; 4(4); pp. 456-467; Feb. 2011.

Nyquist et al.; Antibiotic prescribing for children with colds, upper respiratory tract infections, and bronchitis; JAMA; 279(11); pp. 875-877; (html version; 11 pgs) Mar. 1988.

(56) References Cited

OTHER PUBLICATIONS

Oliveira et al.; Computer-based analysis of Haemophilus parasuis protein fingerprints; Can J Vet Res; 68(1); pp. 71-75; Jan. 2004.
Perkins et al.; Probability-based protein identification by searching sequence databases using mass spectrometry data; Electrophoresis; 20(18); pp. 3551-3567; Dec. 1999.
Qu et al.; Proteomic expression profiling of haemophilus influenzae grown in pooled human sputum from adults with chronic obstructive pulmonary disease reveal antioxidant and stress responses; BMC Microbiology; 10; pp. 162 (12 pgs); Jun. 2010.
Quidel; Sofia (product information); retrieved from: www.quidel.com/immunoassays/sofia-tests-kits; 2 pgs.; retrieved/printed: May 10, 2016.
Reddy et al.; Binding between outer membrane proteins of nontypeable Haemophilus influenzae and human nasopharyngeal mucin; Infection and Ummunity; 64(4); pp. 1477-1479; Apr. 1996.
Subinoy et al.; Improving patient care via development of a protein-based diagnostic test for microbe-specific detection of chronic rhinosinusitis; (Author Manuscript; 20 pgs.); Laryngoscope; 124(3); pp. 608-615; Mar. 2014.
Villaseñor-Sierra et al.; Outer membrane protein profiles of paired nasopharyngeal and middle ear isolates of nontypable haemophilus influenzae from Mexican children with acute otitis media; Clinical Infectious Diseases; 28(2); pp. 267-273; Feb. 1999.
Bulter; Solid supports in enzyme-linked immunosorbent assay and other solid-phase immunoassays; Methods; 22(1); pp. 4-23; Sep. 1, 2000.
Duim et al; Molecular variation in the major outer membrane protein P5 gene of nonencapsulated haemophilus influenzae during chronic infections; Infection and Immunity; 65(4); pp. 1351-1356; Apr. 1, 1997.
Esmaily et al; Efficacy of immunization with outer membrane proteins for induction of pulmonary clearance of nontypeable heamophilus influenzae in rat respiratory model; Iran J. Allergy, Asthma Immunol.; 5(2); pp. 57-61; Jun. 2006.
Ishida et al.; Effects of macrolides on antigen presentation and cytokine production by dendritic celss and T lymphocytes; Int. J. Pediatr. Otorhinolaryngol.; 71(2); pp. 297-305; (Manuscript copy, 30 pages); Feb. 28, 2007.
Ogino; Bacteriological findings in chronic sinusitis; Otolaryngology; 55(5); pp. 347-353; (English Abstract Only); May 20, 1983.
Cambridge Academic Content Dictionary; Affix (definition); 6 pages; retrived from the internet (https://dictionary.cambridge.org/us/dictionary/english/affix) on Mar. 8, 2018.

\* cited by examiner

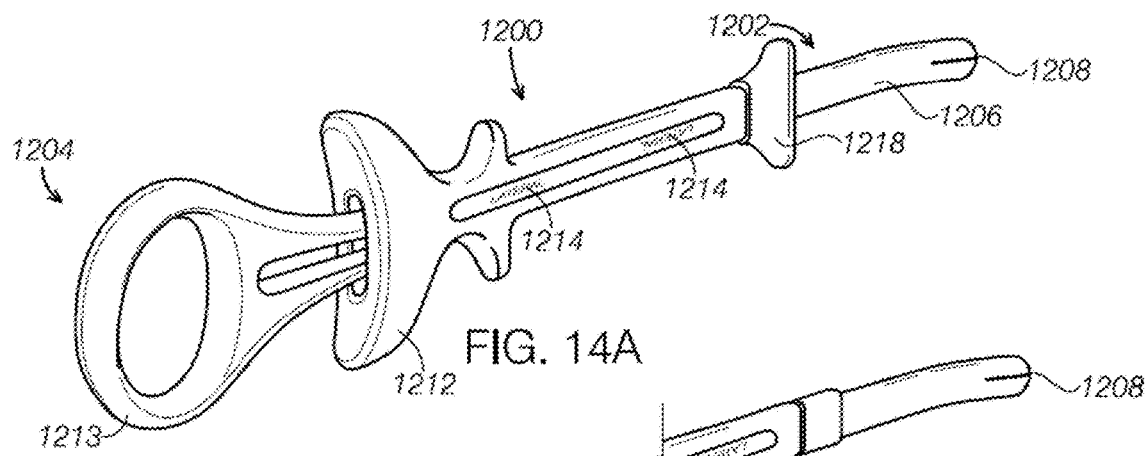
FIG. 14A
FIG. 14B
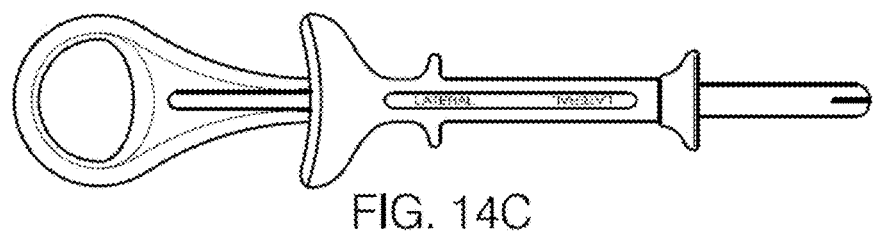
FIG. 14C
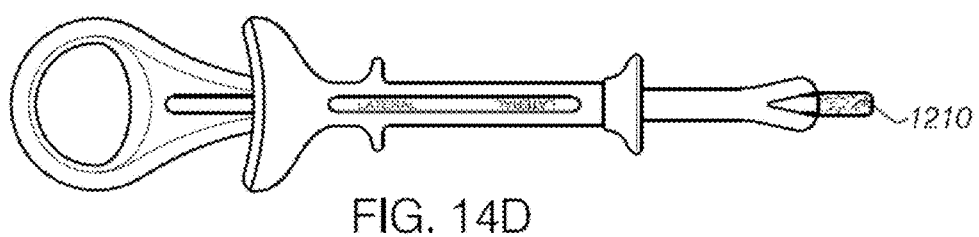
FIG. 14D
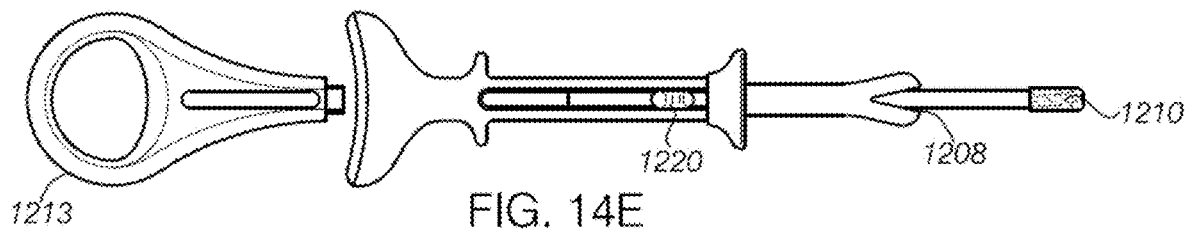
FIG. 14E

| Primary Active Component | M.cat | S.pneumo | H.flu | Comments |
|---|---|---|---|---|
| B-PER reagent | - | - | - | Cell wall disruption |
| 0.1% Triton X-100 without lysozyme | - | - | - | Detergent lysis |
| 0.1% Triton X-100 with lysozyme | + | - | - | Lysozyme disrupting the cell wall |
| RIPA buffer | - | - | - | Ionic and non-ionic detergent disrupting the cell wall |
| 0.1% Tween 20 | - | - | - | Non-ionic detergent disruption |
| 0.1% IGEPAL | - | - | - | Non-ionic detergent disruption |
| 0.1% Tergitol | - | - | - | Non-ionic detergent disruption |
| 0.1% Brij 35 | - | - | - | Non-ionic detergent disruption |
| 1% Sarkosyl | - | - | + | Anionic detergent disruption |
| 7% sucrose with 1.3% Sodium Lauroyl Sarcosinate | + | + | + | Osmotic and anionic detergent disrupting cell wall |
| **3.5% sucrose with 0.65% Sodium Lauroyl Sarcosinate | + | + | + | Osmotic and anionic detergent disrupting cell wall |
| 1.75% Sucrose with 0.325% Sodium Lauroyl Sarcosinate | + | + | + | Osmotic and anionic detergent disrupting cell wall |

FIG. 27

| ENTV lysis Buffer #1 |
|---|
| 25mM Tris |
| 15.5 mM EDTA |
| 500 µM PMSF |
| 100 mM Sucrose |
| 22mM Sodium Lauroyl Sarcosinate |
| pH 8.0 |

FIG. 28

| ENTV lysis Buffer #2 |
|---|
| 137 mM NaCl |
| 2.7 mM KCl |
| 12 mM Na$_2$HPO$_4$ |
| 15.5 mM EDTA |
| 500 µM PMSF |
| 100 mM Sucrose |
| 22mM Sodium Lauroyl Sarcosinate |
| pH 7.4 |

| ENTV Dilution Buffer #1 |
|---|
| 100mM Tris |
| 0.1% Triton X-100 |
| 0.1% Tween 20 |
| pH 9.4 |

FIG. 29

| ENTV Dilution Buffer #2 |
|---|
| 137 mM NaCl |
| 2.7 mM KCl |
| 12 mM Na$_2$HPO$_4$ |
| 0.1% Triton X-100 |
| 0.1% Tween 20 |
| pH 7.4 |

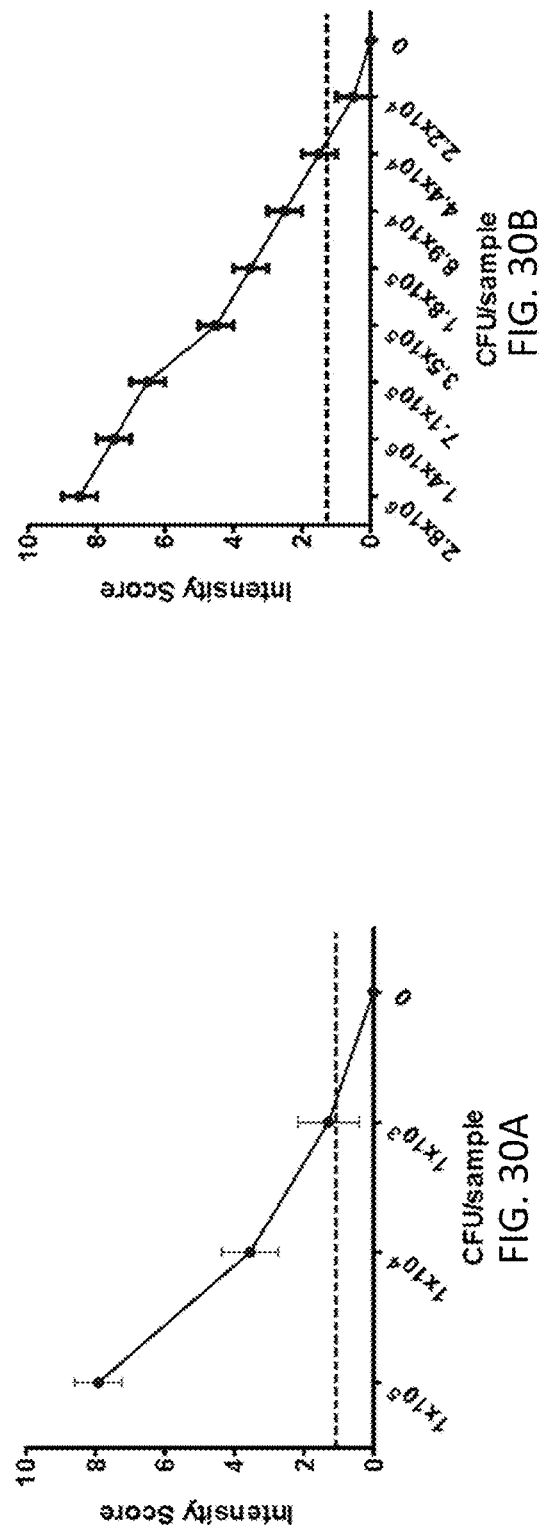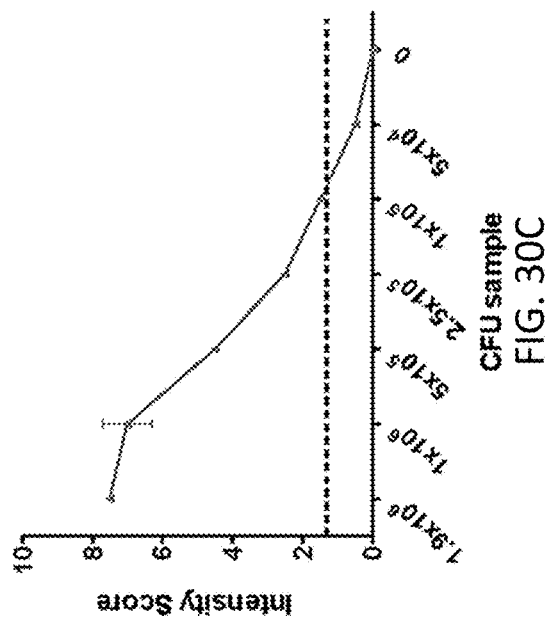
FIG. 30A Detection of S. pneumoniae PsaA
FIG. 30B Detection of M. catarrhalis
FIG. 30C Detection of H. influenzae

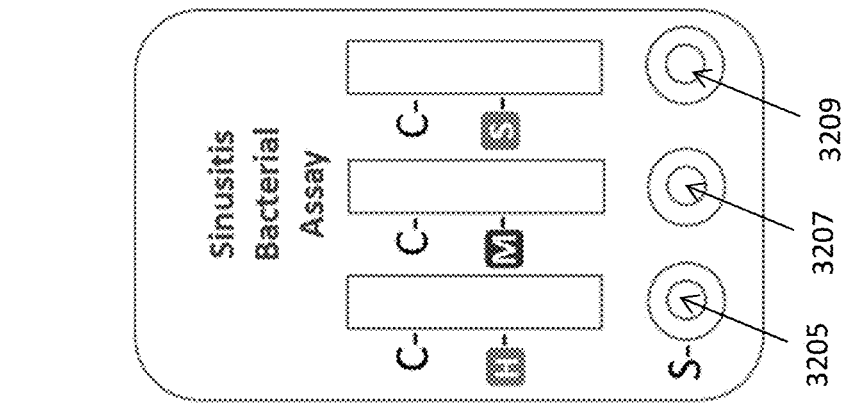
FIG. 32
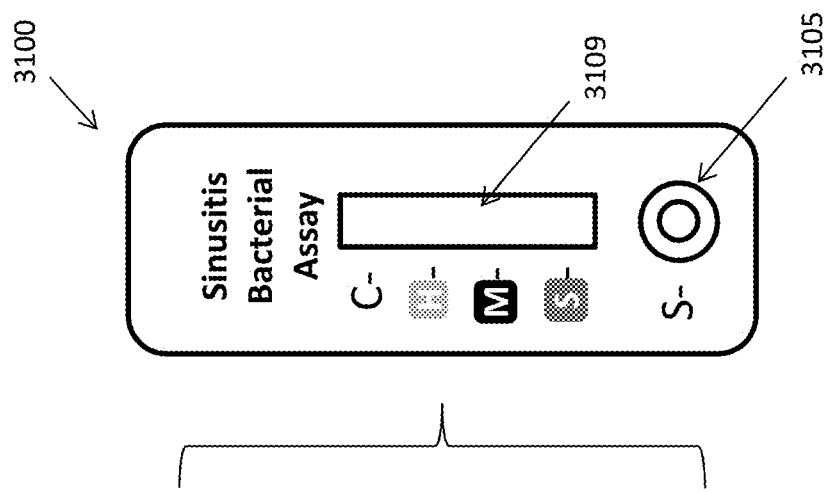
FIG. 31
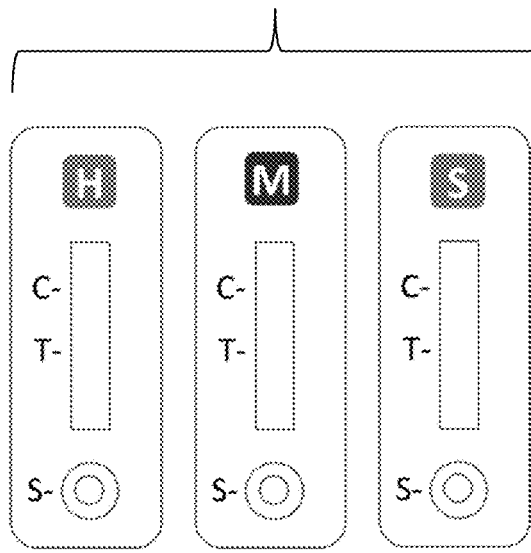

DEVICES AND ASSAYS FOR DIAGNOSIS OF SINUSITIS

CROSS REFERENCE TO RELATED APPLICATIONS

This patent application is a continuation of U.S. patent application Ser. No. 15/084,934, titled "DEVICES AND ASSAYS FOR DIAGNOSIS OF SINUSITIS," filed on Mar. 30, 2016, now U.S. Pat. No. 9,606,118, which claims priority to U.S. Provisional Patent Application No. 62/140,405, titled "DEVICES AND METHODS FOR OBTAINING MUCOUS SAMPLES," filed on Mar. 30, 2015 and U.S. Provisional Patent Application No. 62/209,712, titled "DEVICES AND ASSAYS FOR DIAGNOSIS OF SINUSITIS," filed on Aug. 25, 2015, each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The present application relates to methods and devices for the determination of the presence of one or more pathogens associated with bacterial sinusitis from a collected mucus sample, and preferably the detection of three or more of the pathogens associated with over 90% of bacterial sinusitis.

BACKGROUND

Sinusitis, defined as inflammation of the sinus tissues, usually as a complication to viral infections from the common cold. Although there are over 1 billion common colds in the U.S., a small percentage of them lead to sinusitis. In fact, 29 million people were diagnosed with sinusitis in 2011 in the US. Often antibiotics are ordered as a treatment for sinusitis and it is the 5th leading indication for the antibiotic prescriptions annually. Western EU markets are estimated to be over 43 million patients annually. The majority of these patients are initially seen by primary care physicians and then referred out to otolaryngologists, also known as ENT's if their symptoms do not resolve. Complicated cases of sinusitis eventually lead to surgery and there are 1.5 million patients in the U.S. each year that are candidates for surgical procedures, in which currently 500 k patients elect to undergo some type of surgical procedure. The direct costs association with managing sinusitis amount to over $6 billion annually, with another $3 billion associated with indirect costs associated with sinusitis management.

The initial diagnosis of sinusitis remains a challenge for physicians. A patient presenting at a physician's office with a symptom complex of fever, headache and fatigue, also present in many different types of systemic diseases, could warrant a diagnosis of sinusitis. As a result, many patients with non-sinus related diseases such as migraine disorders, chronic fatigue, and chronic systemic disorders are misdiagnosed as sinusitis. An additional objective laboratory diagnostic testing would guide physicians as to the etiology of these common symptoms of viral upper respiratory tract infections, acute bacterial sinusitis and chronic sinusitis and lead to reduction of unnecessary antibiotic and steroid prescriptions provided to patients.

Currently doctors typically decide on a treatment regime without a definitive test to determine if the patient has viral sinusitis, bacterial sinusitis, upper respiratory infection, chronic fatigue, or migraines, because it is difficult to diagnose the cause of sinusitis as either viral or bacterial etiology. Treatment often involves antibiotics, which are only effective for a small amount of these conditions. The majority of sinusitis cases are viral, with some estimates that about 90% of sinusitis cases are viral. Majority of all patients receive an antibiotic that they do not need, can make their condition worse, and can lead to antibiotic resistance. Improved methods of diagnosing sinusitis are needed. In particular, what is needed is a definitive, rapid test for the cause of sinusitis, which could save the physician time and provide timely information that will lead to fewer antibiotics being prescribed.

There are many advantages to determining the etiology of sinusitis (e.g., as viral, bacterial, etc.), including the reduction in health care costs, decreases in antibiotic use and concomitant bacterial drug resistance, and improvements in the level of care for patients. Described herein are bacterial sinusitis diagnostic apparatuses (e.g., devices, systems, kits, etc.) and methods that may address many of the needs described herein. For example, the sampling, testing, and treatment apparatuses and methods described herein may allow for rapid and definitive diagnosis of bacterial sinusitis, permitting targeted treatment with optimal antibiotics based on the specific diagnosis. Such targeted treatment may avoid unnecessary antibiotic treatments for patients not suffering from bacterial sinusitis. A rapid diagnosis may also result in improved treatment for patients that test negative for bacterial sinusitis by instead treating the patient based on a negative test for bacterial sinusitis.

SUMMARY OF THE DISCLOSURE

Described herein are apparatuses (e.g., systems, kits, assays, including lateral flow assay kits) and methods which may allow determination of the presence of one or more of the three pathogens associated with over 90% of bacterial sinusitis from a collected mucus sample. Specifically, these methods and apparatuses may determine, as part of a single rapid assay, the presence of one or more of: *Haemophilus influenzae*, *Moraxella catarrhalis* and *Streptococcus pneumoniae*. In particular, described herein are sinus collection devices for collection of mucus samples from patient sinuses; these collection devices may be included as part of the assays described herein.

The sinus collection devices (sampling devices) described herein are intended for use during a routine office visit to a physician. These devices may accurately and quickly (with a minimum of discomfort) allow the acquisition of a mucus sample from the middle meatus region of the sinus (while avoiding miss-targeting of the region and cross-contamination). A collected mucus sample may then be analyzed using any of the lateral flow assays described herein. If the test is positive for any of the three bacterial pathogens, the patient has bacterial sinusitis and may be prescribed an appropriate antibiotic and/or steroid regimen to address the pathogenic bacteria. If the test is negative, the patient may be treated for viral sinusitis and antibiotics may not be administered. Examples of the sampling devices and assays (e.g., lateral flow assays) are described herein. Although the majority of these examples describe apparatuses, including collection devices, that are adapted for use in the nasal cavity, any of these apparatuses and methods may be adapted for use in other regions. For example, a variation of the sampling device and/or the assay may be adapted for use in collecting mucus samples from within the sinus during sinus surgery procedures, from an ear (e.g., in the case of otitis media, which is usually caused by the same three pathogens as is bacterial sinusitis) or elsewhere.

As will be described in greater detail below, these assays may be configured as lateral flow assays that include a single lysis solution (e.g., lysis buffer solution) that is appropriate for use with all three types of bacteria (e.g., *H. influenzae, M. catarrhalis* and *S. pneumoniae*) in order to expose the antigens specific to each one for detection. Any of the assays described herein may be adapted for use with the lysis buffer, and may include multiple (e.g., three) pairs, or defined pools, of antigen binding agents that bind antigens (e.g., surface proteins) specific to each type of bacteria (e.g., *H. flu, M. cat, S. pneumo*). The antigen binding agents ("agents") may be monoclonal or polyclonal antibodies, or antibody fragments (e.g., FAB fragments, etc.) or molecules including all or a portion of these. Pairs of such agents may bind to different portions of the same antigen. An agent specific to each type of bacteria (e.g., *H. flu, M. cat, S. pneumo*) may be bound to a solid phase substrate (e.g., membrane, particle, etc.) and spatially arranged in the assay and provide specific identification of *H. influenzae, M. catarrhalis* and *S. pneumoniae* by visual detection of binding, including by binding the antigen to the tethered substrate and to a labeled agent. The pairs or pools of antibodies may be chosen to have low cross-reactivity, while allowing comparable detection of *H. influenzae, M. catarrhalis* and *S. pneumoniae.*

The antigen binding agent (or "agent" and may also be referred to herein as an indicator) may be chosen so that they are selective for the organism of interest, binds cognate antigen specifically, have minimal cross-reactivity to common contaminating organisms and minimal cross-reactivity with commensal organisms. These antigen binding agents may also have a high affinity to the target pathogen antigen, rapid association kinetics, slow dissociation kinetics, and be sensitive to low numbers of the pathogen. Finally these antigen binding agents may be compatible with lateral flow, and compatible with a conjugate. As mentioned above, in particular the antigen binding agents may also be compatible for use with a common lysing solution for all three pathogens.

As will be described in greater detail herein, finding a common lysing solution that may work with multiple types of pathogens, and particularly *H. flu, M. cat* and *S. pneumo*, was surprisingly difficult, as many commonly used lytic agents (detergents, enzymes, etc.) did not work with all three, resulting in incomplete lysis (clogging of the lateral flow system), lysis that was too slow (e.g., took longer than 15 minutes), or disrupted the surface proteins, including the antigens specific to each cell type.

*Haemophilus influenzae (H. influenzae)* may be detected using a pair or pool of antibodies that are specific to one or more antigen binding agents that are relatively specific or characteristic of *H. influenzae*. For example, the indicator for *H. influenzae* may bind with specificity to the OMP-P2 and/or OMP-P5 antigen binding site for the pathogen. As described herein, numerous primary candidate antibodies have been evaluated, and screened for cross reactivity between numerous (e.g., 30) commensal bacterial strains to assure minimal cross reactivity with the normal flora occurring in the healthy sinus. Other examples of antigen binding agents include antibodies that may be used are discussed in US20140314876, herein incorporated by reference in its entirety.

Similarly, *Moraxella catarrhalis (M. catarrhalis)* may be detected using a pair or pool of antigen binding agents that are specific to a marker for *M. catarrhalis* (see, e.g., U.S. Pat. No. 7,811,589) such as Protein C and Protein D outer member proteins.

One or more antigen binding agents specific for *Streptococcus pneumoniae (S. pneumonia)* may also be directed to *S. pneumoniae* markers such as the PsaA antigen.

Specifically described herein are assay kits for concurrently detecting *H. influenzae, M. catarrhalis* and *S. pneumoniae* from a mucosal samples. An assay kit may include: a lysis buffer to lyse cells within the sample and form a single sample solution, wherein the lysis buffer comprises between 0.01% and 5% (w/w) of the anionic surfactant and between 0.1% and 15% (w/w) of the osmotic agent; a cartridge containing one or more solid phase substrates holding a first agent that that binds specifically to a first antigen specific to *H. influenzae* but not *M. catarrhalis* or *S. pneumoniae*, a second agent that binds specifically to a second antigen specific to *M. catarrhalis* but not *H. influenzae* or *S. pneumoniae*, and a third agent that binds specifically to a third antigen specific to *S. pneumoniae* but not *M. catarrhalis* or *H. influenzae*, wherein the first, second and third agents are bound to specific regions of the one or more solid phase substrates in the cartridge; one or more conjugation regions within the cartridge, the one or more conjugation regions in fluid communication with the one or more solid phase substrates and comprising a fourth agent that is labeled and that binds specifically to the first antigen, a fifth agent that is labeled and that binds specifically to the second antigen, and a sixth agent that is labeled and that bind specifically to the third antigen; one or more sample inlets on the cartridge in fluid communication with the one or more conjugation regions; and one or more windows through which the specific regions of the solid phase substrate to which the first, second and third agents are bound may be visualized.

The anionic surfactant of the lysis buffer may comprise sarkosyl and wherein the osmotic agent of the lysis buffer comprises sucrose. Any of these assay kits may include a diluting buffer, as described herein.

The cartridge may include a housing that encloses one or more (e.g., three, arranged in parallel) solid phase substrates. For example, a cartridge may comprise a plurality (e.g., 3) of solid phase substrates, wherein each solid phase substrate holds one of the first agent, the second agent or the third agent. Alternatively, cartridge may comprise a single solid phase substrate holding each of the first agent, second agent and third agent. The first antigen may be a cell surface antigen specific to *H. influenzae*, the second antigen may be a cell surface antigen specific to *M. catarrhalis* and the third antigen may be a cell-surface antigen specific to *S. pneumoniae.*

Any of these cartridge regions may include a conjugation region. The conjugation region may hold the unbound antigen binding agent, which may be marked with a marker (e.g., a visualizable marker such as a colloidal metal, colored bead, etc.). The antigen binding agent(s) in the conjugation region may be in solution (e.g., in a pre-wetted conjugation sponge or conjugation pad, a fluid conjugation chamber, etc.). Alternatively, the antigen binding agent (e.g., antibody, FAB, etc.) may be lyophilized and stored in this region, and the sample solution may re-suspend the antigen binding agent, allowing it to bind before entering the portion(s) of the solid phase substrate to to which antigen binding agent(s) are bound. In variations having a single solid phase substrate with discrete regions for each of the different types of antigen binding agents binding to specific bacterial types, a single conjugation region (e.g., holding the fourth agent, fifth agent and sixth agent) may be used. Any of these cartridges may include multiple conjugation regions. In particular, cartridges having parallel fluid paths may include multiple conjugation regions, where each conjugation region holds the labeled antigen binding agent specific to one of the types of bacteria corresponding to the bound antigen binding agent on the downstream solid phase substrate.

Any of these kits may include a cartridge a single sample inlet. The single inlet may feed into a single fluidics line or into a plurality (e.g., 3) of parallel fluidic lines that may connect to, e.g., a sample region or chamber (e.g., sample pad), a conjugation region or chamber (e.g., conjugation pad), an incubation region or chamber (e.g., incubation pad), a solid phase substrate region (e.g., detection region, which may be combined with the incubation region or chamber or separate from it), and/or a waste chamber or region (e.g., absorbent pad). The fluid path(s) through the cartridge may include an air inlet. For example, an air inlet may be present at an opposite end of the fluid path from the sample input.

The one or more windows in the cartridge may allow viewing of the solid phase substrate, allowing detection (e.g., visual, optical, etc.) of binding of antigen to the solid phase substrate(s) in this region (e.g., the detection region) where the tethered/bound antigen binding agent specifically bound to the solid phase substrate. In some variations the method includes reading/detection of the binding using a reader including an optical reader (e.g., florescent reader, etc.), visual (e.g., manual or automatic) reading, etc. The cartridges described herein may be configured to be compatible with one or more readers, including optical readers such as the Quidel "Sophia" device that is an optical reader that uses fluorescent markers (see, e.g., www.quidel.com/immunoassays/sofia-tests-kits) or the Becton Dickinson "Veritor" System (see, e.g., www.bd.com/ds/veritorsystem/poctesting.asp).

As mentioned, any of the antigen binding agents (e.g., any or all of the first agent, second agent, third agent, fourth agent, fifth agent, and sixth agent) may comprise an antibody or an antibody fragment.

The one or more solid phase substrates may be, for example, a membrane or other surface onto which an antigen binding agent is immobilized. The substrate may be smooth, porous, rough, etc. In some variations a single solid phase substrate is used to which each of the multiple antigen binding agents (e.g., the first, second and third agents, each specific to an antigen of one of *M. cat, S. pneumo,* or *H. flu*). Thus, in any of these variations, the one or more conjugation regions may be a single conjugation region, and the one or more sample inlets may be a single sample inlet, and the single solid phase substrate may be upstream of the single conjugation region that is upstream of the single sample inlet.

Any of these assay kits may also include a control region on the solid phase substrate. The control region may include an immobilized binding agent that binds to one or more of the soluble antigen binding agents in the assay (e.g., the first, second or third agent) configured to bind to one or more of the fourth agent, fifth agent, or sixth agent and an absorbent pad, downstream of the specific regions of the solid phase substrate to which the first, second and third agents are bound.

For example, described herein are assay kits for concurrently detecting *H. influenzae, M. catarrhalis* and *S. pneumoniae* from a mucosal sample, the assay kit comprising: a lysis buffer to lyse cells within the sample and form a single sample solution, wherein the lysis buffer comprises between 0.01% and 5% (w/w) of the anionic surfactant and between 0.1% and 15% (w/w) of the osmotic agent; a cartridge containing a solid phase substrates holding a first agent that that binds specifically to a first antigen specific to *H. influenzae* but not *M. catarrhalis* or *S. pneumoniae*, a second agent that binds specifically to a second antigen specific to *M. catarrhalis* but not *H. influenzae* or *S. pneumoniae*, and a third agent that binds specifically to a third antigen specific to *S. pneumoniae* but not *M. catarrhalis* or *H. influenzae*, wherein the first, second and third agents are bound to specific regions of the solid phase substrate; and a conjugation region within the cartridge, conjugation region in fluid communication with the solid phase substrate and comprising a fourth agent that is labeled and that binds specifically to the first antigen, a fifth agent that is labeled and that binds specifically to the second antigen, and a sixth agent that is labeled and that bind specifically to the third antigen; a sample inlet on the cartridge in fluid communication with the conjugation region; and one or more windows exposing the specific regions of the solid phase substrate to which the first second and third agents are bound.

Also described herein are methods of concurrently detecting *H. influenzae, M. catarrhalis* and *S. pneumoniae* from a mucosal sample. For example a method of concurrently detecting *H. influenzae, M. catarrhalis* and *S. pneumoniae* from a mucosal sample may include: adding the sample to a lysis buffer to lyse cells within the sample and form a single sample solution, wherein the lysis buffer comprises both an anionic surfactant and an osmotic agent; adding the sample solution to a cartridge containing one or more solid phase substrates holding a first agent that that binds specifically to a first antigen specific to *H. influenzae* but not *M. catarrhalis* or *S. pneumoniae*, a second agent that binds specifically to a second antigen specific to *M. catarrhalis* but not *H. influenzae* or *S. pneumoniae*, and a third agent that binds specifically to a third antigen specific to *S. pneumoniae* but not *M. catarrhalis* or *H. influenzae*, wherein the first, second and third agents are bound to specific regions of the one or more solid phase substrates in the cartridge; and contacting the sample solution, either before or after it is added to the cartridge, with a fourth agent that is labeled and that binds specifically to the first antigen, a fifth agent that is labeled and that binds specifically to the second antigen, and a sixth agent that is labeled and that bind specifically to the third antigen.

In general, the agents that bind specifically to the antigens (e.g., first antigen, second antigen, third antigen) described herein do not bind to antigens (proteins) from the majority of other commernsural bacteria in the sinus specimen, in addition to having little or any binding to other antigens other than the intended/target antigen. For example, the antigen binding agent (e.g., antibody or antibody fragment) may bind specifically to the target first antigen (e.g., from *H. flu*), but not to non-target antigens (e.g., from *M. Cat* or *S. pneumo*).

In any of these methods, kits and compositions described herein, the lysis buffer may comprise between 0.01% and 5% (w/w) of the anionic surfactant and between 0.1% and 15% (w/w) of the osmotic agent. The anionic surfactant of the lysis buffer may comprise between 0.01% and 5% (w/v)

of sarkosyl and the osmotic agent of the lysis buffer may comprises between 0.1% and 15% (w/w) of sucrose.

Any of these methods may include adding a diluting buffer to the sample solution prior to adding it to the cartridge.

Adding the sample solution to the cartridge may include applying a single bolus of sample or applying multiple boluses of sample. For example, adding sample solution to the cartridge may comprise dividing the sample between a plurality of regions in the cartridge, wherein each region is in fluid communication with separate solid phase substrates and wherein each solid phase substrate holds one of the first agent, the second agent or the third agent.

Adding the sample solution to the cartridge may comprise adding the sample solution to a single region in the cartridge that is in fluid communication with a solid phase substrate holding each of the first agent, second agent and third agent. In any of these methods, kits, and compositions described herein, the antigens to each bacterial type may be cell surface antigens. For example the first antigen may be a cell surface antigen specific to *H. influenzae*, the second antigen may be a cell surface antigen specific to *M. catarrhalis* and the third antigen may be a cell-surface antigen specific to *S. pneumoniae*.

Any of these methods may include passing the sample solution over the one or more solid phase substrates in the cartridge after contacting the sample solution with the fourth, fifth and sixth agents.

The step of contacting the sample solution with the fourth, fifth and sixth agent may comprise passing the sample through one or more portions of the cartridge upstream from the specific regions of the solid phase substrate in the cartridge to which the first, second and third agents are bound.

Any of the methods described herein may include visually identifying which strain (e.g., *M. cat, S. pneumo,* or *H. flu*) is present in the sample solution by identifying that the fourth agent has bound to the first antigen in the solid phase substrate region where the first antigen was bound, and/or the fifth agent has bound to the second antigen in the solid phase substrate region where the second antigen was bound, and/or that the sixth agent has bound to the third antigen in the solid phase substrate region where the third antigen was bound.

The sample solution may be exposed (e.g., contacted with) the labeled antigen binding agents either before or after it is added to the cartridge. For example, the sample solution may be contacted with the fourth agent, fifth agent, and sixth agent before it is added to the cartridge, or the sample solution may be contacted with the fourth agent, fifth agent, and sixth agent after it is added to the cartridge.

For example, a method for concurrently detecting *H. influenzae, M. catarrhalis* and *S. pneumoniae* from a mucosal sample may include: adding the sample to a lysis buffer to lyse cells within the sample and form a single sample solution, wherein the lysis buffer comprises between 0.01% and 5% (w/w) of the anionic surfactant and between 0.1% and 15% (w/w) of the osmotic agent; adding the sample solution to a cartridge containing a solid phase substrate holding a first agent that that binds specifically to a first antigen specific to *H. influenzae* but not *M. catarrhalis* or *S. pneumoniae*, a second agent that binds specifically to a second antigen specific to *M. catarrhalis* but not *H. influenzae* or *S. pneumoniae*, and a third agent that binds specifically to a third antigen specific to *S. pneumoniae* but not *M. catarrhalis* or *H. influenzae*, wherein the first, second and third agents are bound to specific separate regions of the solid phase substrate; contacting the sample solution with a fourth agent that is labeled and that binds specifically to the first antigen, a fifth agent that is labeled and that binds specifically to the second antigen, and a sixth agent that is labeled and that bind specifically to the third antigen; and visually identifying through a window in the cartridge that the fourth agent has bound to the first antigen, the fifth agent has bound to the second antigen, or the sixth agent has bound to the third antigen.

Although the kits (e.g., assay kits, systems) described herein in these examples are configured to test for the presences of three bacteria (e.g., *S. pneumoniae* but not *M. catarrhalis* or *H. influenzae*), any of these kits and methods may be instead configured to identify the presence of two or more than three bacteria. In particular, any of the methods and kits described herein may be configured to determine the presence of *S. pneumoniae* and/or *H. influenzae*, which together account for approximately 70-75% of bacterial sinusitis.

Also described herein are nasal sampling devices that may be used by themselves or as part of a kit or system for testing a nasal (e.g., mucous) material, particularly from the middle meatus region of the sinus.

For example, a nasal sampling device for obtaining a sinus secretion sample from a subject's sinus may include: an elongate body having a distal end region that is bent relative to a proximal region by between 15 degrees and 30 degrees; a sample collector on a distal end of an extendable shaft, wherein the sample collector is configured to collect a sample of sinus fluid, further wherein the sample collector is housed entirely within the distal end of the elongate body in a retracted position; and a control coupled to the extendable shaft and configured to extend and retract the sample collector in and out of the distal end of the elongate body; wherein the nasal sampling device has a retracted configuration with the sample collector retracted and housed entirely within the distal end of the elongate body, a sampling configuration with the sample collector extended distally out of a distal opening of the distal end region of the elongate body a first distance between 0.5 cm to 3 cm, and an elution configuration with the sample collector extended distally out of the distal opening of the distal end region of the elongate body a second distance that is greater than the first distance.

A nasal sampling device for obtaining a sinus secretion sample from a subject's sinus, wherein the nasal sampling device includes: an elongate body having a distal end region that is bent relative to a proximal region by between 15 degrees and 30 degrees; a sample collector on a distal end of an extendable shaft, wherein the sample collector is configured to collect a sample of sinus fluid, further wherein the sample collector is housed entirely within the distal end of the elongate body in a retracted position; and a control coupled to the extendable shaft, the control having a first set point wherein the sample collector is extended distally out of a distal opening of the distal end region of the elongate body a first distance between 0.5 cm to 3 cm, the control having a second set point, wherein the sample collector is retracted and housed entirely within the distal end of the elongate body, the control having a third set point, wherein the sample collector is extended distally out of the distal opening of the distal end region of the elongate body a second distance that is greater than the first distance.

Any of these nasal sampling devices may include a spacer (which may also be a protrusion, bump, deflector, etc.) on the extendable shaft proximal to the sample collector, wherein the spacer is configured to prevent the sample collector from contacting an inner surface of the elongate body when the sample collector is retracted into the distal end of the elongate body. Centering the sample collector in this manner may prevent the sample collector from getting contaminated by other bacteria (e.g., from regions other than the sampling region) by contacting the outer housing of the elongate body, which may contact other regions; this may also prevent prematurely releasing material or limiting the amount of material held by the sample collector (e.g., swab).

Any of the nasal sampling devices described herein may include a releasable stop configured to prevent the control from selecting the third set point until the stop is released. Any appropriate stop may be used, including an interference region between the extendable shaft and the elongate body and/or handle, a latch, etc. For example, the stop may comprise a detachable handle configured to releasably couple to a distal end of the extendable shaft. The stop may include a releasable connector connecting the extendable shaft to the stop.

In general, the dimensions of the nasal sampling may be configured for use within the nasal passages (e.g., sinus) so that the sample collector may be extended at the correct region of the apparatus to reach the desired portion of the sinus (e.g. the middle meatus region, the upper meatus region, the lower meatus region, etc.). Both the angle of the distal end of the device relative to more proximal regions as well as the size and shape of the device may be configured to allow external (through the nares/nostril) application of the device to sample the mucosa. For example the distal end region of the elongate body may be between 1.5 and 3.5 cm long (e.g., between 1 and 5 cm long, between 1 and 4 cm long, between 1.5 and 4 cm long, between 2 and 3 cm long, etc.). Similarly, the proximal region of the elongate body may be greater than 1 cm long (e.g., greater than 1.5 cm, greater than 2 cm, greater than 3 cm, greater than 4 cm, greater than 5 cm, between 1 cm and 30 cm, between 1 cm and 20 cm, between 1 cm and 15 cm, etc.).

Similarly, the sample collector may be any appropriate size (e.g., between 0.2 and 2 cm long, between 0.4 and 1.5 cm long, between 0.5 and 1.2 cm long, etc.). The extendable shaft may be any appropriate length (e.g., greater than 2 cm, greater than 5 cm, greater than 10 cm, between 1 cm and 30 cm, between 1 cm and 20 cm, between 1 cm and 15 cm, between 1 cm and 12 cm, etc.). The extendable shaft may be configured (by operation of the control) to extend from the distal end region of the elongate body by a predetermined amount. For example, as mentioned above, in a sampling position the sample collector may be extended from the distal end by between 0.5 cm to 3 cm. In the elution configuration the extendable shaft is extended away from the elongate body further than in the sampling configuration. This may be achieved by advancing the extendable shaft relative to the elongate body, or by retracting the distal end region of the elongate body proximally, relative to the extendable shaft, or in some variation by removing all or a portion of the distal end region of the elongate shaft. For example, in some variations, the distance that the sample collector extends from the elongate body in the elution configuration (e.g., the second distance) may be 1.0 cm or greater than the first distance.

As described herein, in general the sample collector may be a swab, including in particular a flocked swab. It may also be beneficial to use a swab having ends which are branched (e.g., bifurcated, or multiply-divided).

In any of these variations, the control on the nasal sampling device may be coupled to a handle at the proximal end of the device. For example, any of these apparatuses may include a handle body extending proximally from the elongate body, wherein the extendable shaft extends through the elongate body and into an internal channel within the handle body. The extendable shaft may generally be a flexible elongate shaft. The extendable shaft may be configured to slide within the elongate body.

Thus, any of the devices described herein may include a control configured as a slider. Other examples of controls may include dials, knobs, switches, or the like. In some variations a control that may be included (e.g., in addition to a slider or other control) may be a finger ring. In some variations a control comprises may be a compression actuator configured to be compressed to select the third set point in which the sample collector is extended distally out of the distal opening of the distal end region of the elongate body the second distance. In general, a control may be configured to be distally advanced to select the first set point in which the sample collector is extended distally out of a distal opening of the distal end region of the elongate body the first distance. In some variations a control comprises a push button configured to be depressed to select the third set point in which the sample collector is extended distally out of the distal opening of the distal end region of the elongate body the second distance.

Any of these devices described herein may include a lock configured to lock the control at one or more of: the first set point, the second set point or the (optional) third set point.

Any of the devices described herein may include a depth gauge configured to display a position of the sample collector to a user of the device. The distal end region may be configured to have an open configuration when the sample collector is advanced out of the distal end of the elongate body, and a closed configuration when the sample collector is in the retracted position.

Any of these devices may also include a depth stop to prevent the sampling device from being inserted too deep into a nasal and/or sinus cavity of a subject.

For example, a nasal sampling device for obtaining a sinus secretion sample from a subject's sinus may include: a hollow elongate body having a distal end region that is bent relative to a proximal region by between 15 degrees and 30 degrees; a sample collector on a distal end of an extendable shaft, wherein the sample collector is configured to collect a sample of sinus fluid, further wherein the sample collector is housed entirely within the distal end of the elongate body in a retracted position; a control coupled to the extendable shaft, the control having a first set point wherein the sample collector is extended distally out of a distal opening of the distal end region of the elongate body a first distance between 0.5 cm to 3 cm, the control having a second set point, wherein the sample collector is retracted and housed entirely within the distal end of the elongate body, the control having a third set point, wherein the sample collector is extended distally out of the distal opening of the distal end region of the elongate body a second distance that is 1.0 cm or greater than the first distance; and a projection on the extendable shaft proximal to the sample collector, wherein the projection is configured to prevent the sample collector from contacting an inner surface of the hollow elongate body when the sample collector is retracted into the distal end of the elongate body.

Also described herein are methods including methods of using a nasal sampling device. For example, a method for detecting one or more nasal bacteria in a patient, using a nasal sampling device including an elongate body having a distal end region that is bent relative to a proximal region by between 15 degrees and 30 degrees, a sample collector on a distal end of an extendable shaft, and a control coupled to the extendable shaft, the control having a first set point wherein the sample collector is extended distally out of a distal opening of the distal end region of the elongate body a first distance, the control having a second set point, wherein the sample collector is retracted and housed entirely within the distal end of the elongate body, the control having a third set point, wherein the sample collector is extended distally out of the distal opening of the distal end region of the elongate body a second distance that is greater than the first distance, may include: advancing the distal end region of the nasal sampling device through a nares of the patient until the distal end region is adjacent to a middle meatus of a sinus; setting the control to the first set point to extend the sample collector into the middle meatus so that it contacts a secretion fluid in the middle meatus; setting the control to the second set point to retract the sample collector entirely within the distal end; withdrawing the nasal sampling device out of the patient's nares; and testing the secretion fluid with an immunoassay test after withdrawing the nasal sampling device.

The secretion fluid may be tested using any of the method described above (e.g., concurrently detecting *H. influenzae, M. catarrhalis* and *S. pneumoniae* from a mucosal sample). For example, testing the secretion fluid may include setting the control to the third set point, so that the sample collector is extended distally out of the distal opening of the distal end region of the elongate body a second distance that is greater than the first distance and contacting the sample collector with a buffer solution. Testing the secretion fluid may comprise contacting the secretion fluid with a lysing solution. For example, testing the secretion fluid may comprise contacting the secretion fluid with a lysing solution comprising both an osmotic agent and an anionic surfactant. In some variations, testing the secretion fluid comprises contacting the secretion fluid with a lysing solution comprising Sodium Lauroyl Sarcosinate and sucrose to form a sample fluid and contacting the immunoassay test with the sample fluid. Testing the secretion fluid may comprise testing the secretion fluid with one or more agents that bind to: an antigen specific to *H. influenzae*, an antigen specific to *M. catarrhalis*, or an antigen specific to *S. pneumoniae*. Testing the secretion fluid may comprises testing the secretion fluid with one or more agents that bind to each of: an antigen specific to *H. influenzae*, an antigen specific to *M. catarrhalis*, or an antigen specific to *S. pneumoniae*.

Also described herein are systems for detecting bacterial sinusitis that generally include a mucosal sampling device as described herein any any of the assays/kits described herein. For example, a system for detecting bacterial sinusitis may include a nasal sampling device for obtaining a sinus secretion sample from a subject's sinus, wherein the nasal sampling device includes: an elongate body having a distal end region that is bent relative to a proximal region by between 15 degrees and 30 degrees; a sample collector on a distal end of an extendable shaft, wherein the sample collector is configured to collect a sample of sinus fluid, further wherein the sample collector is housed entirely within the distal end of the elongate body in a retracted position; a control coupled to the extendable shaft, the control having a first set point wherein the sample collector is extended distally out of a distal opening of the distal end region of the elongate body a first distance, the control having a second set point, wherein the sample collector is retracted and housed entirely within the distal end of the elongate body, the control having a third set point, wherein the sample collector is extended distally out of the distal opening of the distal end region of the elongate body a second distance that is greater than the first distance; and an immunoassay kit for detecting at least one bacterial strain associated with bacterial sinusitis infections.

The immunoassay kit may include a lysis buffer comprising both an anionic surfactant and an osmotic agent, such as an anionic surfactant between between 0.01% and 5% (w/w) and an osmotic agent between 0.1% and 15% (w/w). In some variations the immunoassay kit may comprises a lysis buffer comprising sarkosyl and sucrose.

In any of these variations, the immunoassay kit may include a cartridge, and the cartridge may include a sample inlet for depositing a sample, a sample pad onto which the sample is absorbed prior to elution, a conjugate pad containing at least one antibody complexed with a detectable marker, a detector pad comprising at least one zone, wherein the zone comprises antibodies directed to at least one bacterial antigen bound to the detector pad, and a visualization window for viewing the results of the assay.

The immunoassay kit may comprise a cartridge comprising a sample inlet for depositing a sample, a sample pad onto which the sample is absorbed prior to elution, a conjugate pad containing a plurality of antibodies complexed with a detectable marker, a detector pad comprising a plurality of different zones, wherein each zone comprises antibodies directed to at least one bacterial antigen bound to the detector pad, and a visualization window for viewing one or more of the zones of the detector pad. The kit may include a sampling device with a spacer on the extendable shaft proximal to the sample collector, wherein the spacer is configured to prevent the sample collector from contacting an inner surface of the elongate body when the sample collector is retracted into the distal end of the elongate body.

A system for detecting bacterial sinusitis may include: a nasal sampling device for obtaining a sinus secretion sample from a subject's sinus, wherein the nasal sampling device includes: an elongate body having a distal end region that is bent relative to a proximal region by between 15 degrees and 30 degrees; a sample collector on a distal end of an extendable shaft, wherein the sample collector is configured to collect a sample of sinus fluid, further wherein the sample collector is housed entirely within the distal end of the elongate body in a retracted position; a control coupled to the extendable shaft, the control having a first set point wherein the sample collector is extended distally out of a distal opening of the distal end region of the elongate body a first distance, the control having a second set point, wherein the sample collector is retracted and housed entirely within the distal end of the elongate body, the control having a third set point, wherein the sample collector is extended distally out of the distal opening of the distal end region of the elongate body a second distance that is greater than the first distance; and an immunoassay kit for detecting multiple bacterial strains associated with bacterial sinusitis infections, the kit comprising a lysis buffer comprising both an anionic surfactant between between 0.01% and 5% (w/w) and an osmotic agent between 0.1% and 15% (w/w).

BRIEF DESCRIPTION OF THE DRAWINGS

FIGS. 14A-14E illustrate aspects of a device configured to sample a sinus in accordance with some embodiments.

FIG. 24A shows an assay housing, a sample pad for accepting the sample, a conjugate pad containing the first antibody with complexed detector molecule, a detection pad along which the sample will run and come into contact with zones of corresponding second antibodies bound to the detection pad for each antigen of interest. FIG. 24B shows a sample on the sample pad, the set of first antibodies on the conjugate pad, and zones on the detection pad holding different antibodies. FIG. 24C shows an eluting solution (dark) that runs across the detection pad and brings first antibodies-detector molecule coupled to corresponding antigens in contact with the second set of antibodies. FIG. 24D shows the completed assay where the first antibodies-detector molecule coupled to corresponding antigens is now also bound to the corresponding second antibodies for each different antigen of interest.

FIG. 27 is a table illustrating the effectiveness of various lysis buffers on three of the types of bacteria to be concurrently examined by the apparatuses and methods described herein.

FIG. 28 is a table illustrating two examples of lysis buffers compatible for the concurrent detection of multiple different cell types (e.g., *M. cat, S. pneumo* and *H. flu*) as described herein.

FIG. 29 is a table illustrating two exemplary dilution buffers compatible for the concurrent detection of multiple different cell types as described herein. In these examples, the lysis buffer #1 (on left of FIG. 28) was used with dilution buffer #1 (on left of FIG. 29), and lysis buffer #2 (on right in FIG. 28) was used with dilution buffer #2 (on right in FIG. 29).

FIGS. 30A-30C illustrate detection of each of *S. pneumo, M. cat,* and *H. flu,* respectively, using the kits and methods described herein. The concentration of cells detected (expressed as colony forming units (CFU)/sample) in this prototype show thresholds for visual detection from an exemplary lateral flow assay such as the one illustrated in FIGS. 24A-24D and 26. FIG. 30A illustrates that the prototype assay detected the PsaA antigen (the cell-surface marker for *S. pneumo*) at bacterial concentrations ranging from $10^3$-$10^7$ per 100 µl sample with resolution at $1\times10^4$. FIG. 30B illustrates that the prototype assay detected the CD antigen (a cell-surface marker for *M. cat*) at bacterial concentrations ranging from $10^4$-$10^7$ per 100 µl sample with good resolution at $1\times10^5$. FIG. 30C illustrates that the prototype assay detected the OMP-P5 antigen (a cell-surface marker for *H. flu*) at bacterial concentrations ranging from $10^5$-$10^7$ per 100 µl sample with good resolution at $2\times10^5$.

FIG. 31 is one example of a cartridge having a single solid phase substrate (combining three separate assays, one each for a different bacterial type) that can simultaneously test for the presence of each of three different types of bacteria.

FIG. 32 is an example of a cartridge configured to simultaneously test for the presence of each of three different types of bacteria in parallel; the cartridge include three separate solid phase substrates and three fluidic pathways. Although the example shown in FIG. 32 includes three separate inlet ports, a single port having three fluidic paths may be used.

DETAILED DESCRIPTION

Apparatuses (including devices, systems, kits, and assays) and methods are disclosed herein for diagnosing sinusitis, including obtaining a sample of sinus fluid from a patient and/or determining if the patient is infected with one or more of *H. influenzae* (*H. flu*), *M. catarrhalis* (*M. cat*) and *S. pneumoniae* (*S. pneumo*). For example, described herein are sample devices for accurately and quickly sampling sinus fluid within the sinus, such as the middle meatus or maxillary sinus, and assays for rapidly testing this sample to determine the presence of bacteria, viruses, and other diseases of interest. The fast diagnosis of the presence or absence of the diseases of interest can improve the treatment of the patient.

Figure 1:
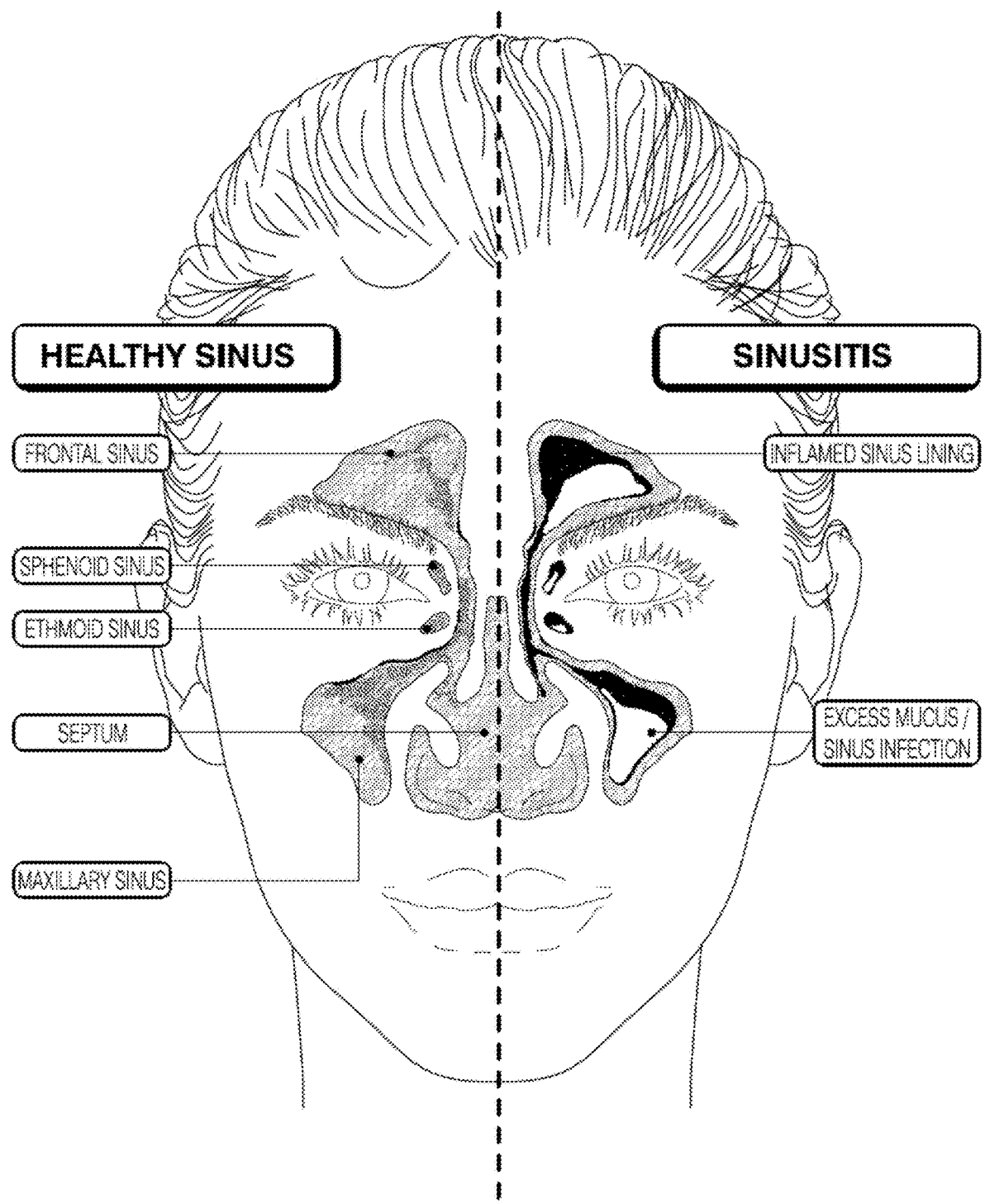
FIG. 1 is an illustration of a healthy sinus and a sinus showing symptoms of sinusitis.
Figure 2:
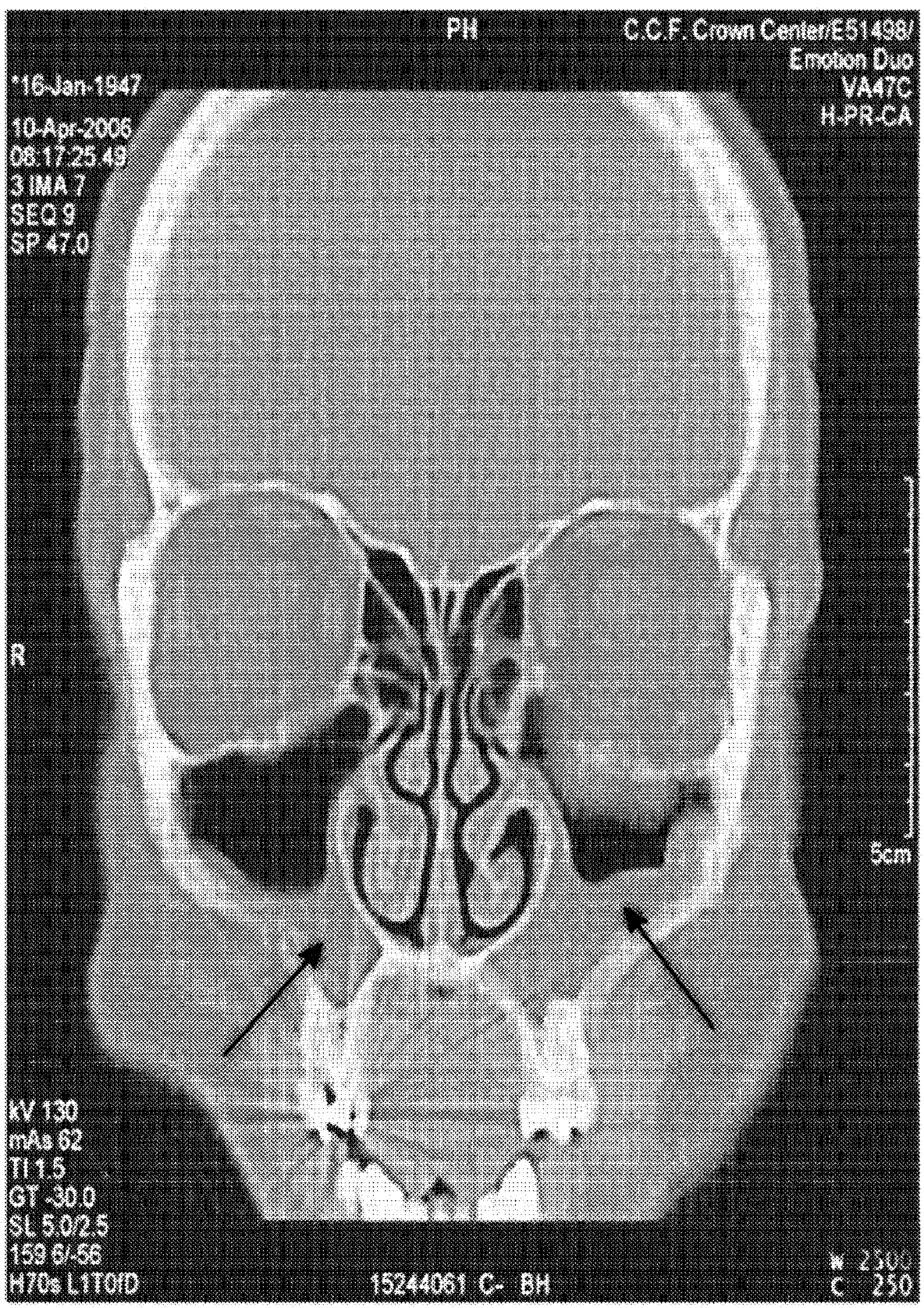
FIG. 2 is a CT scan image of a patient exhibiting symptoms of sinusitis.

FIG. 1 illustrates a comparison between a healthy sinus and a sinus with sinusitis. The sinusitis can cause excess mucous in the frontal sinus and maxillary sinus. Other symptoms can include inflamed sinus lining and a sinus infection. FIG. 2 illustrates a CT image of a patient with chronic sinusitis. The arrows indicate the congested sinuses typical of chronic sinusitis.

Testing the mucous/sinus fluid within the sinus, such as the middle meatus or maxillary sinus, can help diagnose the condition causing the discomforting symptoms in the patient. The sinus fluid can indicate a bacterial infection, viral infection, or provide other information to help diagnose and formulate an efficient and effective therapeutic treatment. Other examples of areas of the sinuses that can be tested using the devices and methods disclosed herein are the frontal sinuses, maxillary sinuses, ethmoid sinuses, and sphenoid sinuses. The devices disclosed herein can also have a tip geometry configured to be advanced in other passages within the body. For example the devices can be configured to collect a sample from the nasopharynx region, esophageal passage, from the middle ear, and other portions of the anatomy that a skilled artisan would want to sample.

Figure 3A:
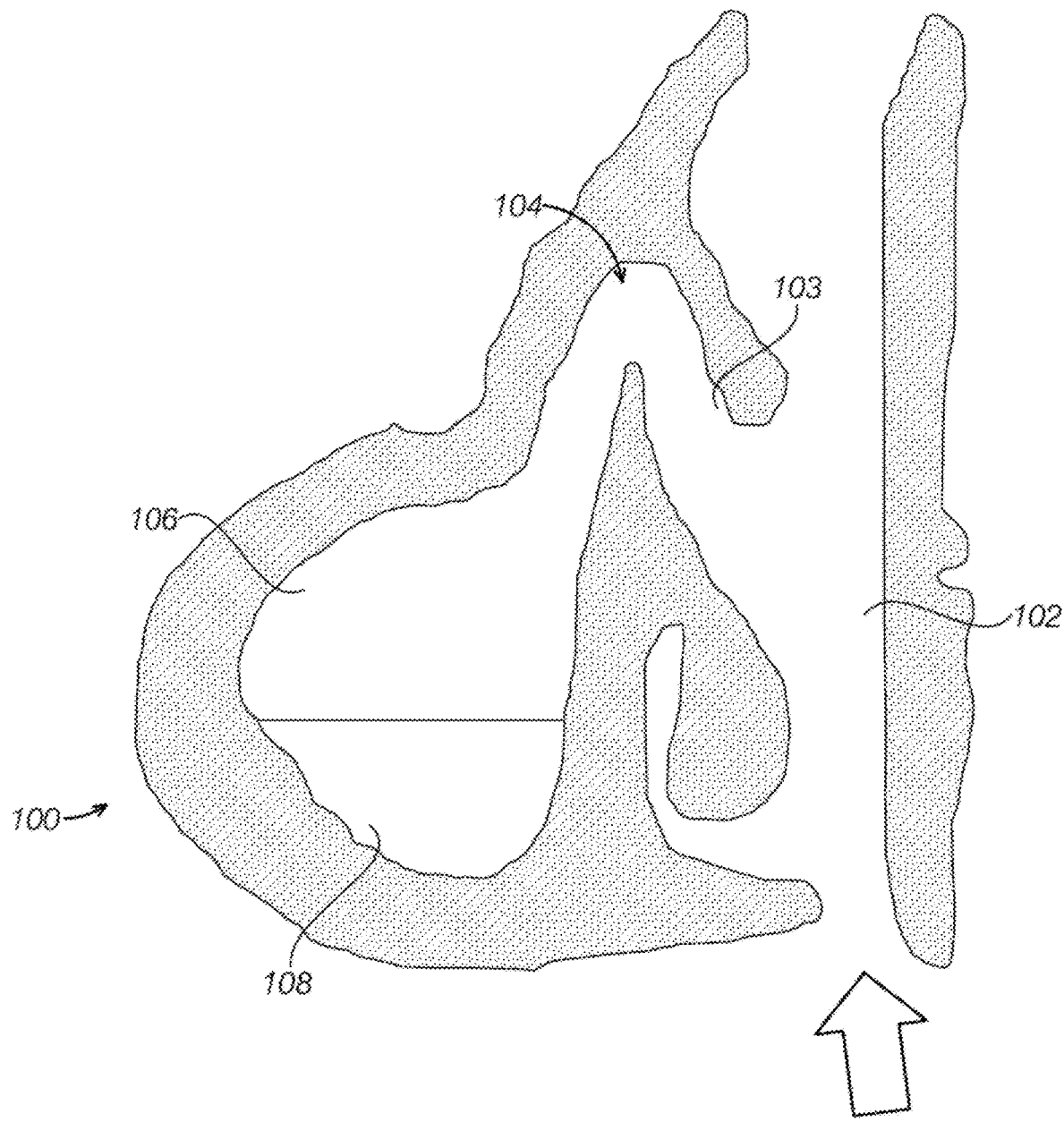
FIGS. 3A-3F show an example of a method for sampling a sinus in accordance with some embodiments.
Figure 3B:
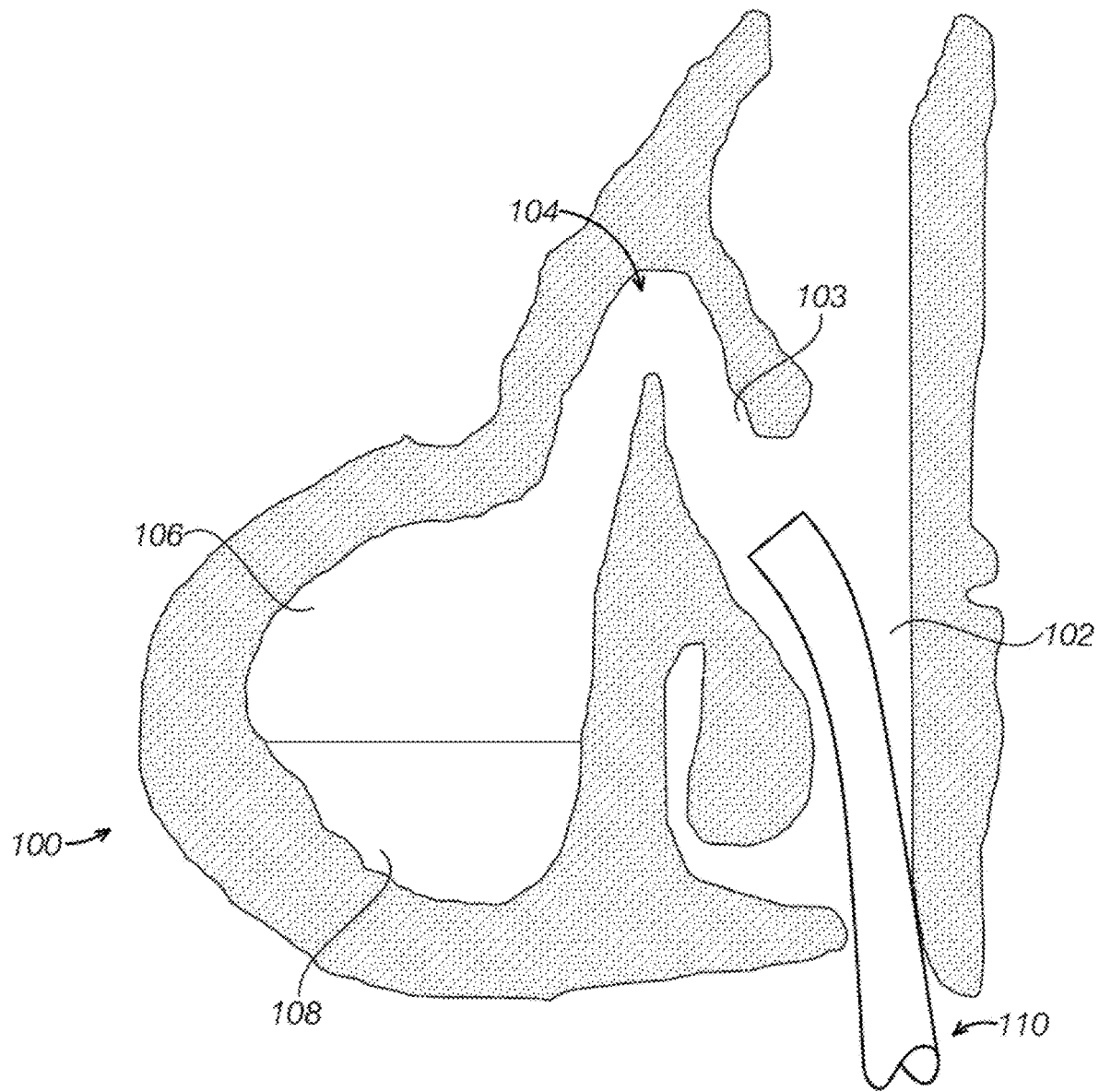
Figure 3C:
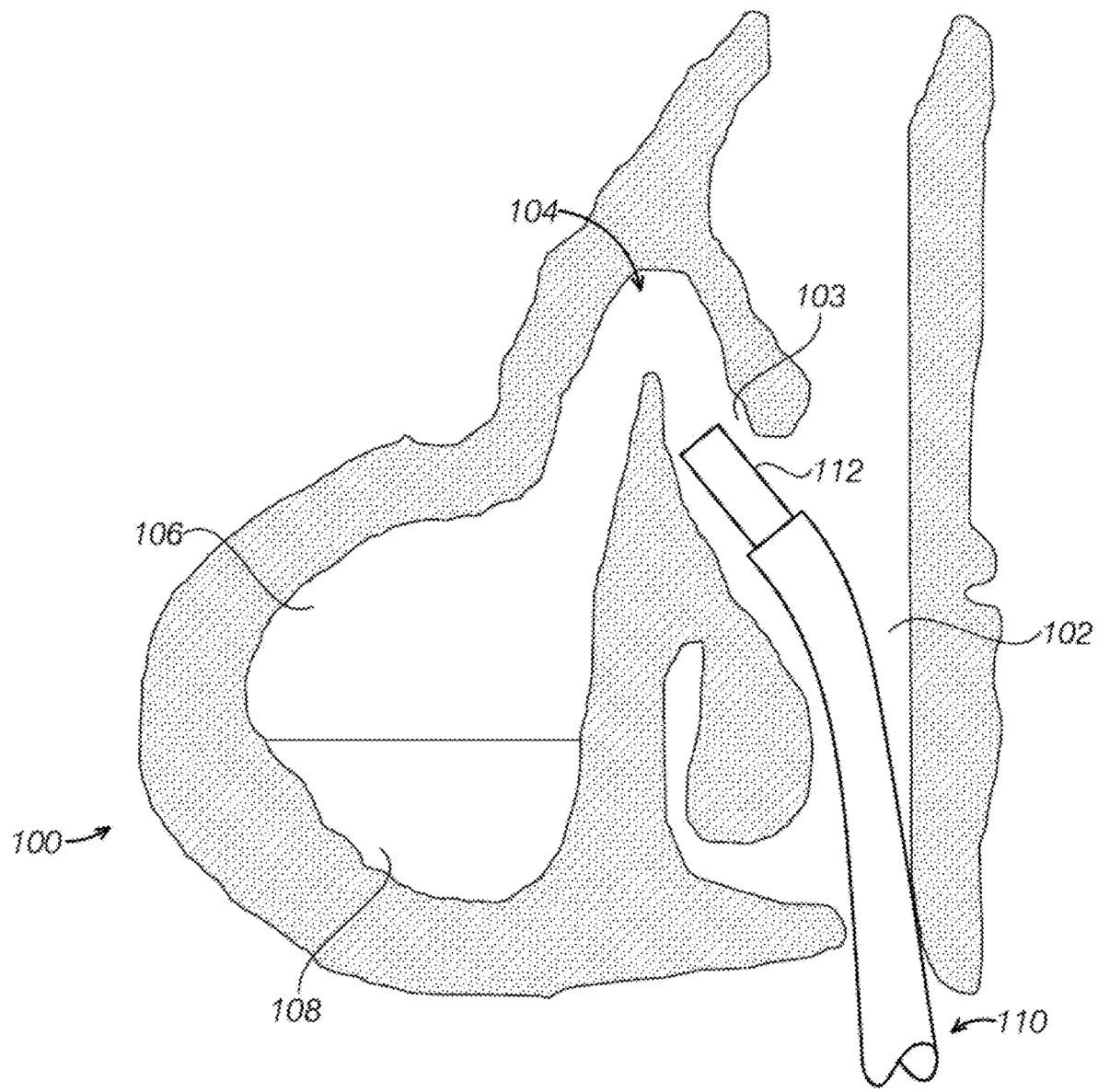
Figure 3D:
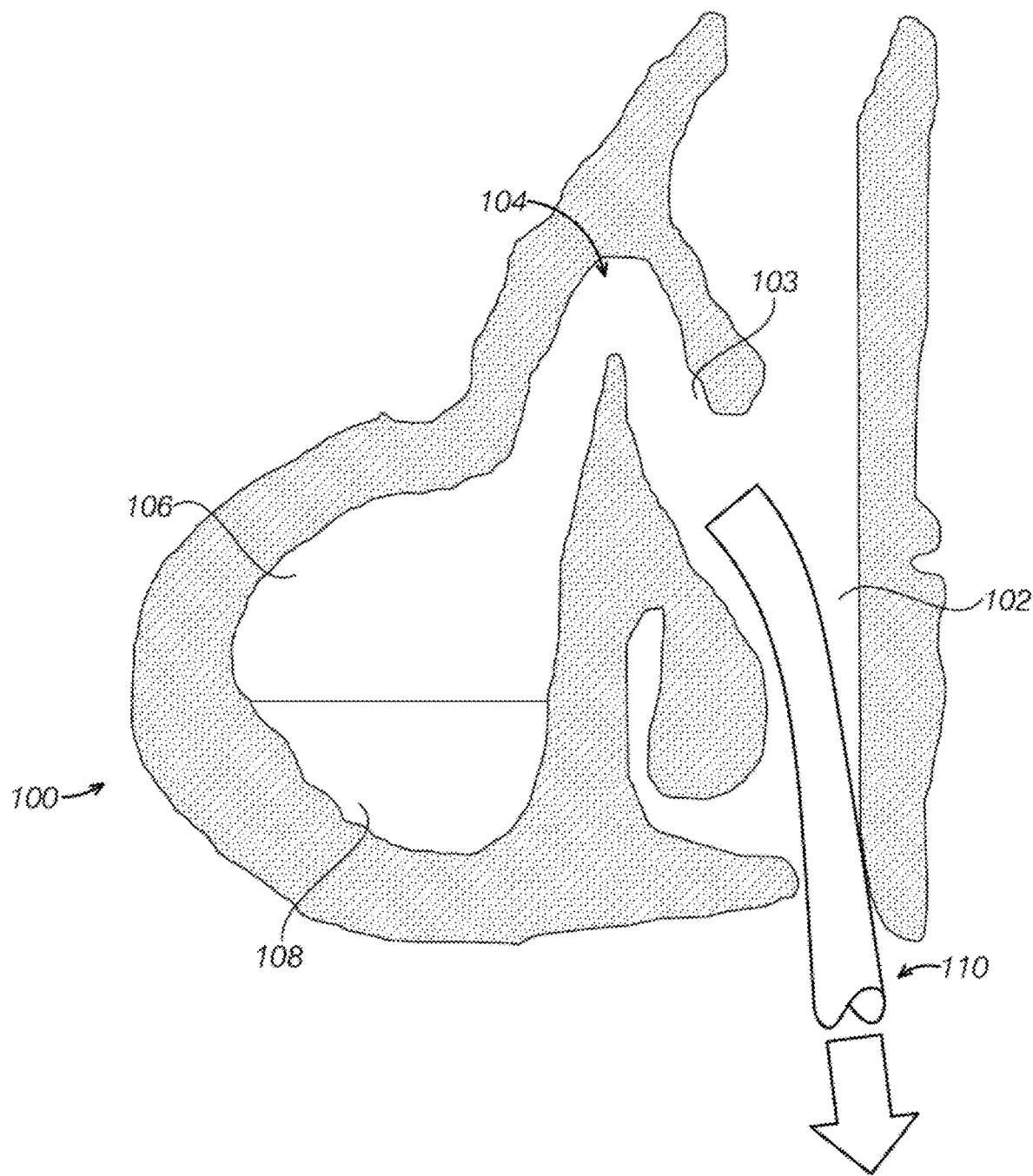

FIGS. 3A-3D show an example of a method for sampling a sinus in accordance with some embodiments. FIGS. 3A-3D include a schematic illustrate of a portion of a sinus 100 including the nares 102, middle meatus 103, ostium of the maxillary sinus 104, maxillary sinus 106, and sinus fluid 108 within the maxillary sinus 106. FIG. 3B is a schematic illustration of a portion of a sampling device 110. Any of the sampling devices disclosed herein can be used as the sampling device 110 as illustrated in FIGS. 3A-3D. The sampling device 110 includes a distal portion configured to be advanced through the nares 102 to an area adjacent to the middle meatus 103 and maxillary sinus 104 as shown in FIG. 3B. After the sampling device 110 has been advanced to a desired area adjacent to the middle meatus 103, the sample collector 112 can be advanced distally to contact and sample sinus fluid in the middle meatus 103 as shown in FIG. 3C. After the sample of the sinus fluid has been obtained by the sample collector 112, the sample collector 112 can be retracted back into the sampling device 110. After the sample collector 112 has been retracted back into the sampling device 110, the sampling device 110 can be withdrawn from the nares 102 as shown in FIG. 3D. The sampling device 110 can be used to sample either of the nares.

Figure 3E:
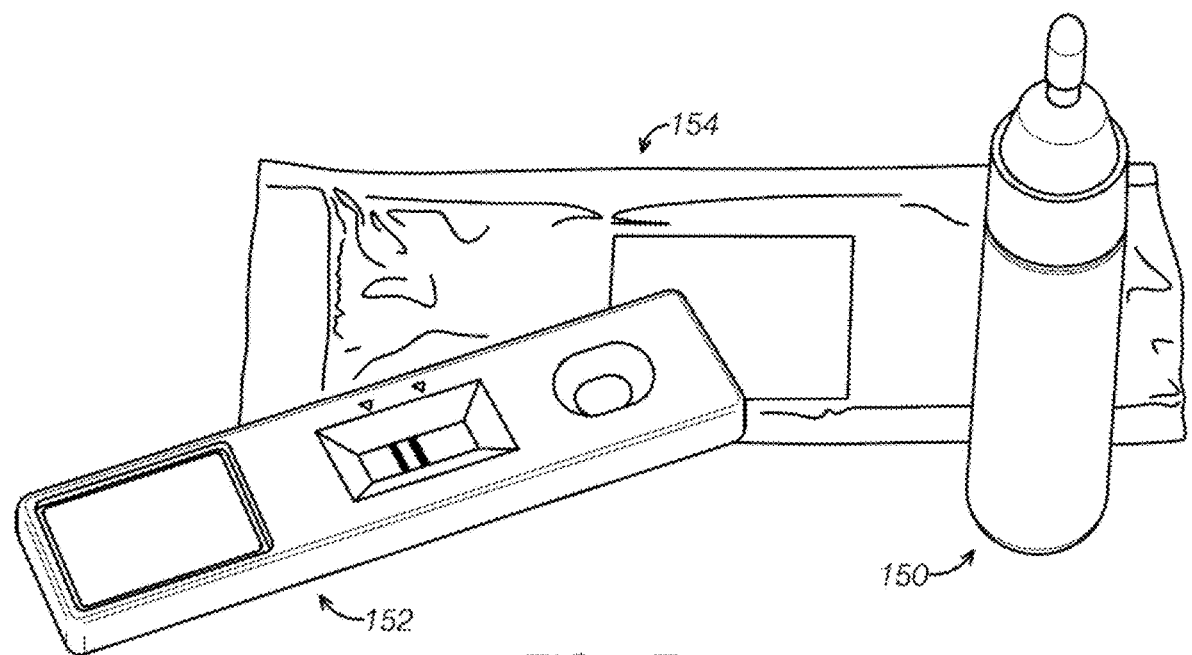
Figure 3F:
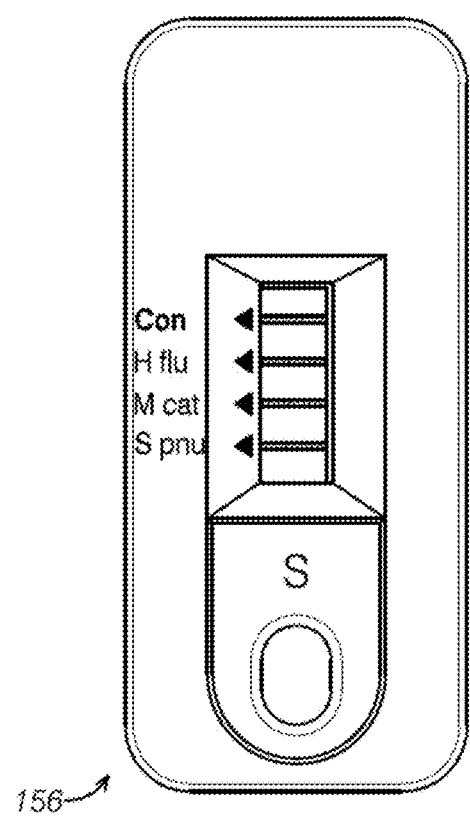

After the sinus fluid has been sampled using the sampling device 110, the sinus fluid sample can be tested. FIG. 3E illustrates an example of a kit that can include a sampling device as described herein. The kit can include a lysis (e.g., buffer or lysis buffer) solution 150, diagnostic test 152, and packaging 154 in addition to the sample collector. As will be described in greater detail below, a sample collector 112 containing a sinus fluid sample can be advanced distally as described herein, and placed in contact with the lysis buffer solution 150 to form the sample solution in which bacterial cells (and particular the *H. influenzae*, *M. catarrhalis* and *S. pneumoniae*) will be lysed to expose markers that can be detected by the assay. Thus, an aliquot of the sample solution can be applied to the diagnostic test 152. The diagnostic test 152 can produce a color change or other indication visible to the medical technician to indicate a positive or negative result for one or more of the bacteria tested (e.g., for sinusitis, *H. influenzae*, *M. catarrhalis* and *S. pneumoniae*). FIG. 3F illustrates an example of a diagnostic test 156 with three different tests (one each for *H. influenzae*, *M. catarrhalis* and *S. pneumoniae*) and a control. FIG. 3F illustrates an example of positive responses to all three different tests and the control. In general, a diagnostic test 152 can contain a plurality of immunoassay tests. The tests can provide rapid results on the order of 1-30 minutes (e.g., 5-20 min, 5-17 min, 5-15 min, etc.). Other configurations can be used for the immunoassay tests, for example multiple testing strips can be included in the diagnostic test 152 with each test strip testing for a different pathogen on each strip, or some variation of a single sequential and one or more parallel assays may be used. In some embodiments the diagnostic test includes tests for two or more pathogens. In some embodiments the diagnostic test includes tests for three or more pathogens. In some embodiments the diagnostic test includes tests for four or more pathogens.

In some embodiments the immunoassay tests can include common conditions implicated in sinusitis, such as strep A, influenza A, and influenza B. In some embodiments the immunoassay tests can include strep A. In some embodiments the immunoassay tests can include influenza A. In some embodiments the immunoassay tests can include influenza B.

In some embodiments the diagnostic tests can include bacterial sinusitis tests. Examples of bacterial sinusitis pathogens include: *Haemophilus influenzae*, *Moraxella catarrhalis*, and *Streptococcus pneumoniae*. Other examples of diagnostic tests that can be used with the devices, kits, and methods disclosed herein include U.S. Patent Publication No. 2014/0314876 to Das et al, titled "Proteomics Based Diagnostic Detection Method for Chronic Sinusitis", the disclosure of which is incorporated by reference herein in its entirety.

The sample collection devices disclosed herein can include a distal tip that is configured to be advanced within the nare of the patient. The distal tip can include a bend that is configured to line up with the anatomy of most patients, such as the middle meatus. In some cases the bend has an angle of about 10 degrees to about 30 degrees relative to a major axis of the device. In some embodiments the distal tip can be flexible. The distal tip can be made out of a soft, biocompatible, and pliable material, such as a polymer. In some embodiments the distal tip can be made out of silicone. Other examples of biocompatible polymers include thermoplastic elastomer (TPE), thermoplastic vulcanizates (TPV), thermoplastic polyolefins (TPO), thermoplastic urethane (TPU) polymers, etc. Specific examples of polymers that can be used for the distal tip also include Kraton, Versaflex, Santoprene, etc. Other biocompatible polymers know by the skilled artisan can also be used. In some embodiments the distal tip can be made out of metal. It may be desirable (though not necessary) to have a material hardness of between about Durometer Shore A90 to D85.

The distal tip can have an open end. In some embodiments the distal tip includes a covered or closed distal end. The covered or closed distal end can be opened with distal advancement of the sample collector. In some embodiments the covering can be designed to be punctured by the sample collector. In some embodiments the covering can be designed to open and close to reduce the chance of contamination of the sample collector. In some embodiments the covering or distal end can be designed to be resealably opened. For example, the cover or distal end can have a patterned opening. The sample collector can be pushed through the patterned opening and the patterned opening can close after the sample collector is retracted. The closed distal end or covering can prevent contamination of the sample collector when the device is advanced through the nare or retracted outside of the patient after the sample has been taken. In some embodiments the distal tip can have an open distal end.

The sample collector can be advanced distally past a distal end of the distal tip to take a sample of sinus fluid or other target fluid. The sample collector can be a swab or contain another absorbent material that can collect and hold fluid. The advancement of the sample collector can be done using an actuator. In some embodiments the actuator can be slider or a plurality of sliders. In some embodiments a handle portion engaged with the sample collector can be used to advance and retract the sample collector. In some embodiments the mucous sample can be collected using negative pressure. For example, the actuator can create a negative pressure in the environment surrounding the distal tip such that the mucous sample flows into the sample collector.

The device can include a safety or lock to reduce the inadvertent advancement of the sample collector while the device is in the nare of the patient. For example, a button or slider can be required to be pressed to allow further advancement of the actuator. In some embodiments the slider itself can be required to be depressed before it can slide. In some cases the safety can be a lock that can be deactivated prior to further advancing the sample collector. In some embodiments the slider can include two sliders that are simultaneously depressed to allow movement of the actuator. In some cases the actuator can move along a track with notches to catch or stop the actuator at the sample position and sample solution position. In some cases the actuator can move along a track with a stair type configuration that requires shifting the actuator at a stop position prior to further advancing or retracting the actuator.

In some embodiments the devices can be operated using a single hand. For example, one portion of the device can be held with one or more fingers while the actuator or proximal end of the device can be held and operated using the thumb. The devices can be configured for ambidextrous use. For example, the device can be ergonomically designed to accommodate use by the left hand and the right hand. The medical professional can use whichever hand they prefer to operate the device. In some embodiments the device can be operated with both hands. For example, the lab technician may prefer to use both hands to extend the sample collector for processing.

The device can include a marker to indicate the orientation of the device, such as the direction of the bend in the distal end. The marker can indicate the lateral direction and/or the left or right nares. The marker can include a colored portion of the device, a label on the device, or a projection on the exterior of the device indicating the orientation of the bend in the distal end.

The device can be used to take a sample from either nostril. The orientation of the entire device can be rotated approximately 180 degrees for use on the other nostril. In some embodiments the device can have a rotatable portion that can be rotated, e.g. by 180 degrees, such that the device can be used for the other nostril. For example, the distal portion of the tip can be rotated relative to the handle of the device.

The device can have a multi-piece construction. The sample collector can be part of a removable handle. In some cases a portion of the handle can be removed prior to being able to expose the sample collector to the sample solution. In some embodiments a portion of the distal cover can be removed to access the sample collector.

The devices described herein can be used with an endoscope to provide additional guidance and visualization to assist the healthcare professional with obtaining a sample from the desired location.

After obtaining the sample the device can be removed from the patient followed by contacting the sample collector with a sample solution. The sample collector can be advanced distally past the distal end to contact the sample collector with the sample solution. In some embodiments the sample collector can be withdrawn proximally through an interior of the device followed by contacting the sample collector with the sample solution. In some embodiments the distal cover can be pulled back to expose the sample collector. In some embodiments the distal cover can have a multi-piece construction such that the cover can be removed to expose the sample collector. In some embodiments a separate slider can be used to advance the sample collector to a sample solution position for contact with the sample solution.

The device can include a depth gauge to provide information to the user regarding the location of the sample collector, such as the distance the sample collector has been advanced.

In some embodiments the device can include a stop or guard configured to engage with the outside of the nose/nostril to prevent further advancement of the device. In some embodiments the stop or guard can be removed by the healthcare worker to provide additional visual guidance and clearance for endoscope The devices can have a naturally retracted position. For example, a compression element could provide a resting force to keep the sample collector in the retracted position. The compression element could pull the sample collector proximally after obtaining the sample in the absence of an actuating force applied by the user.

In some embodiments the hand held device can be configured to be disposable after obtaining a sample fluid from the patient. In some embodiments the hand held devices can be configured to be reusable. For example, the device could be sterilized after obtaining a sample fluid and used for subsequent sample collection from a second patient. In some embodiments the handle can be designed to be reused and a new sample collector or other part can be combined with the handle to form a device for obtaining a sample from a second patient. The sample collector could be provided separately as a single use cartridge to be used with the sterilized handle.

The sample collector can include a structure to facilitate opening and/or closing of a distal cover. For example, fins or a shoulder can be located adjacent to the sample collector to push open the distal cover and to hold the distal cover open during retraction to prevent sample loss caused by the distal cover squeezing the sample collector.

FIGS. 4-14 illustrate aspects of various embodiments of the hand held sample collecting devices disclosed herein.

Figure 4A:
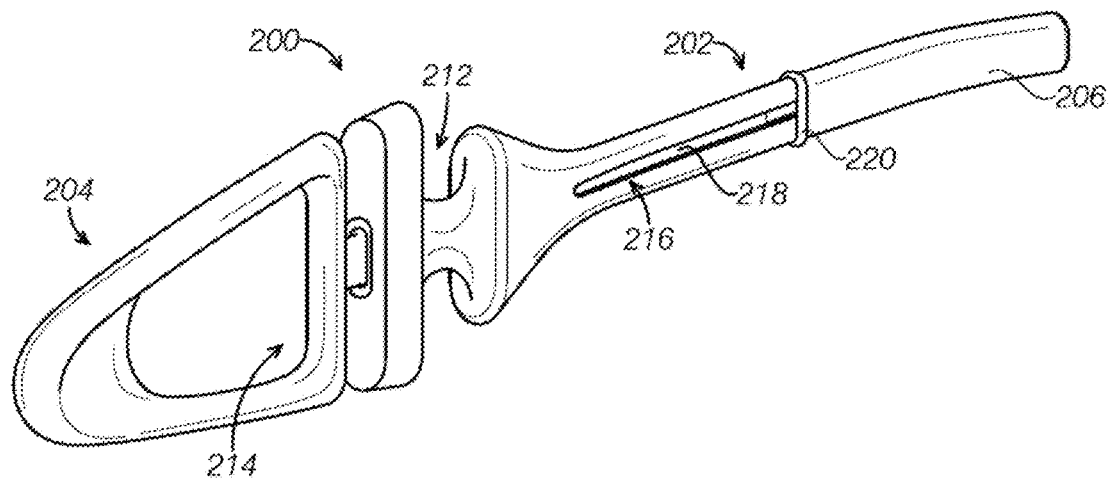
FIGS. 4A-4C illustrate aspects of a device configured to sample a sinus in accordance with some embodiments.
Figure 4B:
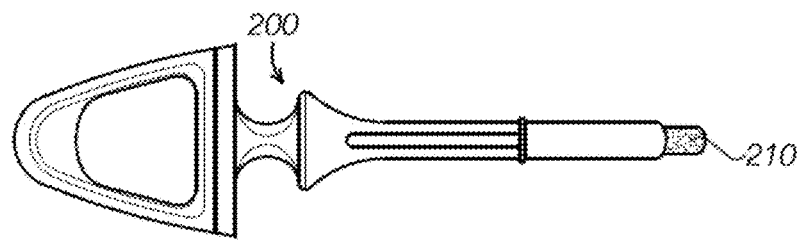
Figure 4C:
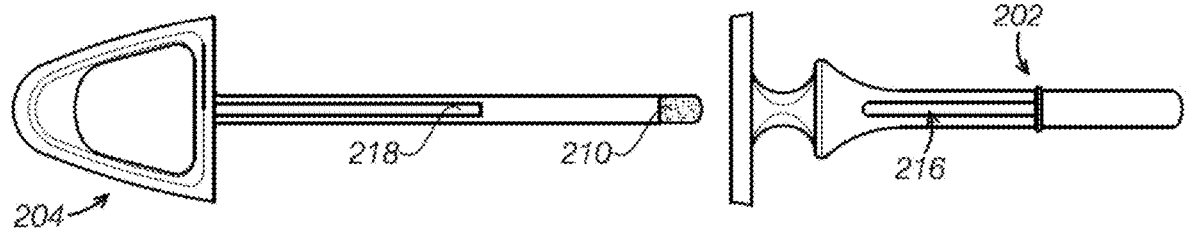

FIGS. 4A-4C illustrate aspects of a device configured to sample a sinus in accordance with some embodiments. FIGS. 4A-4C illustrate a hand held sample collector 200 with a distal section 202 and a proximal section 204. The distal section 202 includes a distal end 206 configured to be introduced through the nares of the patient. The proximal section 204 is configured to slide relative to the distal section 202 to move the sample collector 210, illustrated as a swab, relative to the distal end 206. The device 200 is configured to be gripped with a human hand with a finger grip 212 on the distal portion 202 and a thumb grip 214 on the proximal portion 204. The device 200 can be operated with one hand such that movement of a thumb on the thumb grip 214 can advance the proximal portion 204 relative to the distal portion 202. The device 200 includes an opening or window 216 such that a shaft 218 of the proximal portion 204 can be observed. The window 216 can also be used to provide orientation information to the user, such as the lateral direction of the device. The illustrated device 200 includes a depth gauge 220 aid the operator in determining the position of the sample collector 210. The distal portion 206 can be advanced through the nares to the target location followed by advancing the proximal portion 204 and sample collector 210 relative to the distal portion 206 to contact the sinus fluid. After the sample has been collected, the sample collector 210 is retracted back into the distal portion 206 of the device 200 to shield the sample collector 210 from the sinuses while withdrawing the device 200. After the sample collector 210 has been retracted within the device 200, the device 200 can be removed from the patient. The proximal portion 204 can be retracted proximally relative to the distal portion 202 to completely separate the proximal portion 204 and the distal portion 202 for sample testing as shown in FIG. 4C. The proximal portion 204 and sample collector 210 can be handled for the sample testing and processing. The sample collector 210 with the sinus sample can be tested using the rapid diagnostic testing methods disclosed herein.

Figure 5A:
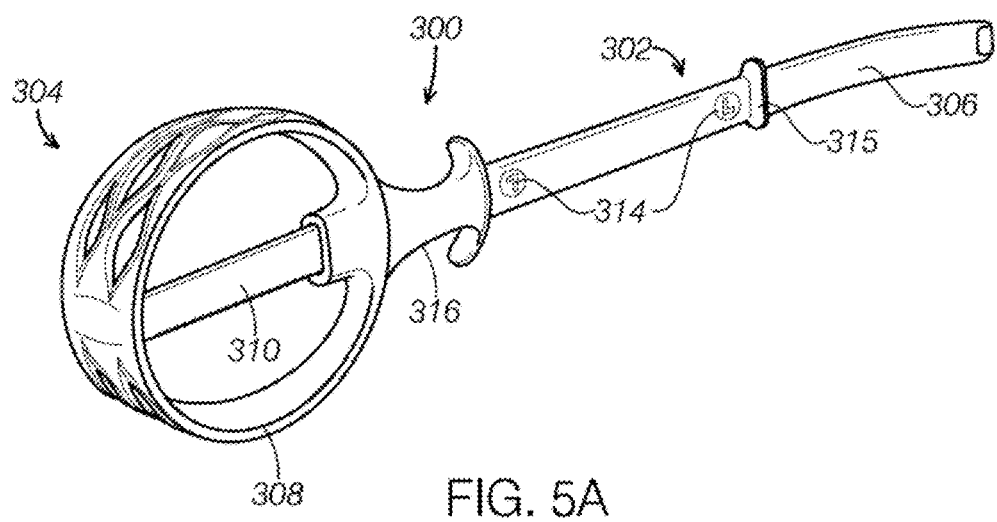
FIGS. 5A-5C illustrate aspects of a device configured to sample a sinus in accordance with some embodiments.
Figure 5B:
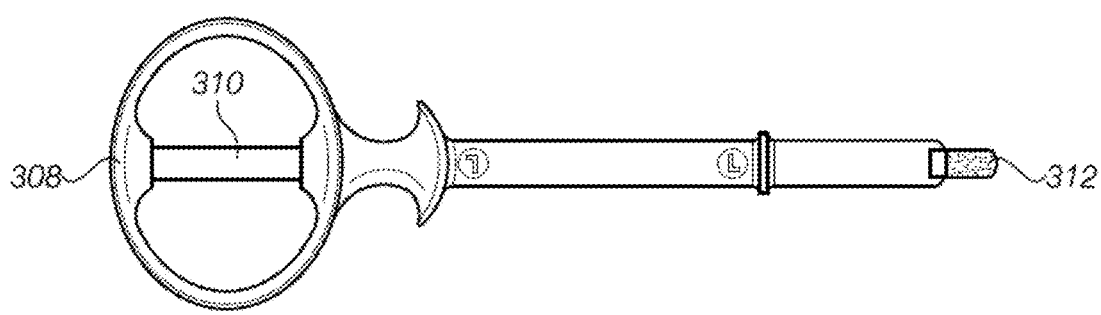
Figure 5C:
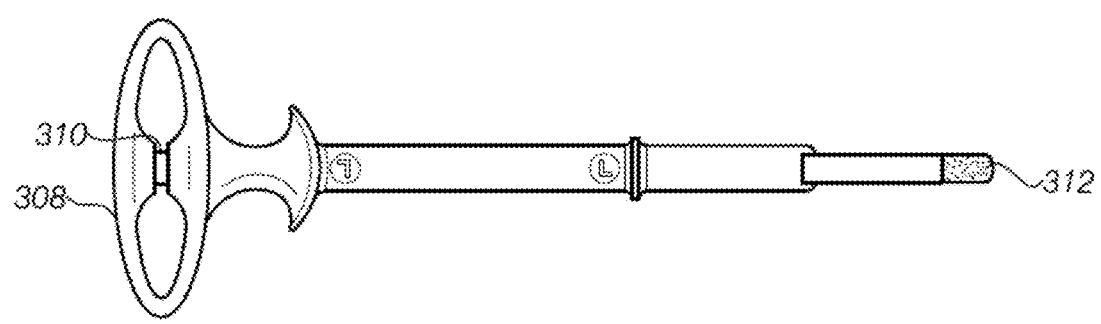

FIGS. 5A-5C illustrate aspects of a device configured to sample a sinus in accordance with some embodiments. FIGS. 5A-5C illustrate a hand held sample collector 300 with a distal section 302 and a proximal section 304. The distal section 302 includes a distal end 306 configured to be introduced through the nares of the patient. A compression/spring element 308 engages with a shaft 310 connected to the sample collector 312. The distal section 302 includes positioning markers 314. The positioning marker 314 can include a marker to provide an orientation of the device to the user, such as the "L" marking on the device 300 indicating the lateral direction. A depth gauge 315 can be included on the distal section 302 to provide depth positioning information to the user. The device 300 can be gripped using the finger grip 316 and compression element 308. The compression element 308 can be pushed forward to advance the shaft 310 and sample collector 312 distally relative to the distal portion 302 as shown in FIG. 5B to retrieve a sample of sinus fluid. The compression element 308 provides a force to retract the sample collector 312 proximally in the absence of a force applied by the user. The compression element 308 can function as an automatic retraction of the sample collector 312 after a sample of sinus fluid has been retrieved. The compression element 308 can be fully pushed forward to contact the sample collector 312 with the sample solution as shown in FIG. 5C. Pushing the sample collector 312 distally out of the device can minimize losses of the collected sinus fluid.

Figure 6A:
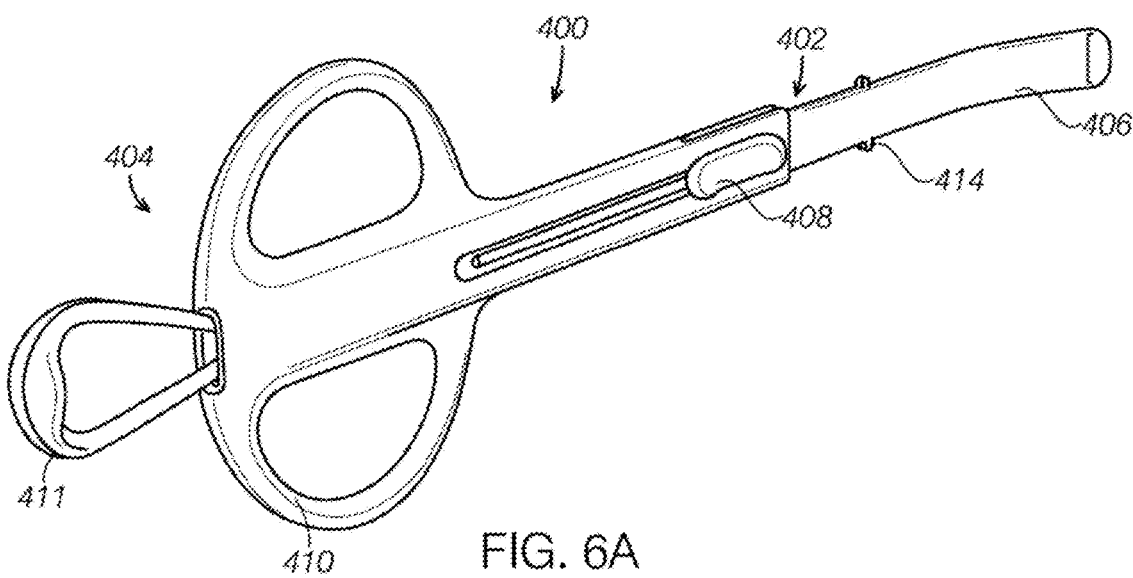
FIGS. 6A-6C illustrate aspects of a device configured to sample a sinus in accordance with some embodiments.
Figure 6B:
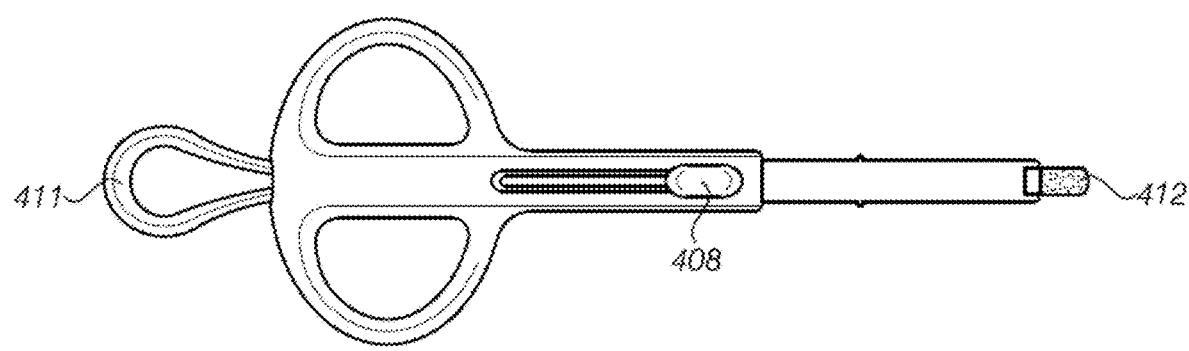
Figure 6C:
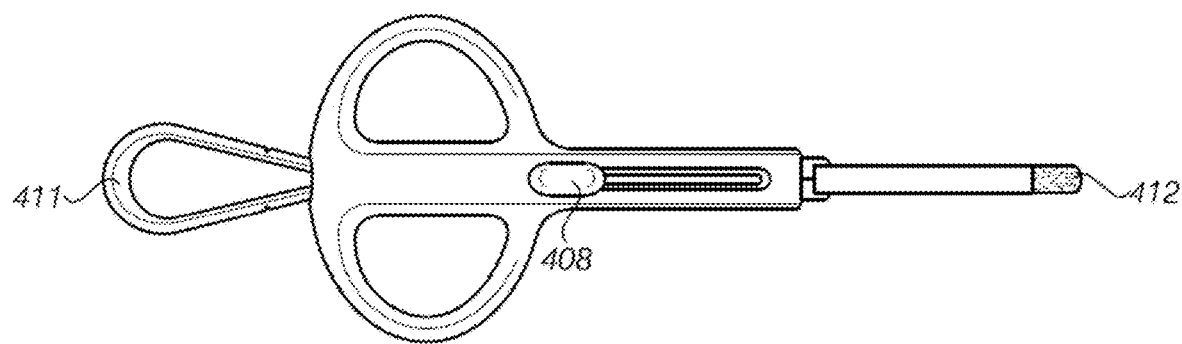

FIGS. 6A-6C illustrate aspects of a device configured to sample a sinus in accordance with some embodiments. FIGS. 6A-6C illustrate a hand held sample collector 400 with a distal section 402 and a proximal section 404. The distal section 402 includes a distal end 406 configured to be introduced through the nares of the patient. The distal end 406 can be advanced and retracted by an actuator, such as the slider 408. The slider 408 can slide along the body of the proximal section 404. The proximal section 404 includes a finger grip 410 and a thumb grip 411. The thumb grip 411 can pushed to advance the sample collector 412 as illustrated in FIG. 6B. The thumb grip 411 can retract in the absence of an applied force to retract the sample collector back within the distal portion 406. The slider 408 can further retract the distal end 406 to expose the sample collector 412 as shown in FIG. 6C for contact with a sample solution while minimizing sample loss. The slider 408 can provide orientation of the distal end 406 to the user. For example, the distal end can be curved in the same direction/side as the location of the slider as shown in device 400. The bumps 414 on the distal portion 406 can function as a depth gauge to provide additional positioning and orientation information to the user.

Figure 7A:
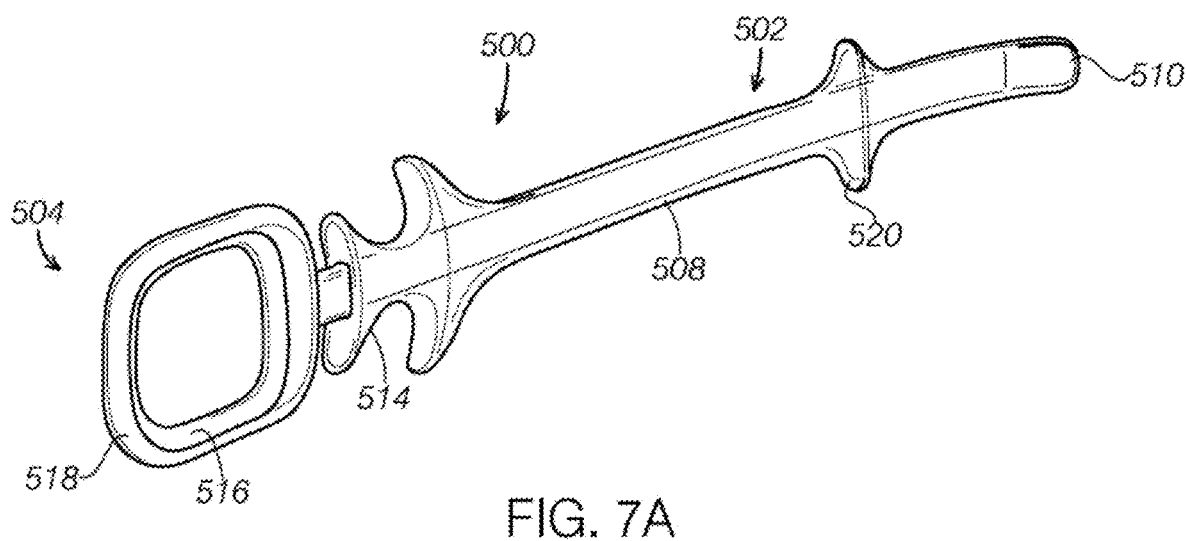
FIGS. 7A-7C illustrate aspects of a device configured to sample a sinus in accordance with some embodiments.
Figure 7B:
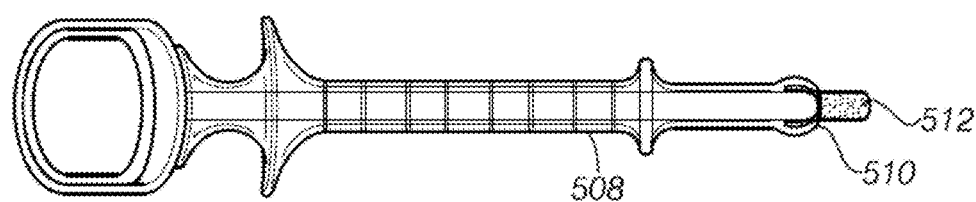
Figure 7C:
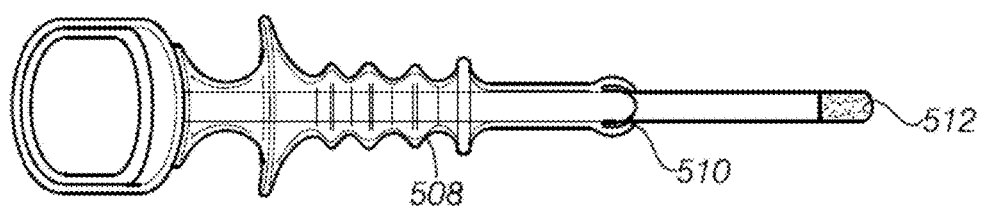

FIGS. 7A-7C illustrate aspects of a device configured to sample sinus fluid in accordance with some embodiments. The hand held sample collector 500 includes a distal section 502 and a proximal section 504. The distal section 502 includes a distal end 506 with an outer covering 508 having a patterned cut distal end section 510 that allows the sample collector 512 to advance distally past the covering 508. The covering 508 can be made out of a flexible and biocompatible material such as silicone. The device 500 includes a finger grip 514 and thumb grip 516. The thumb grip 516 can be advanced to push the sample collector 512 distally past the covering 508 as shown in FIG. 7B. The sample collector 512 advances past the patterned cut distal end section 510 to contact the sinus fluid. The sample collector 512 can be retracted and covered while removing the device from the user to prevent contaminating the sample collector with mucous from areas besides the targeted sinus fluid. The thumb grip 516 can include markings or a colored section 518 to provide orientation information to the user, such as the direction of the bend in the distal section 502. The ridge 520 on the distal section 502 can function as a depth gauge to provide additional positioning and orientation information to the user. The covering 508 can be pulled back to expose the sample collector 512 to the sample solution as shown in FIG. 7C. The covering 508 can be patterned or scored to fold back as it is pulled back away from the sample collector 512. Retracting the covering 508 relative to the sample collector 512 can help minimize the sample loss from the sample collector 512.

Figure 8A:
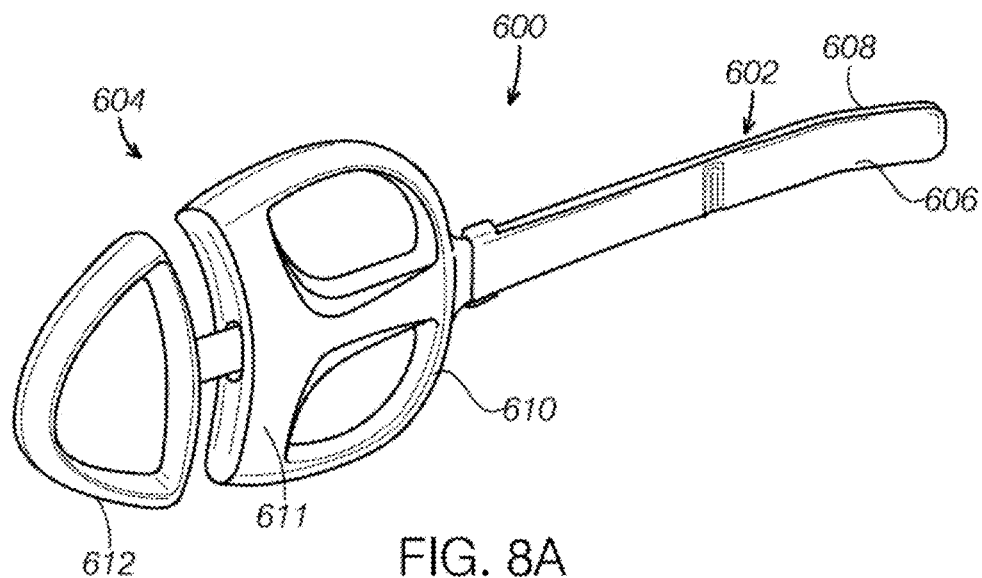
FIGS. 8A-8C illustrate aspects of a device configured to sample a sinus in accordance with some embodiments.
Figure 8B:
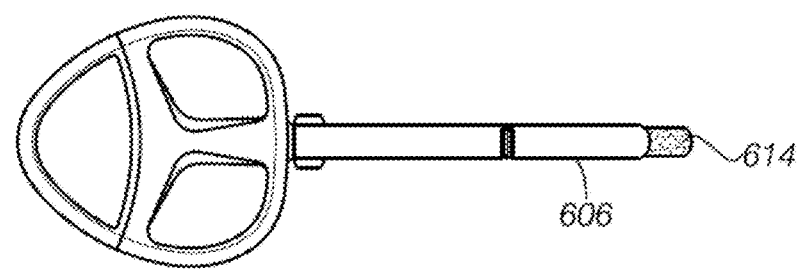
Figure 8C:
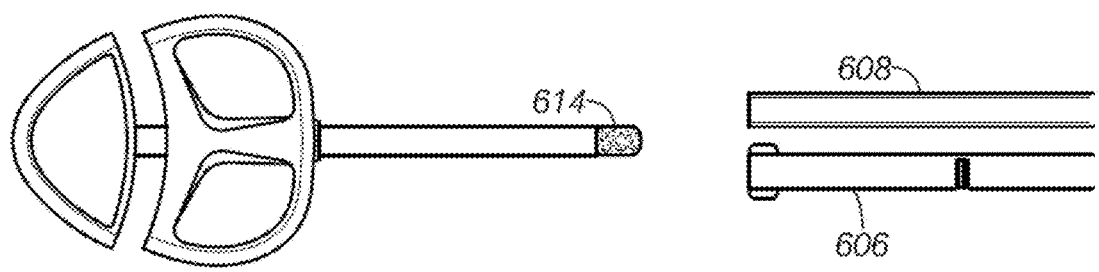

FIGS. 8A-8C illustrate aspects of a device configured to sample a sinus in accordance with some embodiments. The hand held sample collector 600 includes a distal section 602 and a proximal section 604. The distal section has a two piece construction with a first distal sleeve portion 606 and second distal sleeve portion 608. The proximal section 604 includes a finger grip section 610 and a thumb grip 612. The finger grip section 610 includes a marking 611 to label the lateral side of the device to let the user know the orientation of the bend in the distal section 602 of the device 600. The thumb grip 612 can be pushed distally to expose the sample collector 614 to collect a sample of sinus fluid as shown in FIG. 8B. The thumb grip 612 can be retracted to retract the sample collector 614 having the sinus fluid sample back within the distal section 602 prior to removing the device 600 from the patient to avoid contaminating the collected sample. The sample collector 614 can be processed after the device 600 is removed from the patient. The sample collector 614 can be exposed to the sample solution by removing the first distal sleeve portion 606 and second distal sleeve portion 608 as shown in FIG. 8C.

Figure 9A:
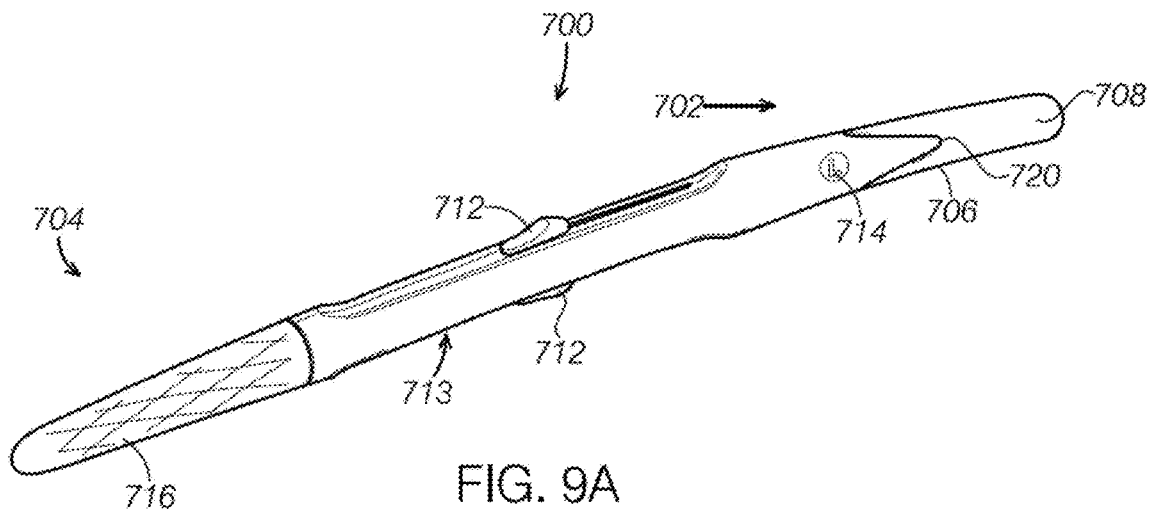
FIGS. 9A-9C illustrate aspects of a device configured to sample a sinus in accordance with some embodiments.
Figure 9B:
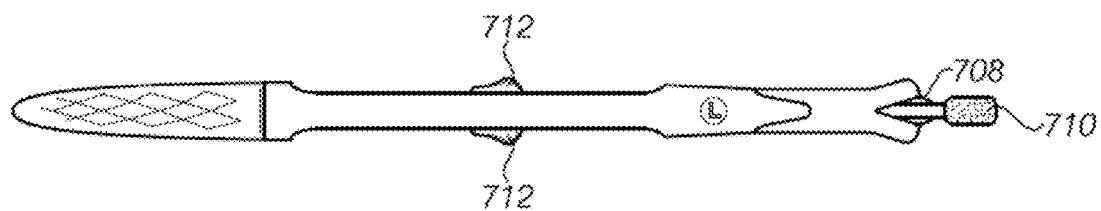
Figure 9C:

FIGS. 9A-9C illustrate aspects of a device configured to sample a sinus in accordance with some embodiments. The hand held device 700 has a pen type shape with a distal section 702 and a proximal section 704. The distal section 702 includes a distal tip 706 with a patterned opening 708. The sample collector 710 can be advanced past the patterned opening by advancing the slider 712. The device 700 includes two sliders 712 on a central portion 713 of the device. The body of the device 700 can include a marker 714 to provide information on the orientation of the device to the user, such as the direction of the bend of the distal section 702. The device 700 can include a handle 716 on the proximal section 704. The device 700 can be gripped by the user using the thumb and middle finger. The slider 712 can have multiple positions. A retracted position is shown in FIG. 9A. A partially advanced slider 712 position is shown in FIG. 9B with the sample collector 710 advanced distally past the patterned opening 708. The slider 712 can be advanced further to expose the sample collector 710 to the sample solution as shown in FIG. 9C. The slider 712 has a retracted position, sample position, and testing position. The device 700 can include a lock at each of the retracted position, sample position, and testing position. The slider 712 can be configured such that both sliders 712 are pushed to allow movement of the slider 712. The device 700 can be used for either nostril by rotating by 180 degrees. The distal tip 706 can be made out of a soft polymer material like silicone to be comfortable for the patient. The shape of the engagement 720 between the distal tip 702 with a handle portion can be contoured as shown in FIGS. 9A-9C such that the contour of the engagement 720 can provide depth and orientation information to the user of the device. The patterned opening 708 can open like an alligator jaw to protect the sample collector 710 from being contaminated by nasal mucous or bacterial or cross contamination while the device is advanced in the nostril or retracted from the nostril after sampling. The device can include a shoulder or fin 718 adjacent to the sample collector 710 to facilitate opening of patterned opening 708. The shoulder or fin 718 can push open the patterned opening 708 and also assist with pushing open and holding open the patterned opening 708 when the sample collector 710 is retracted to minimize sample loss.

Figure 10A:
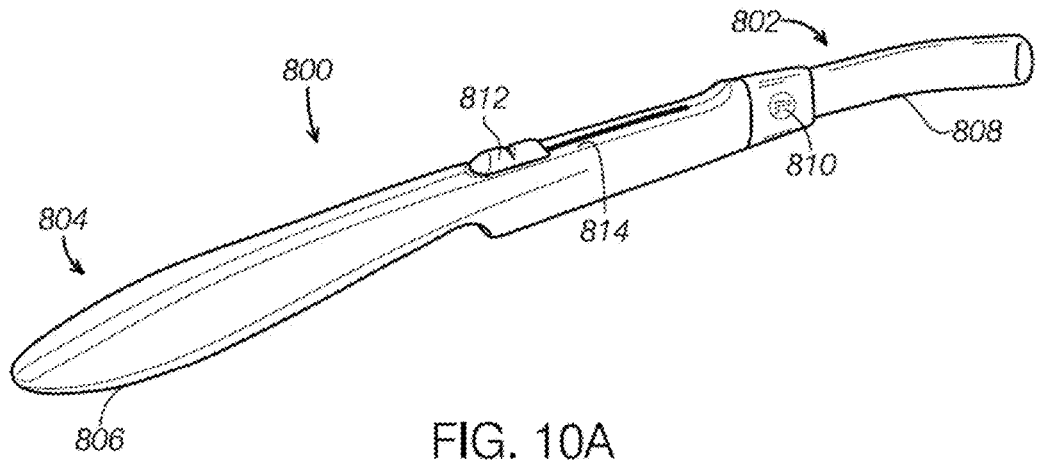
FIGS. 10A-10D illustrate aspects of a device configured to sample a sinus in accordance with some embodiments.
Figure 10B:
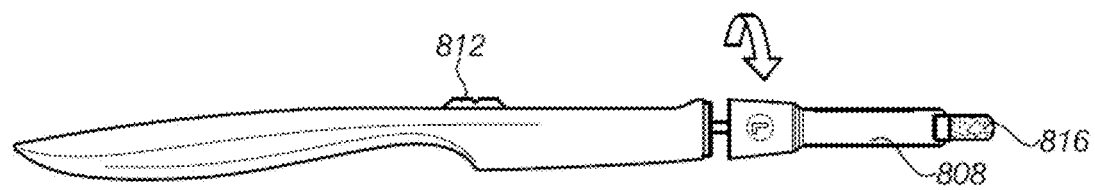
Figure 10C:
Figure 10D:
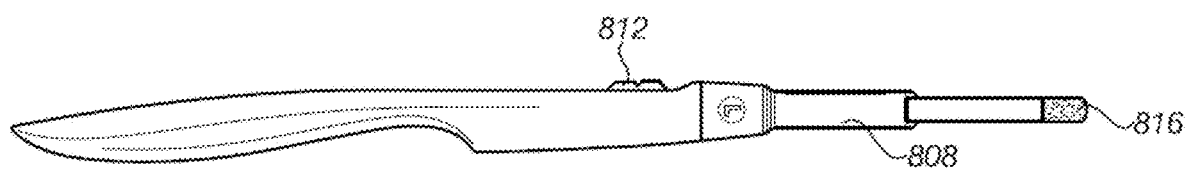

FIGS. 10A-10D illustrate aspects of a device configured to sample a sinus in accordance with some embodiments. The hand held device 800 has a distal section 802 and proximal section 804. The proximal section 804 includes a handle 806 with a slider 812. The distal section 802 includes a distal portion 808. The distal portion 808 includes an orientation marker 810 to display the orientation of the bend in the distal portion 808. The distal portion 808 can be rotated 180° relative to the handle 806 so that the device 800 can be used for either nostril. The distal portion 808 can be made out of a soft material such as silicone to improve patient comfort. The slider 812 can be advanced to the sample mark 814 to distally advance the sample collector 816 past the distal portion 808 as shown in FIG. 10C. The sample collector 816 can be further advanced using the slider 812 as shown in FIG. 10D to contact the sample solution.

Figure 11A:
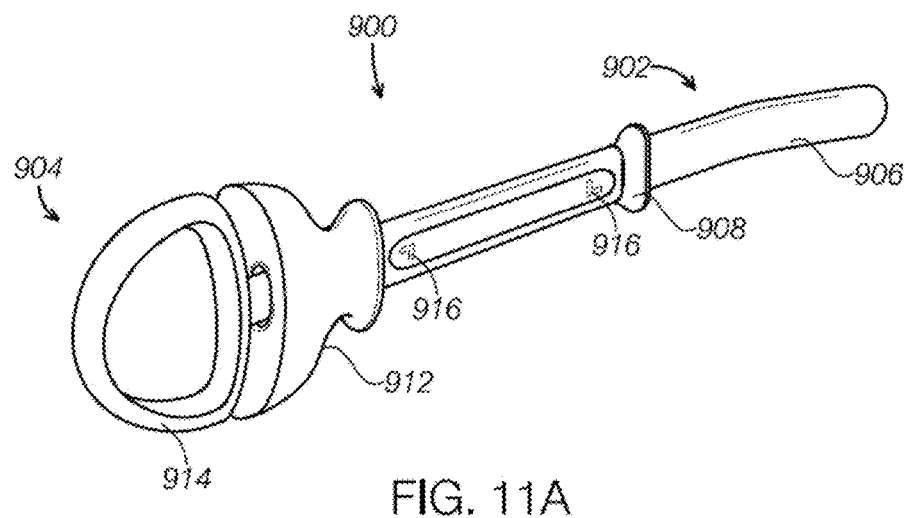
FIGS. 11A-11C illustrate aspects of a device configured to sample a sinus in accordance with some embodiments.
Figure 11B:
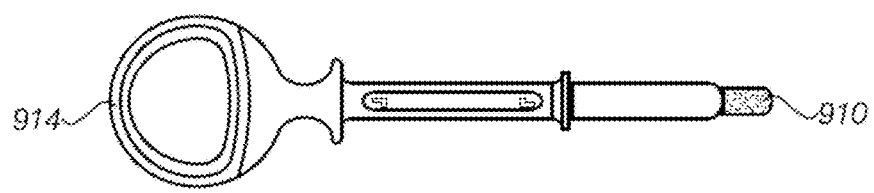
Figure 11C:
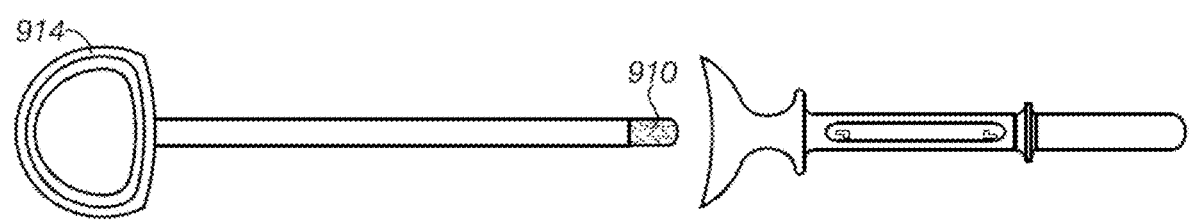

FIGS. 11A-11C illustrate aspects of a device configured to sample a sinus in accordance with some embodiments. FIGS. 11A-11C illustrate a hand held sample collector 900 with a distal section 902 and a proximal section 904. The distal section 902 includes a distal end 906 configured to be introduced through the nares of the patient. The proximal section 904 is configured to slide relative to the distal section 902 to move the sample collector 910, illustrated as a swab, relative to the distal end 906. The device 900 is configured to be gripped with a human hand with a finger grip 912 on the distal portion 902 and a thumb grip 914 on the proximal portion 904. The device 900 includes a marking 916 to indicate the orientation of the bend in the distal end 906. The device can include a collar 908 to prevent further advancement of the distal end 906 after it has been inserted in the nares. The device 900 can be operated with one hand such that movement of a thumb on the thumb grip 914 can advance the proximal portion 904 relative to the distal portion 902. The distal end 906 can be advanced through the nares to the target location followed by advancing the proximal portion 904 and sample collector 910 relative to the distal portion 906 to contact the sinus fluid as shown in FIG. 11B. After the sample has been collected the device 900 can be removed from the patient and the proximal portion 904 can be retracted proximally relative to the distal portion 902 to completely separate the proximal portion 904 and the distal portion 902 as shown in FIG. 11C. The sample collector 910 with the sinus sample can be tested using the rapid diagnostic testing methods disclosed herein.

Figure 12A:
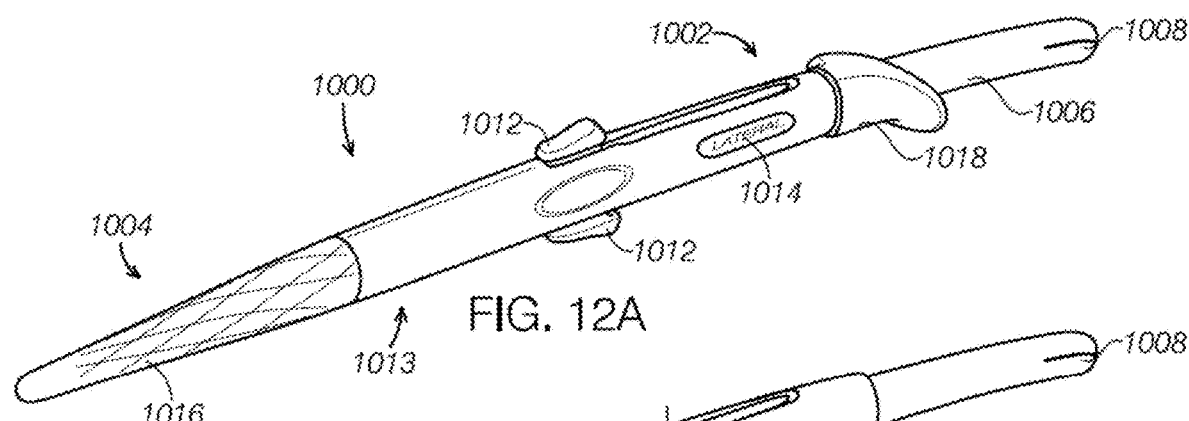
FIGS. 12A-12E illustrate aspects of a device configured to sample a sinus in accordance with some embodiments.
Figure 12B:
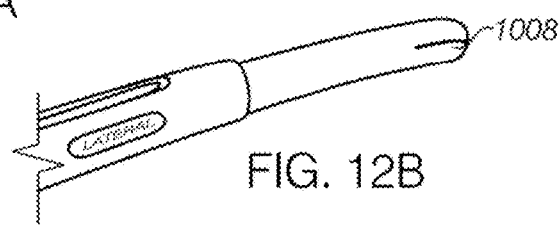

FIGS. 12A-12E illustrate aspects of a device configured to sample a sinus in accordance with some embodiments. The hand held device 1000 has a pen type shape with a distal section 1002 and a proximal section 1004. The distal section 1002 includes a distal tip 1006 with a patterned opening 1008. The sample collector 1010 can be advanced past the patterned opening by advancing the slider 1012. The device 1000 includes two sliders 1012 on a central portion 1013 of the device. The body of the device 1000 can include a removable depth gauge 1018. The depth gauge 1018 can be rotated 90 degrees to a major axis of the device 1000 to maximize visualization of the nasal cavity. FIG. 12B illustrates the device 1000 with the depth gauge 1018 removed. The body of the device 1000 can include a marker 1014 to provide information on the orientation of the device to the user, such as the direction of the bend of the distal section 1002. The device 1000 can include a handle 1016 on the proximal section 1004. The device 1000 can be gripped by the user using the thumb and middle finger.

Figure 12C:
Figure 12D:
Figure 12E:
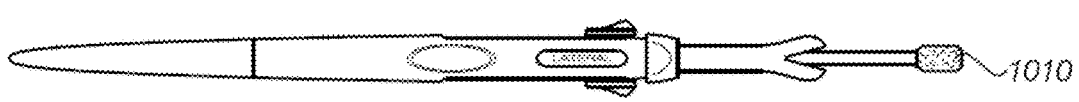

The slider 1012 can have multiple positions. A retracted position is shown in FIGS. 12A and 12C. A partially advanced slider 1012 position is shown in FIG. 12D with the sample collector 1010 advanced distally past the patterned opening 1008. The slider 1012 can be advanced further to expose the sample collector 1010 to the sample solution as shown in FIG. 12E. Thus the slider 1012 has a retracted position, sample position, and testing position. The device 1000 can include a lock at each of the retracted position, sample position, and testing position. The slider 1002 can be configured such that both sliders 1012 are pushed to allow movement of the slider 1012. The device 1000 can be used for either nostril by rotating by 180 degrees. The distal tip 1006 can be made out of a soft polymer material like silicone to be comfortable for the patient. The patterned opening 1008 can open like an alligator jaw to protect the sample collector 1010 from being contaminated by nasal mucus or bacterial or cross contamination while the device is advanced in the nostril or retracted from the nostril after sampling. The device can include a depth gauge 1018 adjacent to the sample collector 1010. The device 1000 can optionally include a safety that makes it difficult to accidentally fully push the sample collector past the sample configuration (FIG. 12D) while the device is deployed in the patient. The device 1000 can allow for improved endoscopic camera access for the user. For example, the depth gauge 1018 can be removed to improve clearance for a camera or for visualization as shown in FIG. 10B.

Figure 13A:
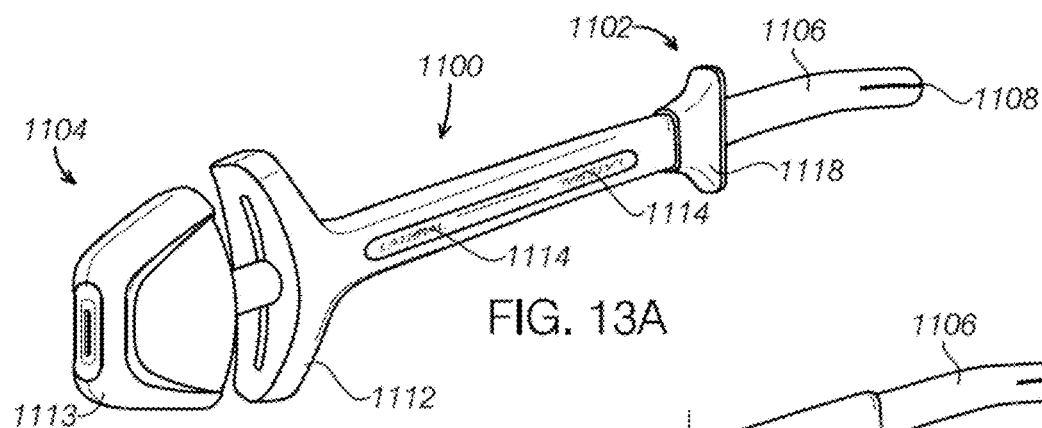
FIGS. 13A-13E illustrate aspects of a device configured to sample a sinus in accordance with some embodiments.
Figure 13B:
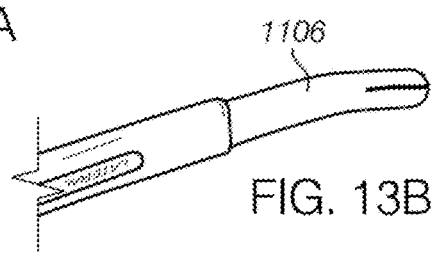
Figure 13C:
Figure 13D:
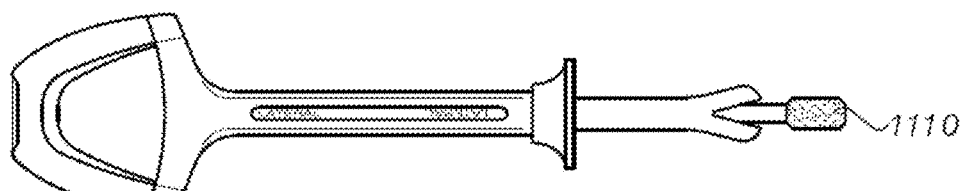
Figure 13E:
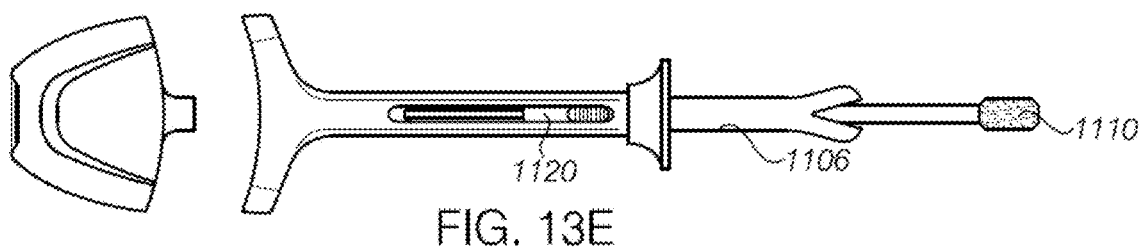
Figure 15A:
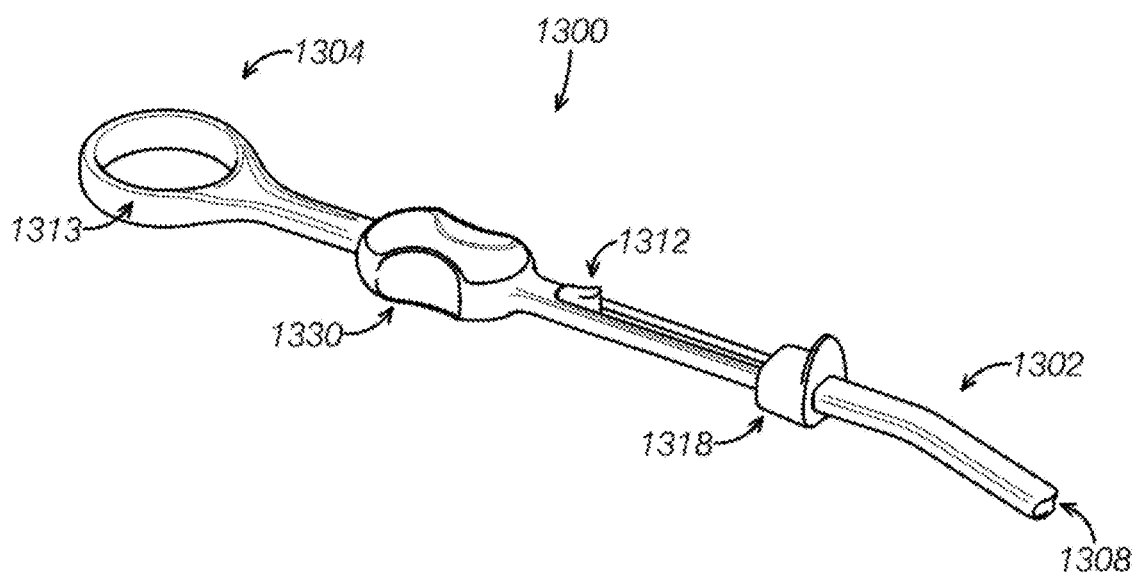
FIG. 15A is a rendering of the lateral side of another variation of a device configured to sample from a sinus.
Figure 15B:
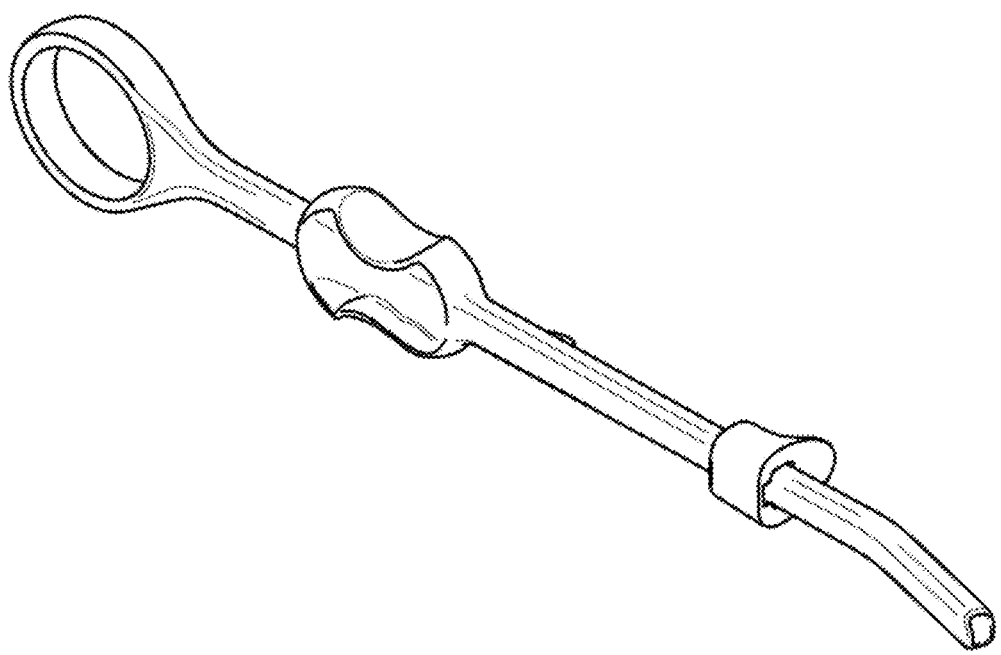
FIG. 15B is a rendering of the posterior side of the assembled device of FIG. 15A.
Figure 15C:
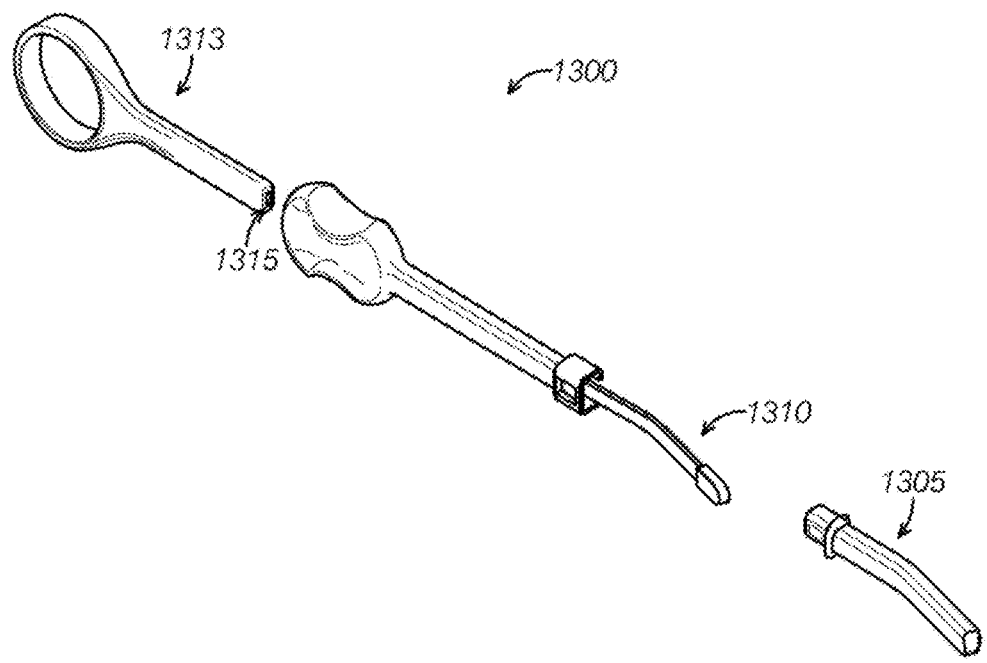
FIGS. 15C and 15D show partially exploded views of the lateral side and front of the device of FIG. 15A.
Figure 15D:
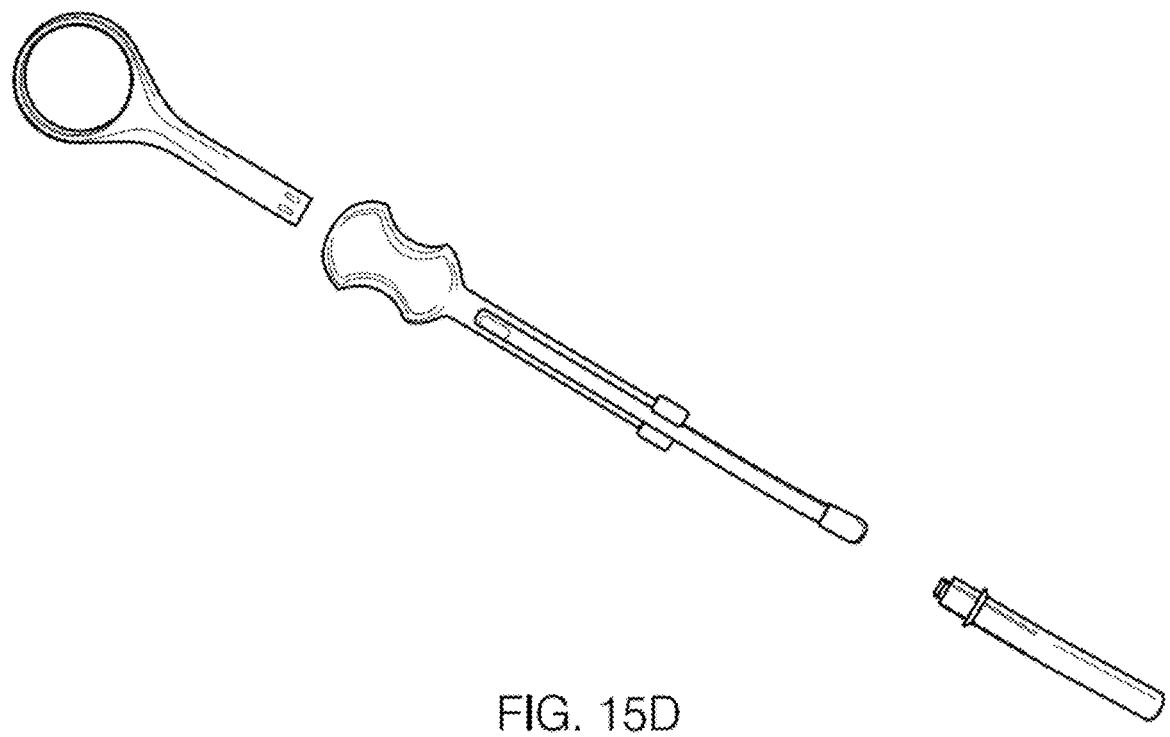

FIGS. 13A-13E illustrate aspects of a device configured to sample a sinus in accordance with some embodiments. The hand held device 1100 has a distal section 1102 and a proximal section 1104. The distal section 1102 includes a distal tip 1106 with a patterned opening 1108. The sample collector 1110 can be advanced past the patterned opening by advancing the handle 1113. The body of the device 1100 can include a removable depth gauge 1118. FIG. 13B illustrates the device 1100 with the depth gauge 1118 removed. The different appearance of the body of the device 1100 and the distal section 1102 can also provide depth and orientation information to the user. The body of the device 1100 can include a marker 1114 to provide information on the orientation of the device to the user, such as the direction of the bend of the distal section 1102. The device can be held by the handle 1113 and finger grips 1112. A retracted position is shown in FIGS. 13A and 13C. An advanced handle 1113 position is shown in FIG. 13D with the sample collector 1110 advanced distally past the patterned opening 1108. The handle 1113 can be removed as shown in FIG. 13E. The bottom side of the device 1100 includes a slider 1120 configured to advance the sample collector 1110 to contact the sample solution as shown in FIG. 13E. The device 1100 can be used for either nostril by rotating by 180 degrees. The device 1100 can optionally include a safety that makes it difficult to accidentally fully push the sample collector past the sample configuration while the device is deployed in the patient. The device 1100 can allow for improved endoscopic camera access for the user.

FIGS. 14A-14E illustrate aspects of a device configured to sample a sinus in accordance with some embodiments. The hand held device 1200 has a distal section 1202 and a proximal section 1204. The distal section 1202 includes a distal tip 1206 with a patterned opening 1208. The sample collector 1210 can be advanced past the patterned opening 1208 by advancing the handle 1213. The handle 1213 can be advanced and retracted by the user's thumb. The body of the device 1200 can include a removable depth gauge 1218. FIG. 14B illustrates the device 1200 with the depth gauge 1218 removed. The different appearance of the body of the device 1200 and the distal section 1202 can also provide depth and orientation information to the user. The body of the device 1200 can include a marker 1214 to provide information on the orientation of the device to the user, such as the direction of the bend of the distal section 1202. The device can be held by the handle 1213 and finger grips 1212. A retracted position is shown in FIGS. 14A and 14C. An advanced handle 1213 position is shown in FIG. 14D with the sample collector 1210 advanced distally past the patterned opening 1208. The handle 1213 can be removed as shown in FIG. 14E. The bottom side of the device 1200 includes a slider 1220 configured to advance the sample collector 1210 to contact the sample solution as shown in FIG. 14E. In some embodiments the handle 1213 can be configured such that it has to be removed prior to being able to advance the slider. The device 1200 can be used for either nostril by rotating by 180 degrees. The device 1200 can optionally include a safety that makes it difficult to accidentally fully push the sample collector past the sample configuration while the device is deployed in the patient. The device 1200 can allow for improved endoscopic camera access for the user.

FIGS. 15A-21 illustrates devices configured to sample a sinus in accordance with some embodiments. For example, in FIGS. 15A-15D, hand held device 1300 has a distal section 1302 and a proximal section 1304. Hand held device 1300 includes a sample collector 1310 housed within a sleeve 1305 with a sleeve opening 1307, a main body 1330, a (thumb ring) handle 1313 and a depth stop 1318. Sleeve 1305 couples to main body 1330 via a couplers, 1332. Couplers 1332 can have a double tip lock feature as shown in FIG. 17A or a single locking tip feature as shown in FIG. 17B.

Figure 16:
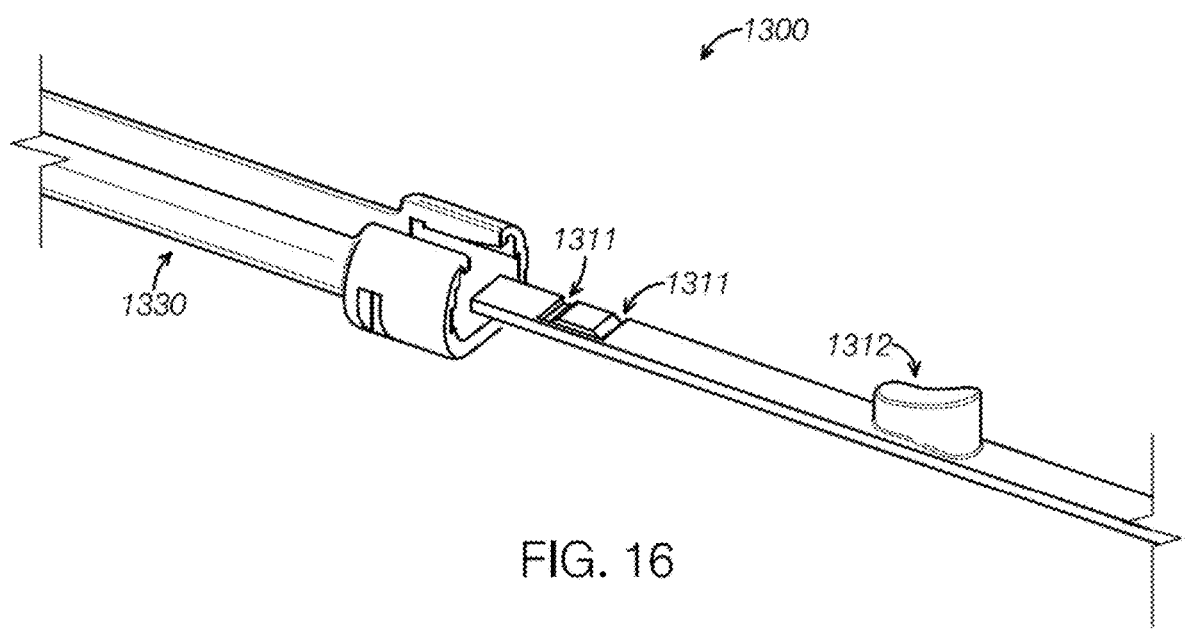
FIG. 16 is an example of a proximal end of a sample collector being inserted into a distal end of the main body portion.
Figure 21:
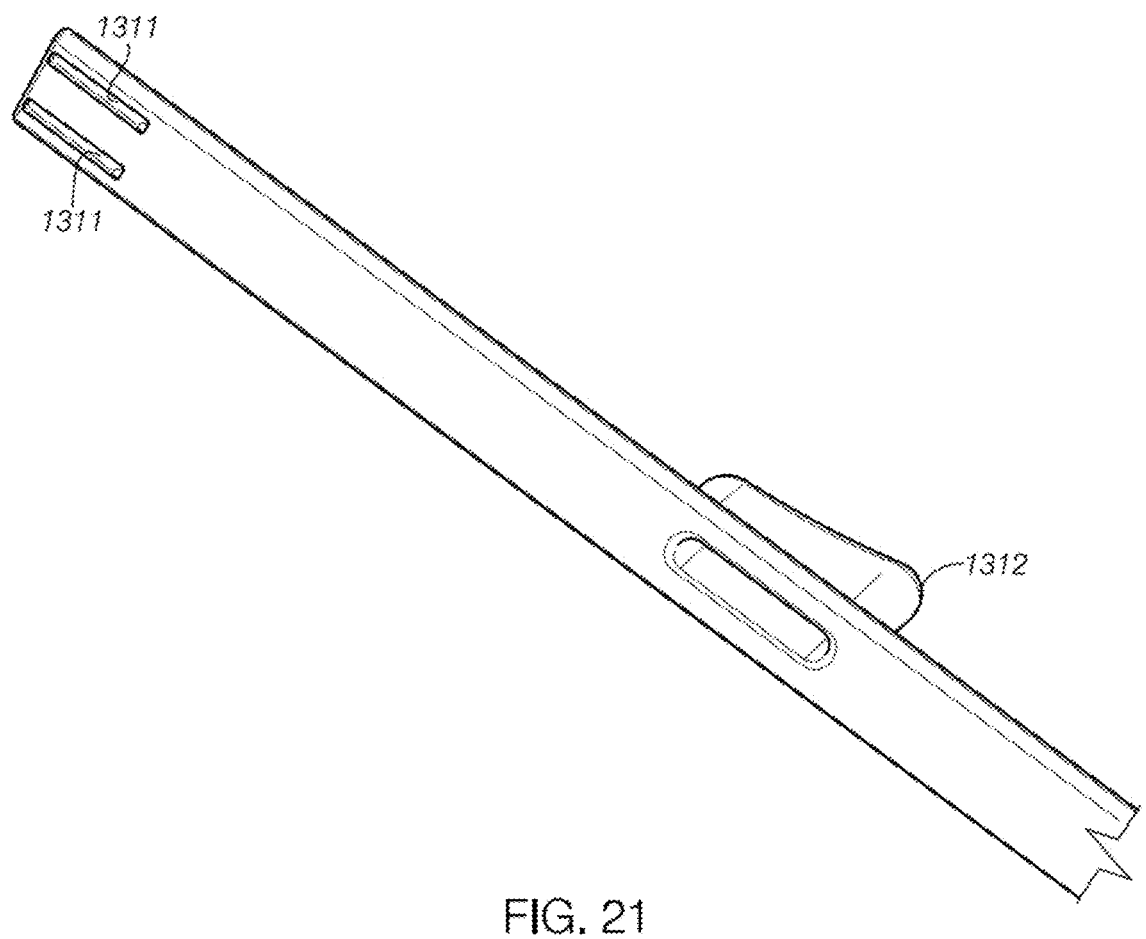
FIG. 21 illustrates a proximal end region of a sample collector that couples with the handle.

Sample collector 1310 (e.g., swab) can be advanced past sleeve opening 1307 by the ring handle 1313, which may be configured to extend the sample collector a predetermined distance from the distal end. This first predetermined distance is configured to extend into the correct sample region (e.g., the sinus, such as the middle meatus or maxillary sinus), while avoiding regions distal to these regions which may otherwise contaminate the sample. Handle ring 1313 includes a connector (shown as a handle ring cavity) 1315 that is able to engage a proximal end of the sample collector 1310 while both elements are retained within main body 1330. Sample collector includes at least one notch 1311 for coupling to handle ring 1313 as shown in FIG. 16. FIG. 21 shows an alternative design for coupling sample collector 1310 with handle 1313, which includes one or more notch 1311 (two are shown in this example) that is vertically arranged and parallel to the longitudinal axis of sample collector 1310. Sample collector 1310 can be advanced past sleeve opening 1307 the first predetermined distance (e.g., between 5 and 20 mm (e.g., between 7 mm and 15 mm, between 8 mm and 12 mm, etc.) by advancing handle 1313. Handle 1313 can be advanced and retracted by the user's thumb. Having the handle 1313 limited to only advancing the sample collector 1310 the first predetermined distance from sleeve opening 1307 may prevent a longer portion of sample collector 1310 from being extended further into the sinus of the subject and causing discomfort and pain, and/or contamination. Once a sample has been collected on sample collector 1310, sample collector 1310 may be retracted within sleeve 1305, and device 1300 removed from subject's sinus and nasal cavity, the sample can be processed for assaying.

Figure 18A:
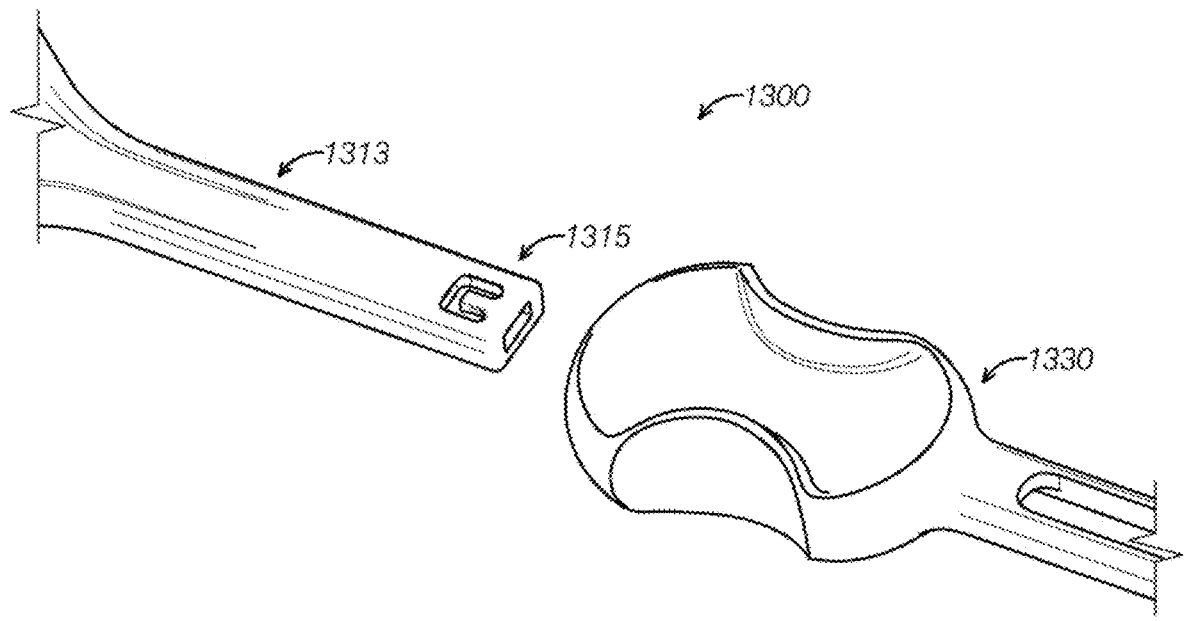
FIG. 18A shows an exploded view of one variation of a distal end of a handle and a proximal end of a main body region.
Figure 18B:
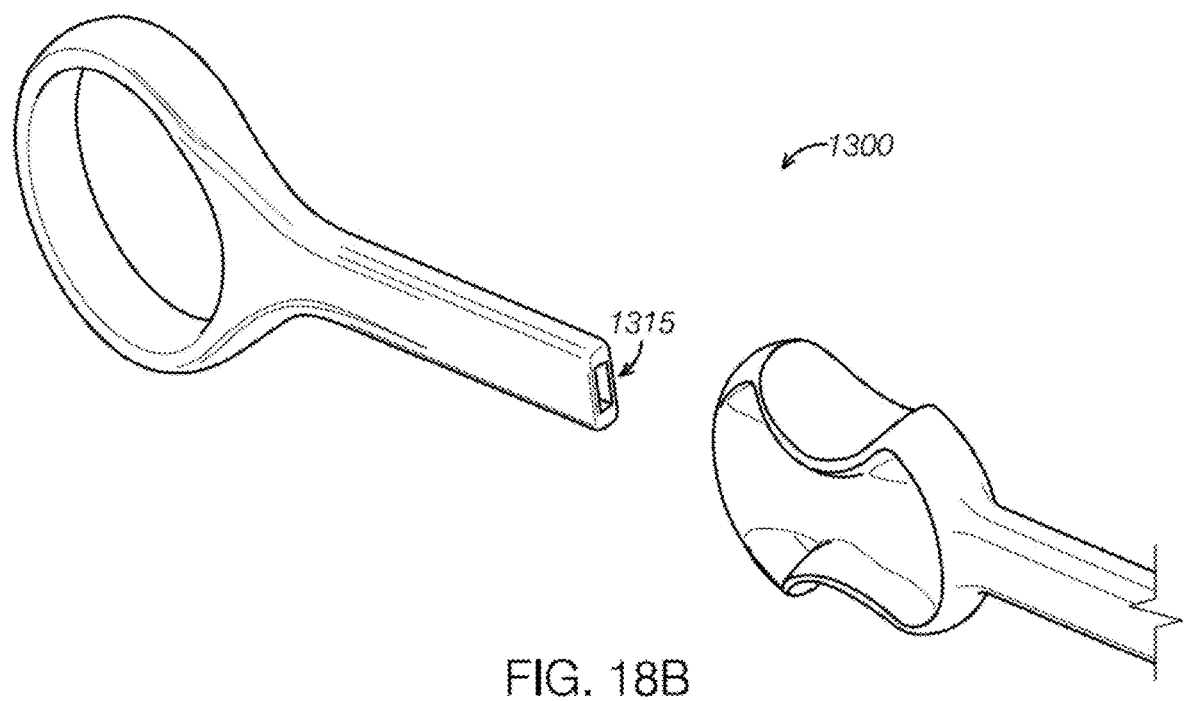
FIG. 18B illustrates a distal end of a thumb ring that is separated from a proximal end of a main body region of the device, similar to the view of FIG. 18A. The thumb ring controller region at the distal end (left side of FIGS. 18A and 18B) may be coupled into the distal end of the main body region.
Figure 19:
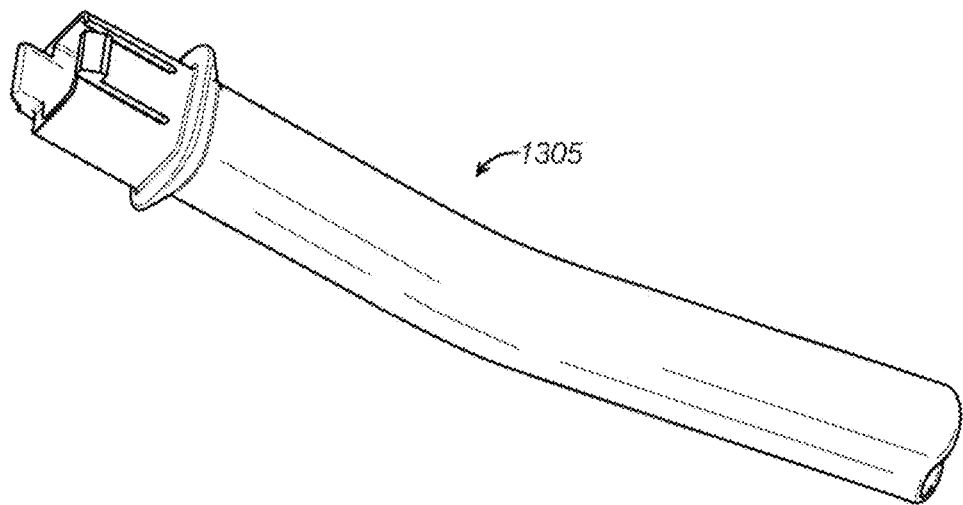
FIG. 19 illustrates a sleeve for housing the distal end of the swab. Both the sleeve (protective cover) and the sample collector (including swab) are bent in a predefined manner as described herein.
Figure 20:
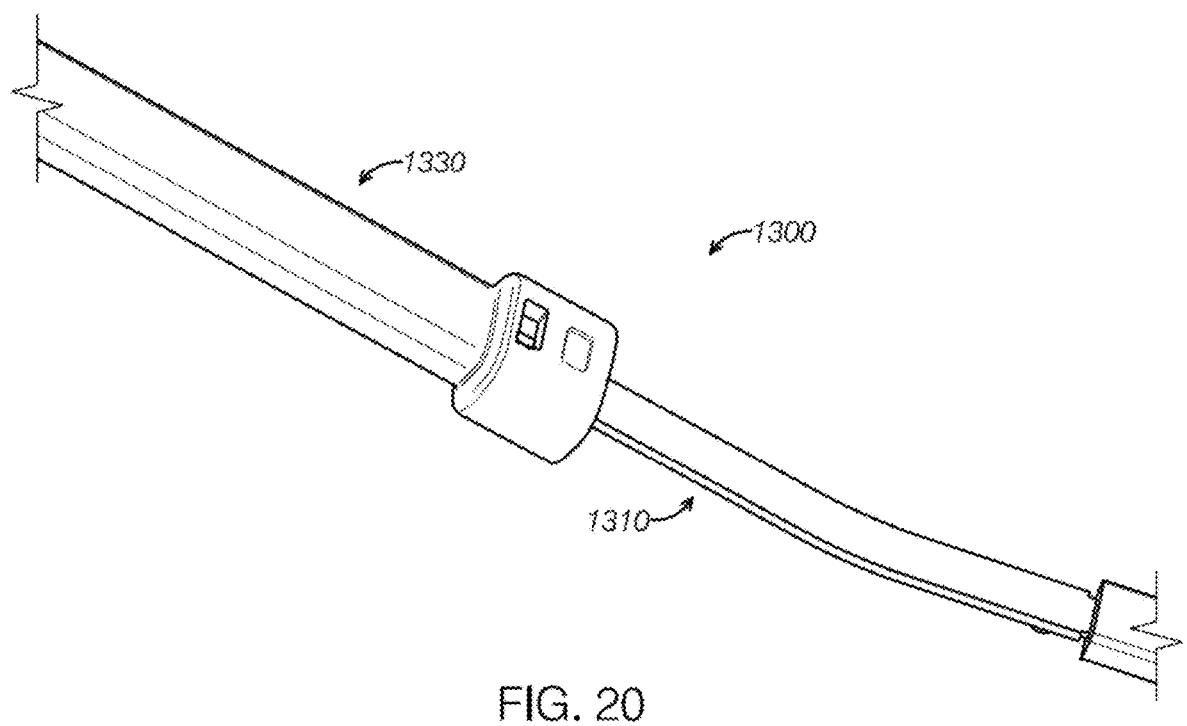
FIG. 20 shows a sample collector proximal end coupled with the distal end of the main body.

In both the designs shown in FIGS. 18A and 18B, handle 1313 can be removed. Removal may also release a locking mechanism that prevents the second actuator/control (shown as slider 1312 in FIG. 15A) from extending the sample collector. Removal may be achieved with minimal force by pulling it in an opposite lateral direction from the body of device 1300. Once handle 1313 has been removed from device 1300, slider 1312, shown disposed longitudinally along device 1300 in FIG. 15A can advance the sample collector 1310 beyond sleeve opening 1307 for processing a second predefined distance that is typically further than the first predefined distance. Thus, the distance that slider 1312 can advance sample collector 1310 may be greater than the distance sample collector 1310 can be extended with handle 1313. This second predetermined distance may allow the sample collector 1310 to be inserted into a sample (e.g., lysis buffer) tube for processing the sample, as described in greater detail below.

Figure 17A:
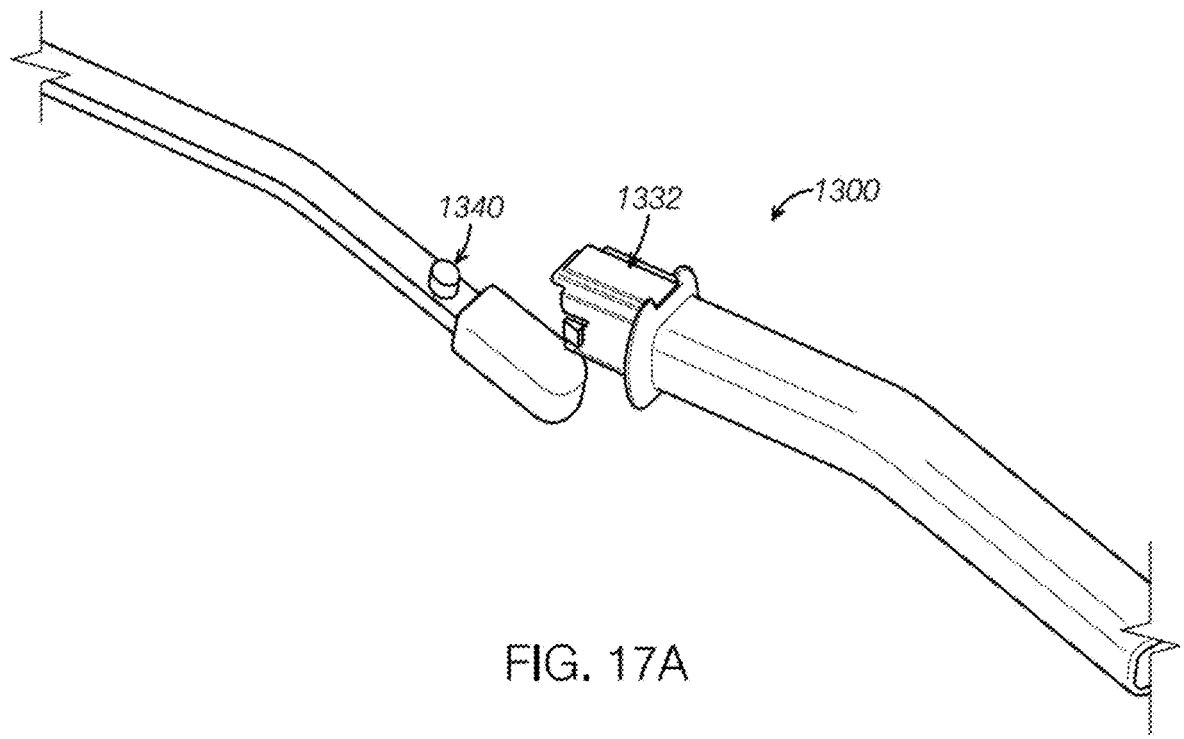
FIG. 17A illustrates one variation of a distal end of a sample collector and a corresponding sleeve into which the sample collector may be housed. Also shown is at least one coupler that joins the sleeve to the main body of the device.
Figure 17B:
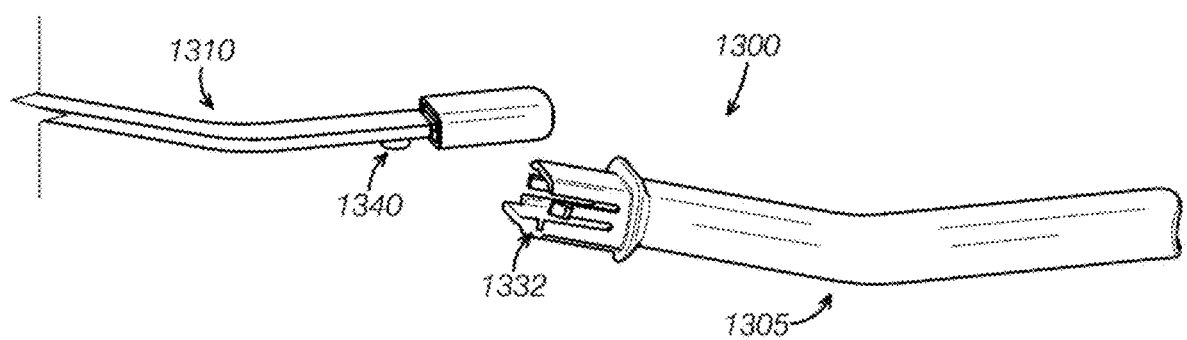
FIG. 17B illustrates an alternative configuration for the at least one coupler that joins the sleeve to the main body of the device.

Any of these devices may also include a centering element 1340 (which may also be referred to a spacer or centering element) between the sample collector and the main body. Spacer 1340 in FIG. 17A is a protrusion on either the sample collector (e.g., near the distal end) or the main body that prevents sample collector 1310 from contacting the inner sides of sleeve 1305 when sample collector 1310 is extended and retracted from sleeve 1305. Preventing sample collector 1310 from contacting the internal sides of sleeve 1315 is especially important when retracting sample collector 1310 because if the sample-containing sample collector 1310 scrapes past the internal sides of sleeve 1305 as it is being retracted, a portion of the sample collected on that surface of sample collector 1310 will be lost, thus diminishing the amount of sample (e.g., cells or bacteria) available for processing and detection.

Figure 22:
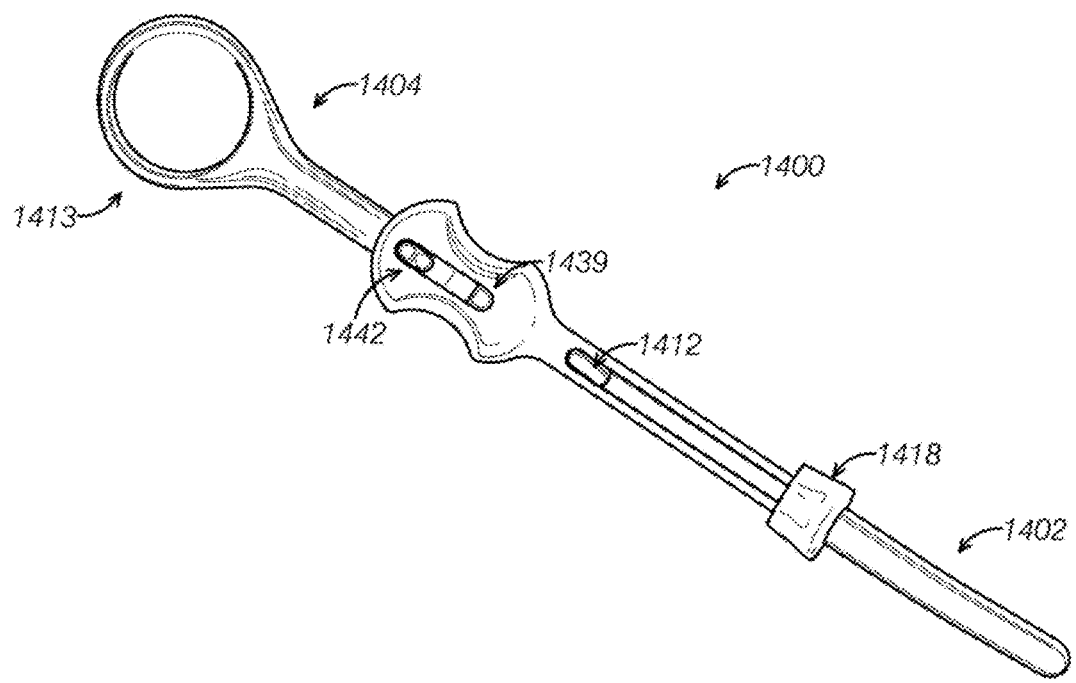
FIG. 22 illustrates another variation of a sampling device having a coupler and releasable hold (e.g. releasable lock, or release lock) on the main body for engaging the distal handle.
Figure 23A:
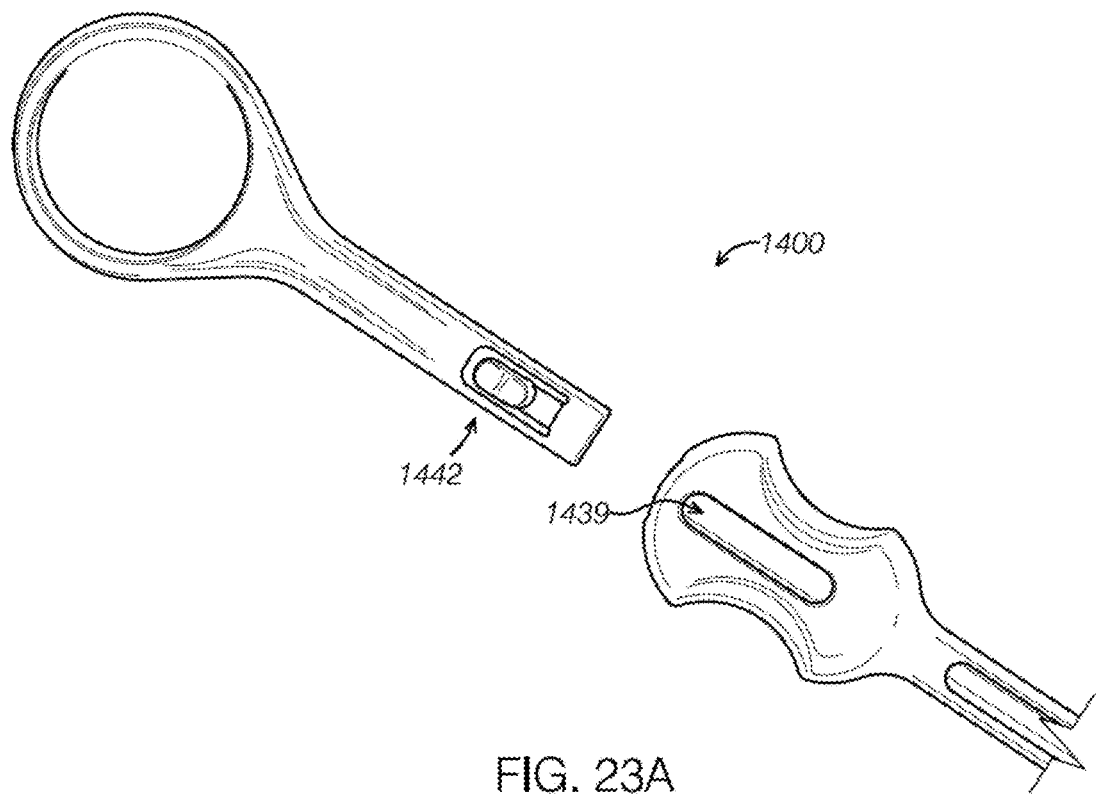
FIG. 23A shows a coupler (shown as a snap-fit coupler) on the handle and a corresponding coupling channel on the main body.
Figure 23B:
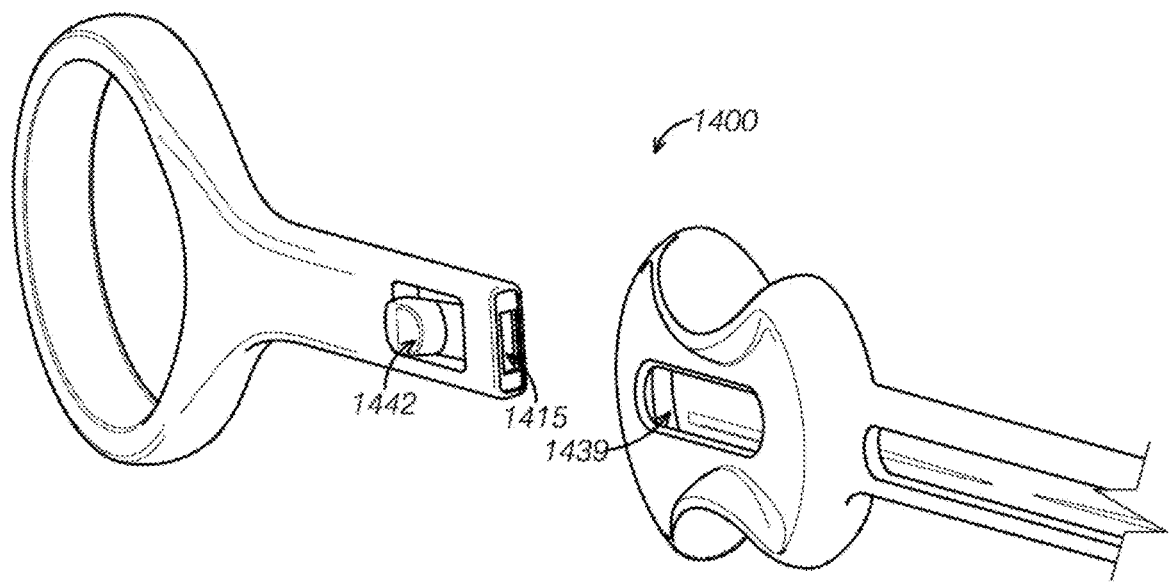
FIG. 23B is an alternative view of the coupler of the handle and a corresponding coupling channel on the main body.
Figure 23C:
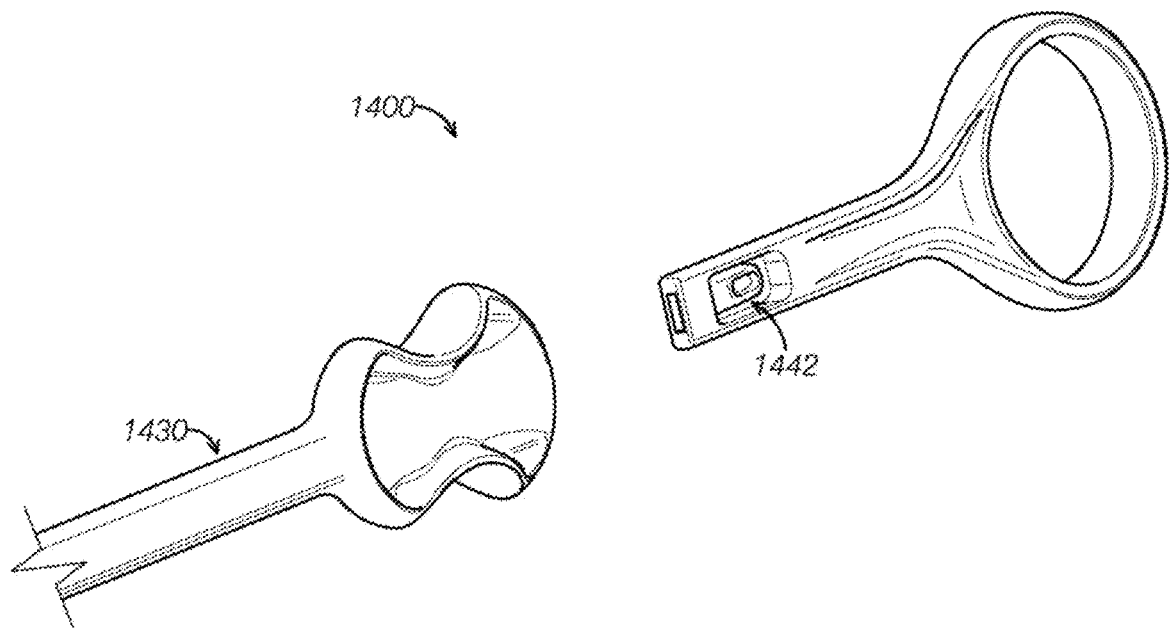
FIG. 23C is another view of a coupler of the handle and a corresponding coupling channel on the main body.

In the variations shown in FIG. 22, hand held sample device 1400 has a distal section 1402 and a proximal section 1404. Hand held device 1400 includes a sample collector 1410 housed within a sleeve 1405 with a sleeve opening 1407, a main body 1430, a (thumb ring) handle 1413 and a depth stop 1418.

Unlike the previously discussed embodiment where the handle is coupled to the sample collector with the main body, and where upon obtaining a sample, the user can disengage the handle by pulling the handle laterally away from the rest of the device, in the variations shown in FIG. 17, the device 1400 may include an additional safety feature to prevent inadvertent uncoupling of handle 1413 from sample collector 1410 and main body 1430. In this variation, main body 1430 includes a channel 1439. Channel 1439 is of a predetermined length with respect to main body 1430. In operation, handle 1413 couples with sample collector 1410 and channel 1439 provides is of a predetermined length that handle 1413 can only slide a given distance within main body 1430 when coupled. The predetermined distance corresponds to the distance sample collector 1410 can extend from sleeve 1405. In any of the device variations described herein, the handle may include a release 1442. Release 1442, when engaged with channel 1439, may allow handle 1413 to extend and retract sample collector 1410 (e.g., the predetermined first length). To release handle 1413, a user presses and slide release element 1442 to allow release element 1442 to disengage from main body 1430 of device 1400. Then, similar to other embodiments, device 1400 includes a slider 1420 that can extend sample collector 1410 a second predetermined distance (that may be greater than the first predetermined distance possible when sample collector 1410 is extended by handle 1413).

Methods of Using Extraction Device

Also disclosed herein are methods of using the devices described above, as well as sinusitis assays using them.

For example, the following steps can be taken to obtain a sample of a patient's infected mucous. When the patient is seated or laying down, place the sampling device (or other embodiment of the device) at approximately forty five degrees with respect to the floor. Insert sleeve of the device (e.g., the distal end) into the subject's nasal passage, ensuring that the angle of sleeve is pointed downward to follow the natural curvature of the nasal passage. Discretion should be used where user experiences resistance when inserting the device into the nasal cavity of the subject. The depth stop on the device may provide a safety measure and prevent the user from inadvertently inserting more of the device into the subject's nasal cavity than is needed or safe.

Next, user pushes the slider forward to expose the swab's distal end to the sinus middle meatus. In other embodiments, the thumb ring is coupled to the swab element. There, the user may use the thumb ring by inserting his thumb through the thumb ring aperture and sliding the thumb ring forward to expose the distal end of the swab for sampling the sinus region. Once a sample has been collected, the user can retract the sample collector distal end using the slider. In other embodiments, the user can retract the distal end of the swab back into the sleeve by pulling the thumb ring proximal end away from the main body. The device then can be removed from the nasal cavity of the subject and the sample collected can be now tested for bacterial presence.

Figure 25A:
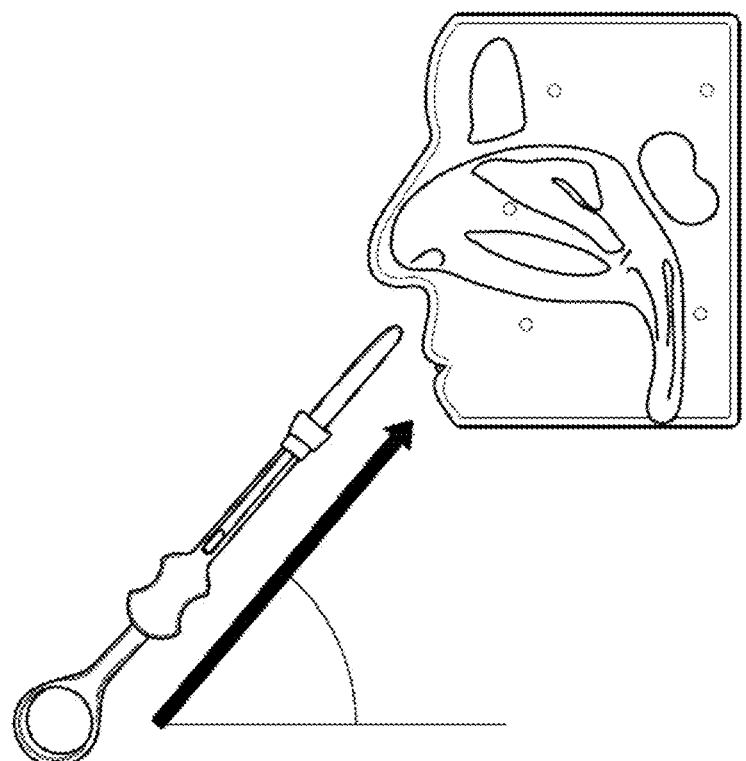
FIGS. 25A-25K illustrate the operation of a sample collector as described herein.
Figure 25B:
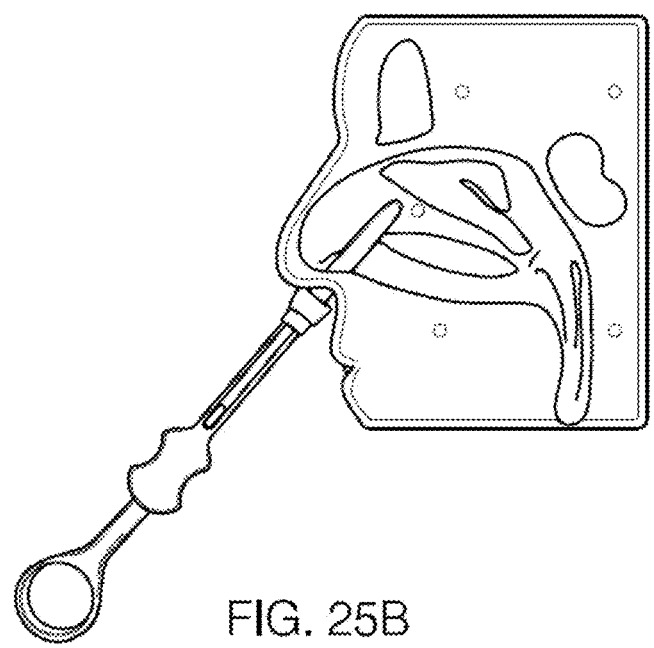
Figure 25C:
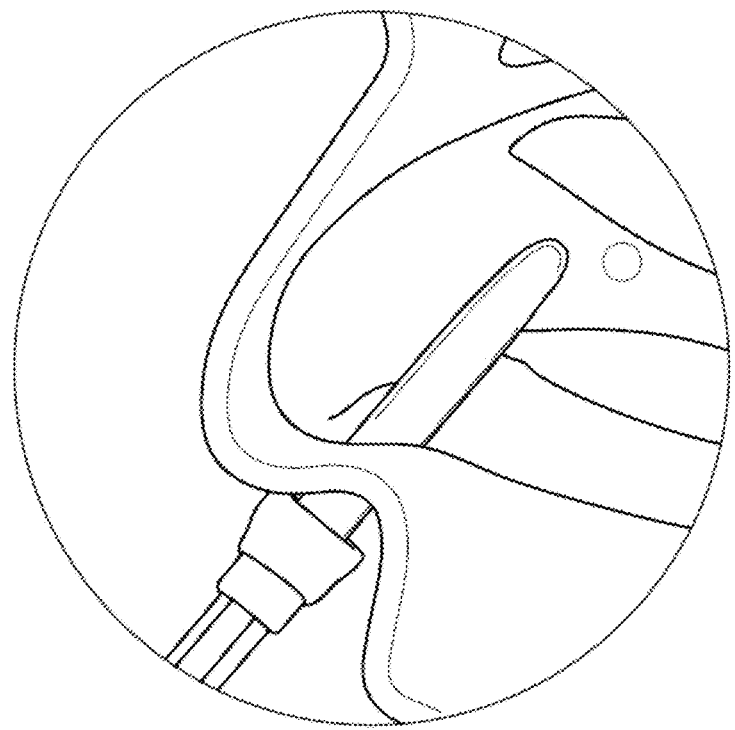

FIGS. 25A-25K illustrate another method of operating the sinus mucosal sample devices described herein. In FIG. 25A, the sinus collection device is inserted into the patient's nose by placing the device (probe) at an approximately 45 degree angle relative to the floor (shown by arrows), with the patient in an upright, sitting position. As shown in FIG. 25B, the collection device is then placed into the sinus by inserting the sinus collection device tip through the nasal cavity and into sinus middle meatus until the depth stop of the device is engaged (e.g., the stop touches nasal entry), or until a slight tissue resistance is felt. FIG. 25C illustrates the collection device properly positioned into the middle meatus region.

Figure 25D:
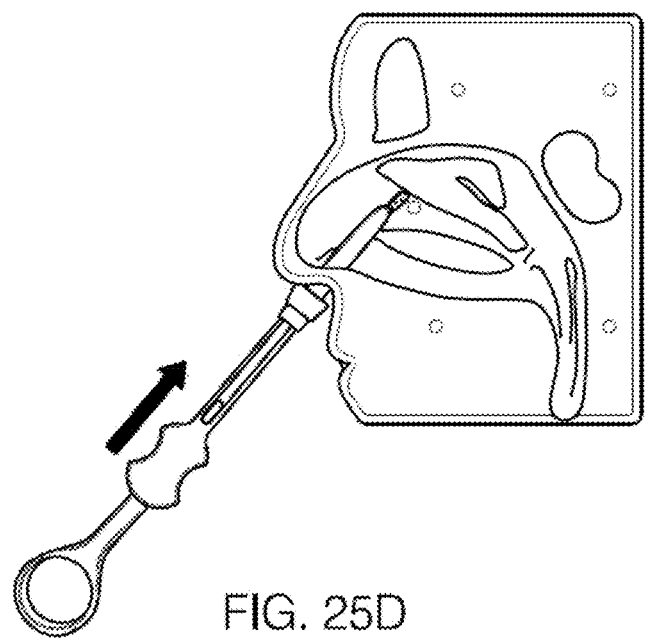
Figure 25E:
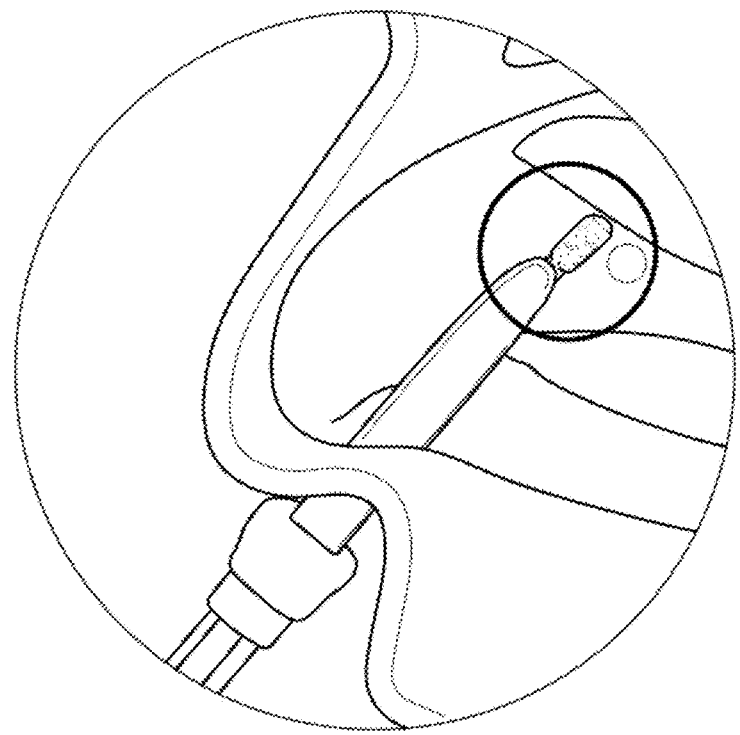
Figure 25F:
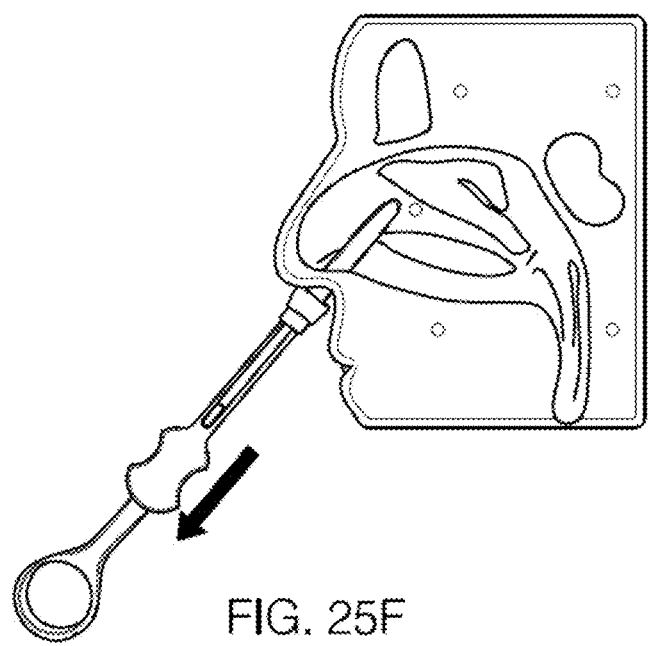
Figure 25G:
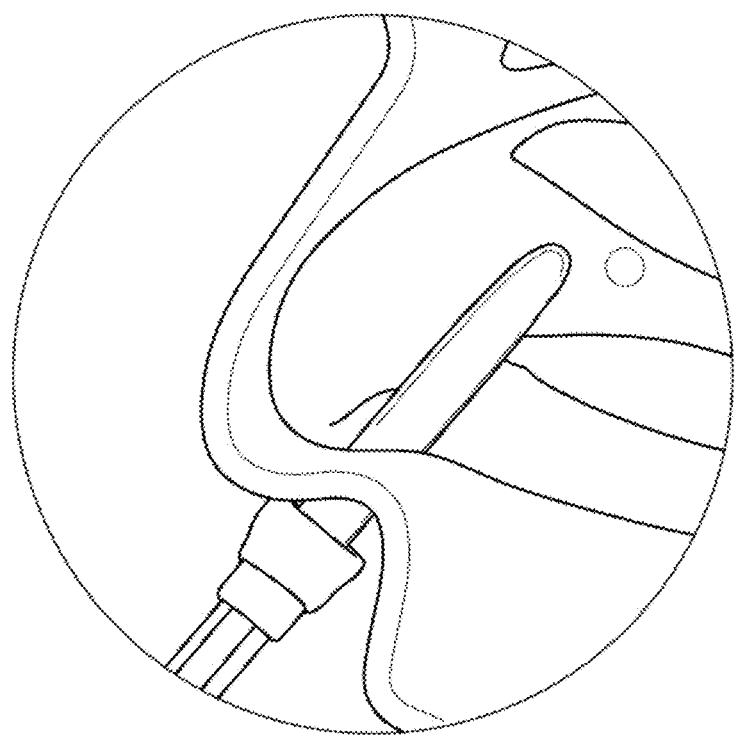
Figure 25H:
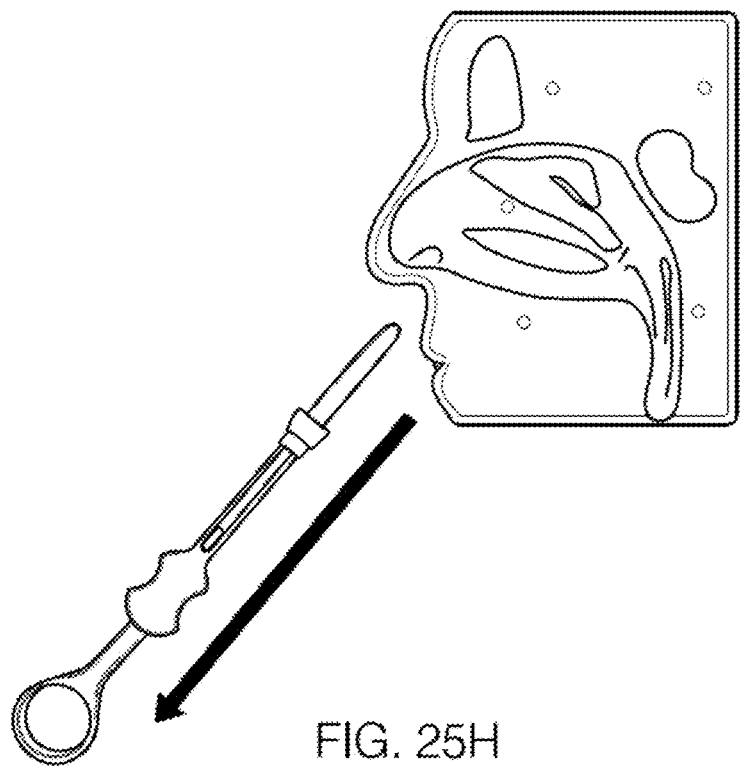

After positioning the collection device, as shown in FIG. 25D, the thumb ring may be pushed to expose the swab tip and collect specimen, by pushing in the direction of the arrow to expose swab tip to sinus fluids. The tip of the swab is extended a first predetermined distance into the proper region of the sinus, as shown in FIG. 25E, showing the swab tip exposed for fluid collection. Thereafter, the swab tip may be retracted into collection device by reversing the thumb motion and retracting the swab tip into collection device, as shown in FIG. 25F. FIG. 25G shows the swab tip fully retracted into Collection device. Thereafter, the collection device may be removed from the nose, as shown in FIG. 25H. The collection device, once removed from nose, is ready for assay testing, which may be performed in a physician's office or other lab area.

Figure 25I:
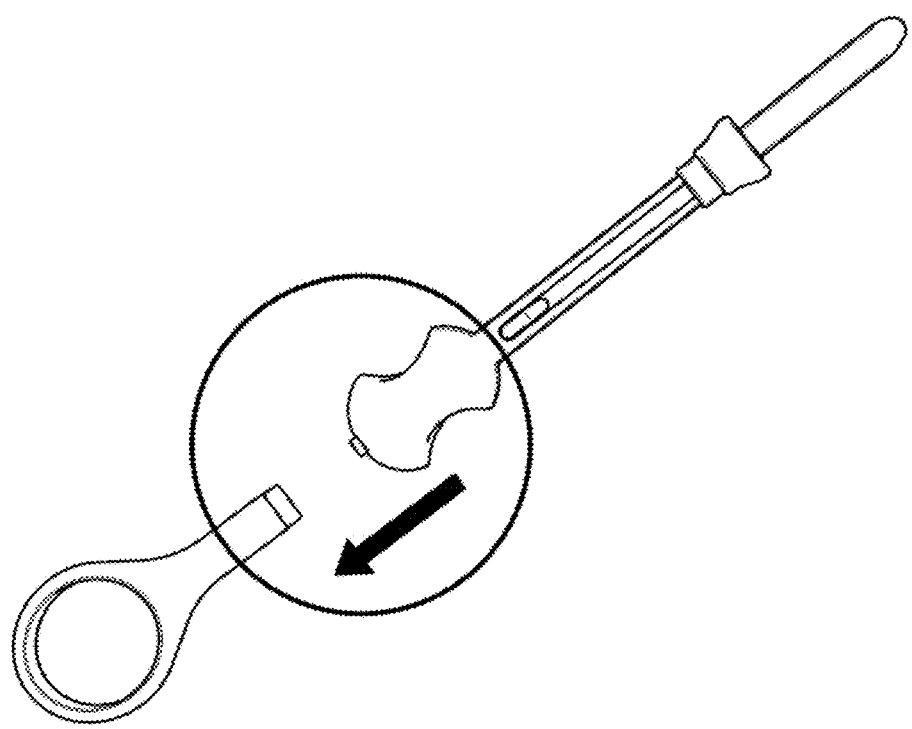
Figure 25J:
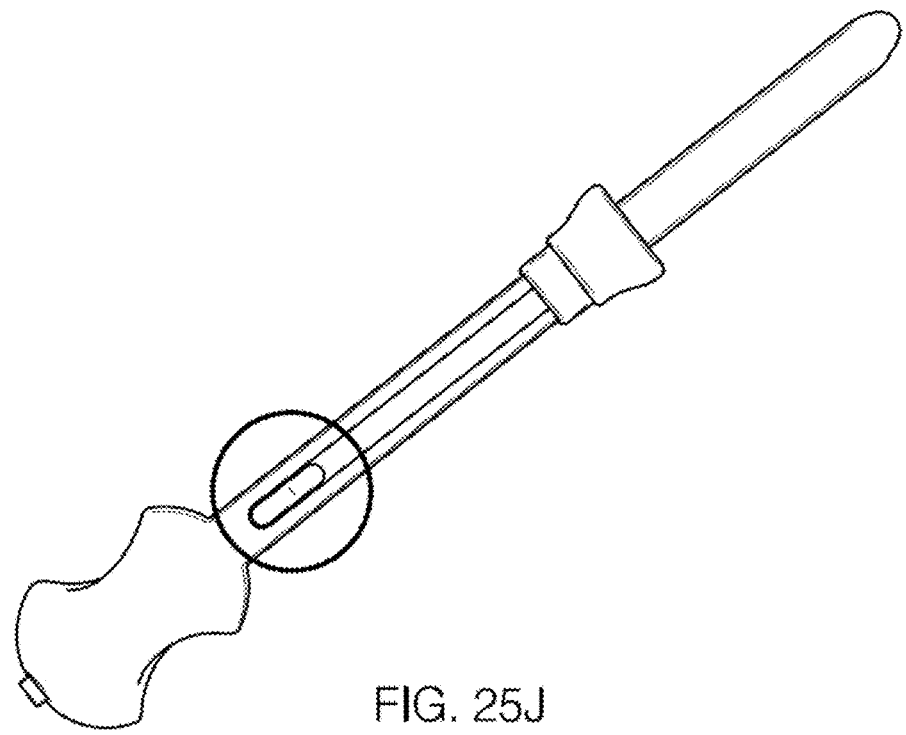
Figure 25K:
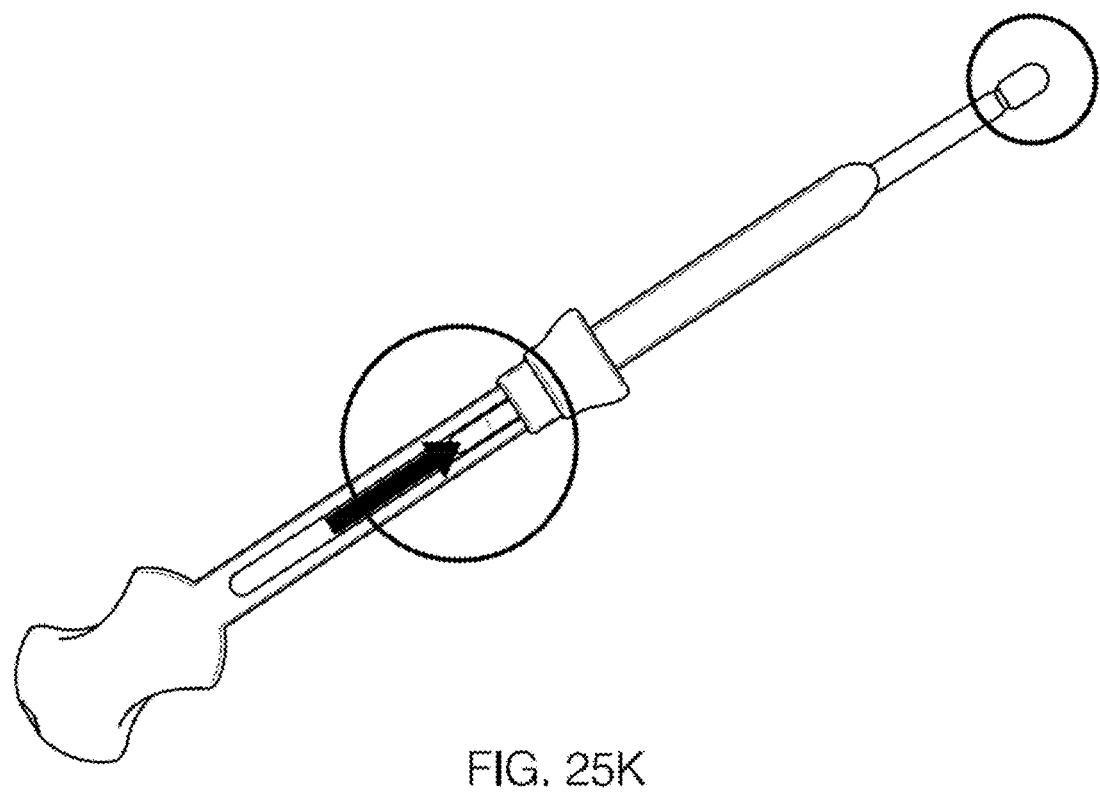

For processing, the distal controller, e.g., the distal handle or thumb loop, may be removed, as shown in FIG. 25i. Removing the handle in any of these devices may release a limiter or lock that prevents the swab from extending distally. The collection device may be fully or partially extended before testing the sample. For example, FIG. 25K shows a device with the swab fully extended for processing; the swab portion (circled) was fully extended by sliding the second (distal) controller distally. Once fully extended, the swab may be processed by inserting into a buffer (e.g., lysing buffer) as described in greater detail below.

Sample Assay

Also described herein are assays that can be used to detect and diagnose bacterial sinusitis. More specifically, the assays may utilize antigen binding agents (e.g., antibodies, antibody fragments, etc.) for detecting markers specific to the types of bacteria contained with the sinus secretions of the subject. The methods disclosed herein may allow detection of signature antigens that are associated with specific bacterial pathogens within the paranasal sinus cavity, and may thus allow a caregiver better insight as to whether prescribing an antibiotic is beneficial. The assays may also provide information that aids a caregiver in deciding which antibiotic regimen would provide the most favorable outcome and most importantly, reduce the use of broad-spectrum antibodies in cases where such treatment would not effective.

These assays may utilize biomarkers that are specific antigens indicating the presence of the organism or pathological process of interest. "Biomarkers" are naturally occurring molecule, gene, or characteristic by which a particular pathological or physiological process, disease, or the like can be identified or characterized. The term "biomarker" may refer to a protein measured in sample whose concentration reflects the severity or presence of some disease state. Biomarkers may be measured to identify risk for, diagnosis of or progression of a pathological or physiological process, disease or the like. Exemplary biomarkers include proteins, hormones, prohormones, lipids, carbohydrates, DNA, RNA and combinations thereof. Although the examples of assays described herein are specific to antigen binding agents such as antibodies in a sandwich-type lateral flow assays, other assays, including nucleotide hybridization, enzymatic and ligand-receptor type assays may also or alternatively be used.

In some variations, the assay is capable of detecting at least one biomarker, and more preferably two biomarkers, including biomarkers from each of a plurality of bacterial types linked to sinusitis. The assays can be further modified to detect greater than two biomarkers (e.g., preferably three). Furthermore, detecting the biomarkers can mean detecting a portion of the proteins, hormones, prohormones, lipids, carbohydrates, DNA, RNA and combinations thereof. The biomarkers may also be a biologically active variant of the naturally occurring molecule of interest. For example, a protein or DNA biomarker can have at least 65%, at least 70%, at least 80%, at least 85%, 86%, 87%, 88%, or 89%, and more typically 90%, 91%, 92%, 93%, 94%, and most common, 95%, 96%, 97%, 98% or 99% conformity or sequence identity to the native molecule.

Assays and Kits

Any of the assays described herein may be part of a kit that allow a user to easily perform the assays for detecting antigens that are the primary cause bacterial sinusitis. The kits may include the sampling device that is described above. The kits can also include a means for lysing the cells in order to expose the target antigens of interest, such as a lysis buffer, and a means for delivering the lysed supernatant to the assay portion of the kit.

A first critical step in obtaining accurate results is in properly processing the sample extracted from the sampling device. Proper processing includes formulating an appropriate lysis buffer. While finding a lysis buffer that can lyse one particular type of cell is fairly straightforward, it is much more challenging to prepare a buffer composition that is able to lyse multiple bacterial cells of interest while protecting the bioactivity of the antigens of interest and while lysing in a reasonable amount of time (e.g., less than 15 minutes). Most cells can be lysed by mechanical means, such as sonification or freeze/thaw cycles, but such methods may require additional equipment. Thus, in some instances, it is preferable to use milder methods, such as detergents, for disrupting the cell membrane. Detergents may disrupt the lipid layer surrounding cells by solubilizing proteins and interrupting the lipid-lipid, protein-lipid, and/or protein-protein interactions. The appropriate detergent composition also depends upon the type of cells to be lysed, be it animal, bacteria, or yeast.

In the developing the "triple" assay for detecting one or more of *M. catarrhalis, S. pneumoniae*, and *H. influenzae* described herein, various lysis buffers were tested for their ability to lyse all of the bacterial cells of interest, namely *M. catarrhalis, S. pneumoniae*, and *H. influenzae*. For example, while N-Lauroylsarcosine effectively lysed NTHI and exposed antigens for recognition by their antigens, it did not effectively lyse *M. catarrhalis*. Next, TritonX-100, a commonly used lysis buffer was also tested and appeared to lyse *M. catarrhalis*, but did not work well with NTHI (nontypeable *Haemophilus influenzae*) The inventors determined that the addition of sucrose to a lysis buffer containing N-Lauroylsarcosine (e.g., Sarkosyl) was effective in lysing all three bacterial cell lines of interest. Without being limited to a particular theory of operation, the addition of an appropriate percentage of sucrose to the N-Lauroylsarcosine lysis buffer may provide an osmotic shock to the cell membranes of the more lysis-resistant cell membranes to achieve appropriate lysing.

FIG. 27 illustrates various examples of lysis buffers that have been examined, indicating their effectiveness with different types of the bacterial strains of interest. Although many of the buffers identified are effective in lysing one of the types of bacteria, in FIG. 27, only the 7% sucrose with 1.3% Sarkosyl was effective (and efficient) in lysing all three of *M. catarrhalis, S. pneumoniae*, and *H. influenzae*. For example, 0.1% Triton X-100 with lysozyme effectively/efficiently lysed *M. catarrhalis* but not *S. pneumoniae* or *H. influenzae*, while 1% Sarkosyl effectively/efficiently lysed *H. influenzae* but not *S. pneumoniae*, and *M. catarrhalis*. None of B-PER reagent, 0.1% Triton X-100 without lysozyme, RIPA buffer, 0.1% Tween 20, 0.1% IGEPAL, 0.1% Tergitol or 0.1% Brij 35 was sufficiently effective in lysing any of *M. catarrhalis, S. pneumoniae*, and *H. influenzae*. Thus, it was surprising that only the combination of sucrose with Sodium lauroyl sarcosinate, (e.g., 7% sucrose with 1.3% Sarkosyl) was able to lyse all three types of bacterial cells at near-comparable levels. Although only 7% sucrose with 1.3% Sarkosyl, other combinations of sucrose (e.g., between 3% and 15% sucrose, and between 0.5% and 3% Sarkosyl, etc.) may be effective. Thus, the combination of osmotic and anionic detergent disrupting cell wall appears to be most effective.

Thus, in one variation, a lysis buffer appropriate for use with all of *Haemophilus influenzae, Moraxella catarrhalis* and *Streptococcus pneumoniae* includes between 5-15% sucrose (e.g., 7% sucrose), EDTA, PMSF, 1.3% sarkosyl (Sodium lauroyl sarcosinate), 50 mM Tris at a pH of 8.0.

The assay may include antigen binding agents (e.g., antibodies, antibody fragments, etc.) that specifically bind the protein biomarker of interest and components for immunoassay to detect the protein biomarkers using associated antibodies. The kits can also contain instructions on carrying out the sampling, performing the assay, and any of the methods associated with this invention.

The present invention provides for methods for detecting at least one biomarker that is specific to a biofilm protein profile for a pathogenic bacteria. In general, immunological methods are well-known in the art, and performed routinely for diagnostic and research purposes. ELISA (enzyme-linked immunosorbent assay) is a powerful tool in studying antibodies and antigens and their concentrations in a sample. ELISA can be used to detect the presence of antigens that are recognized by an antibody or conversely, ELISA can be used to test for antibodies that recognize an antigen. An immunoassay that utilizing the ELISA platform is the two antibody sandwich ELISA.

Sandwich ELISA is used to determine antigen concentration in unknown samples. If a pure antigen standard is available, the assay can determine the absolute amount of antigen in an unknown sample. Sandwich ELISA requires two antibodies that bind to epitopes that do not overlap on the antigen. This can be accomplished with either two monoclonal antibodies that recognize discrete sites or a batch of affinity-purified polyclonal antibodies. A purified first antibody (the capture antibody) is bound to a solid phase. A sample containing the corresponding first antigen is added and allowed to complex with the bound first antibody. Unbound first antigen is washed away and a second antibody with a label (the detecting antibody) is allowed to bind to the first antigen, thus forming a "sandwich". The assay is then either quantitative or qualitative amount of the second/ detecting antibody bound. It is also possible to first bind the antigen to the labeled/detecting antibody and then expose the antigen-labeled antibody complex to the bound antibody.

The present invention allows for greater than one sandwich ELISA assay, in order to concurrently detect one or more of *Haemophilus influenzae, Moraxella catarrhalis* and *Streptococcus pneumoniae*, which together may account for >90% of bacterial sinusitis. In some variations, additional pathogens may also be detected (e.g., *Pseudomonas aeruginosa*). In some embodiments, the assay contains two, three, or more distinct antigen and antibody pairings such that more than one antigen can be detected with one single assay. The results of the presence of at least one or more antigen can be qualitatively obtained, meaning that there is a threshold concentration of the targeted antigen or antigens within the sample. Also, the assay can provide more quantitative measure of the presence of one or more antigens by comparison with a standard or reference. A standard or reference refers to a sample that has a known antigen and biomarker, and in some cases, a known concentration of the known antigen and biomarker or antigens and corresponding biomarkers of interest.

An optical (including, but not limited to visual) indicator may be used to indicate the presence of an antigen. The visual indicator is typically displayed on a region of the assay. The visual indicator can be colorimetric. The visual indicator can also be a symbol, such as a line, that indicates the presence of a particular antigen. The immunoassay may contain labeling next to the regions where different indicators for the presence of various antigens will be shown. Having the labeling will alert the user as to which particular antigen is or antigens are present with the sample. A caregiver user will then have a better knowledge as to which antibiotic, if any, should be provided to the subject.

The immunoassay can be of any suitable format. In some examples, the immunoassay can be performed using a dipstick format where the sample solution is drawn up the "dipstick" type assay with capillary action. The immunoassay can also have a largely horizontal format such as a lateral flow assay. In this latter formats, the sample extracted from the subject's nose is treated such that the cells are lysed in an appropriate buffer, freeing the proteins and providing the sample solution. An aliquot of the sample solution then can be placed in a sample reservoir on the assay or other region noted on the assay and migrated across regions of the assay that contain bound antibodies. Furthermore, the dipstick or flat format immunoassays can have a solid support made of any suitable material, such as nitrocellulose or polyvinylidene difluoride (PVDF) or other membranes, dipstick, wells, or tubes.

Figure 24A:
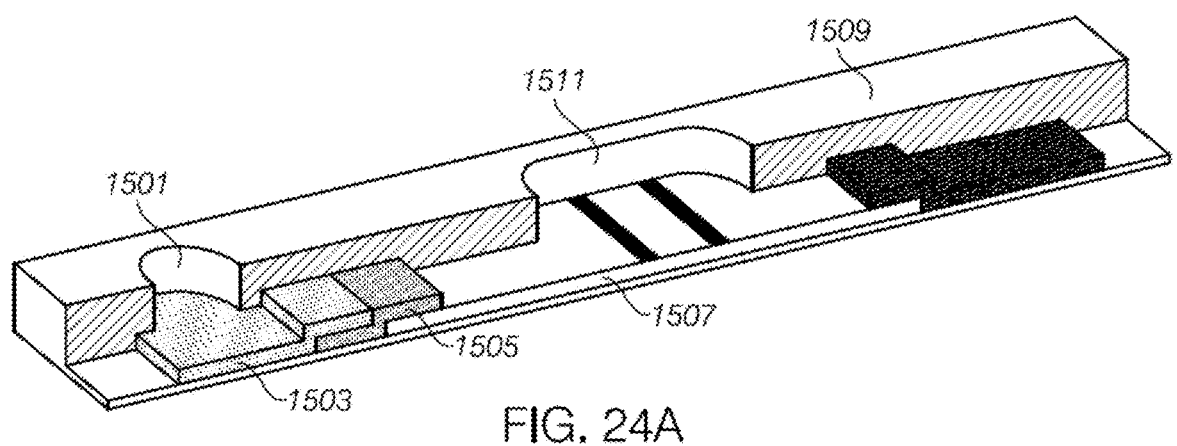
FIGS. 24A-24D show schematics of one example of a lateral flow assay (having two detection readouts, e.g., for two sets of antibodies) and components.
Figure 24B:
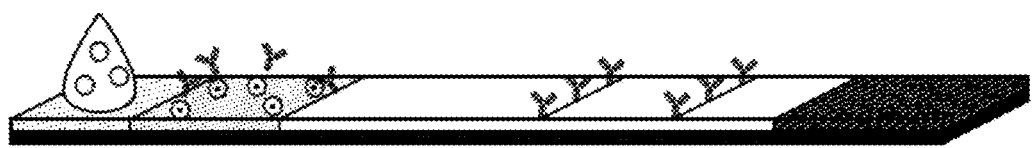
Figure 24C:
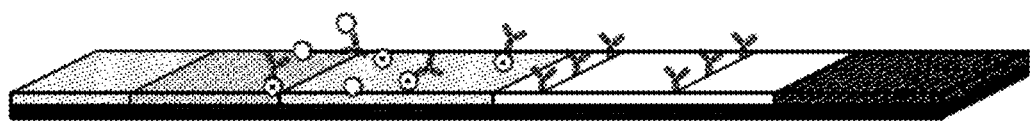
Figure 24D:
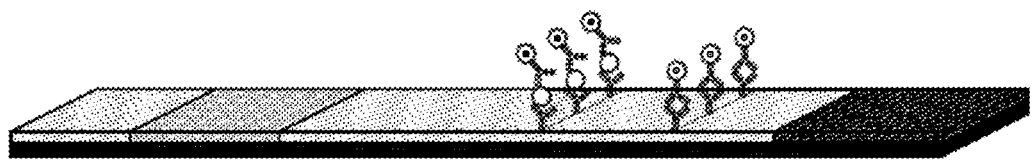

In this present example, a combined immunoassay for three different antigens are described. The three antigens of interest and described below are all associated with bacterial sinusitis, but the overall concept of having a multiple antigen test on one assay can be applied to other antigen/antibody systems as well. An example of a lateral flow assay 1500 is shown in FIGS. 24A-24D. Lateral flow assay 1500 includes a housing 1509 having a sample inlet 1501 (e.g., sample port) for depositing an aliquot of sample and detection window 1511 for visualizing the results of the assay. A sample pad 1503 a conjugate pad 1505, and a detection pad 1507 are included within a housing 1509. Sample pad 1503 will hold the sample to be run through the assay. Sample pad 1503 is in contact with conjugate pad 1505. Conjugate pad 1505 contains the first antigen binding agent (e.g., shown here as an antibody) specific for at least one antigen. In some examples, the conjugate pad may contain two distinct antigen binding agent (e.g., antibodies) that recognize and bind to two distinct antigens. In other examples, the conjugate pad may contain three distinct antigen binding agents that recognize and bind three distinct antigens. When a sample is run through sample pad 1503 past conjugate pad 1505, any antigen or antigens of interest will bind to corresponding antibodies. The antibodies contained in conjugate pad 1505 may be linked to a detector molecule. The complex or complexes of antigen with detector-labeled antigen binding agent is then delivered across detection pad 1507 where a second antigen binding agent (e.g., antibody or antibodies) corresponding to the one more antigens are immobilized on a solid support. In this example, distinct antibodies are affixed in strips across detection pad 1507 as shown in FIGS. 24B and 24C. Thus, when the corresponding antigen complexed with detector-labeled antibody is eluted past the different regions of detection pad 1507, the antigen complexed with detector-labeled antibody will bind to the corresponding second immobilized antibody and produce a signal as shown in FIGS. 24C and 24D. In any variation described herein, the pattern of the immobilized antigen binding agent may be any appropriate pattern and/or density. For example, one (or preferably all) of the bound antigen binding agent may be arranged on the solid phase substrate into a character, symbol, letter, word, pictogram, etc. In some variations the antigen binding agent is arranged into a letter (e.g., spelling the initial or type of bacteria (e.g., *H. flu, M. cat, S. pneumo*, etc.).

For example, an antigen profile for NTHI may include outer membrane proteins (OMP), specifically, OMP P5 and OMP P2. It has been verified that presence of OMP P5 and OMP P2 within NTHI biofilm supernatant and thus detection of OMP P5 and OMP P2 with a sample is indicative of NTHI infection. Corresponding antibodies were developed to both OMP P5 and OMP P2. For *M. catarrhalis*, antibodies to Protein C and Protein D outer member proteins (OMP-CD) may be used. For *S. pneumoniae*, the PsaA (pneumoccal surface adhesion A) protein may be a viable antigen to indicate the presence of *S. pneumoniae*. PsaA is a surface-exposed common 37-kilodalton multi-functional lipoprotein detected on all known serotypes of *Streptococcus pneumoniae*.

FIGS. 31 and 32 illustrate example of other types of cartridge configurations that may be useful. For example FIG. 31 illustrates schematically how three different assays for different bacteria may be combined into a single assay, using a single lysis buffer for all three types of bacteria. In this example, the cartridge 3100 includes a single port 3103. The cartridge also includes a window 3109 into an inner region of the cartridge, showing the solid phase substrate on which the assay is being run.

FIG. 32 is another variation of cartridge in which each assay is run in parallel and the report out includes three separate windows and/or three separate solid phase substrates. Both of the examples shown in FIGS. 31 and 32 include a control band that is formed as a positive control that the labeled antigen binding agent has diffused through the device. As mentioned above, any of these device may include a vent or opening at the end opposite to the cartridge.

Example 1 (Lysis Buffer)

As shown in FIG. 27, different lysis buffers were tested to determine the best buffer composition for successfully lysing the cells corresponding to *Haemophilus influenzae* (*H. flu*), *Moraxella catarrhalis* (*M. cat*) and *Streptococcus pneumoniae* (*S. pneumo*). Some of the potential candidates tested included N-Lauroylsarcosine, Triton X100, Sarkosyl, Sarkosyl and sucrose, and Bugbuster (Novogen). Standardized samples with known concentrations of *Haemophilus influenzae, Moraxella catarrhalis* and *Streptococcus pneumoniae* were used to test the effectiveness of each of these buffers. Based on the lysing data, the sucrose and Sarkosyl lysis buffer composition appeared to be the most effective in being able to lyse all three cell types. Importantly, many combinations (including combinations not including sarkosyl and sucrose) did not work for all three cell types and therefore may not be compatible with a combined assay for detection of all three cell types.

Thus, in general, only lysis buffers having an osmotic agent (e.g., sucrose) and an anionic surfactant (sarkosyl, sodium lauroyl sarcosinate, which may be referred to as an ionic surfactant, anionic detergent or ionic detergent) was compatible with the assays for all three of *M. cat, S. pneumo*, and *H. flu*. In particular, lysis buffers having an osmotic agent between 0.1% and 15% (w/w or w/v, e.g., between 0.5% and 12%, 0.5% and 10%, etc.) and an anionic surfactant between 0.01% and 5% (w/w or w/v, e.g., 0.05% and 5%, 0.1% and 5%, 0.05% and 3%, etc.) were effective, whereas other lysis buffers having non-ionic detergents/surfactants, enzymatic agents, or either osmotic agents alone or anionic/ionic surfactants alone were not effective. For example the lysis buffer may include an osmotic agent within a range having a lower value of 0.1%, 0.2%, 0.3%, 0.5%, 0.6%, 0.7%, 0.8%, 0.9%, 1%, 1.1%, 1.2%, 1.3%, 1.4%, 1.5%, 1.6%, 1.7%, and an upper value of 1.3%, 1.5%, 1.7%, 2%, 2.5%, 3%, 4%, 5%, 7.5%, 10%, 12%, 15%, 20%, etc., where the lower value is less than the upper value, and an anionic detergent within a range having a lower value of 0.05%, 0.1%, 0.15%, 0.2%, 0.25%, 0.3%, 0.35%, 0.4%, 0.45%, 0.5%, etc., and an upper value of 1.3%, 1.4%, 1.5%, 1.6%, 1.7%, 1.8%, 1.9%, 2%, 2.1%, 2.2%, 2.3%, 2.4%, 2.5%, 3%, 4%, 5%, 7.5%, 10%, 12.5%, 15%, 17.5%, 20%, etc., where the lower value is less than the upper value. Examples of anionic surfactants (e.g., detergents) include alkylbenzenesulfonates, sulfates, sulfonates, and phosphate esters, including in particular sarkosyl (sodium lauroyl sarcosinate). Surprisingly, only lysis buffers containing the combination of an osmotic agent and an anionic surfactant within the specified ranges were compatible for use in the assay looking for epitopes specific to each of the three cell types (*M. cat, S. pneumo, H. flu*).

FIG. 28 illustrates two exemplary lysis buffer that may be used (and were used to generate exemplary readings in a lateral flow assays, such as the ones shown in FIGS. 30A-30C, and may be used as part of the assay (e.g., kits, systems, etc.) described herein. FIG. 29 illustrates two exemplary dilution buffers used as part of the assay (e.g., kits, systems, etc.) described herein.

Example 2 (Swabbing Material Selection)

Experiments testing the optimal sampling swab material was also performed. Because the region where the sample is to be collected, a subject's nasal and sinus cavity, is a fairly sensitive area, it is important to be able to quickly and effectively gather enough sample material for assaying. Also, it would be desirable only sample the subject's nasal and sinus cavities once because repeated sampling can cause irritation to the subject's nose and sinus cavities. In addition, any attempts to gather sample after a first try may elicit an autonomic response of excess mucous in the nasal passage that may dilute the sample collected or blood. While materials as cotton swabs and gauze can be used, two commercially available swab materials were tested for their ability to quickly take up sample. Hydraflock, Ultraflock, and Purflock were tested for their ability to take up water, ATS-M (artificial test soil) lab soil containing mucin, and bacteria in ATS lab soil in a given time interval. In addition to the uptake analysis, materials were also analyzed for their ability to release sample. Hydraflock showed 100% recovery and release at 10 and 30 seconds. In contrast materials such as Purflock showed only 85% recovery and release.

Thus, in general, the sample collector (swab or swab material) may be a flocked material that is coupled to a shaft (e.g., an extendable and/or slideable shaft, rod, member, etc.). Flocked materials may minimize entrapment of the cells, while efficiently absorbing them for later release. In particular, flocked swabs having split (e.g., bifurcated, or multiply-split) distal ends of the fibers, such as the hydroflock material described above work surprisingly well, even compared to other flocked materials.

Example 3: Assay

Figure 26:
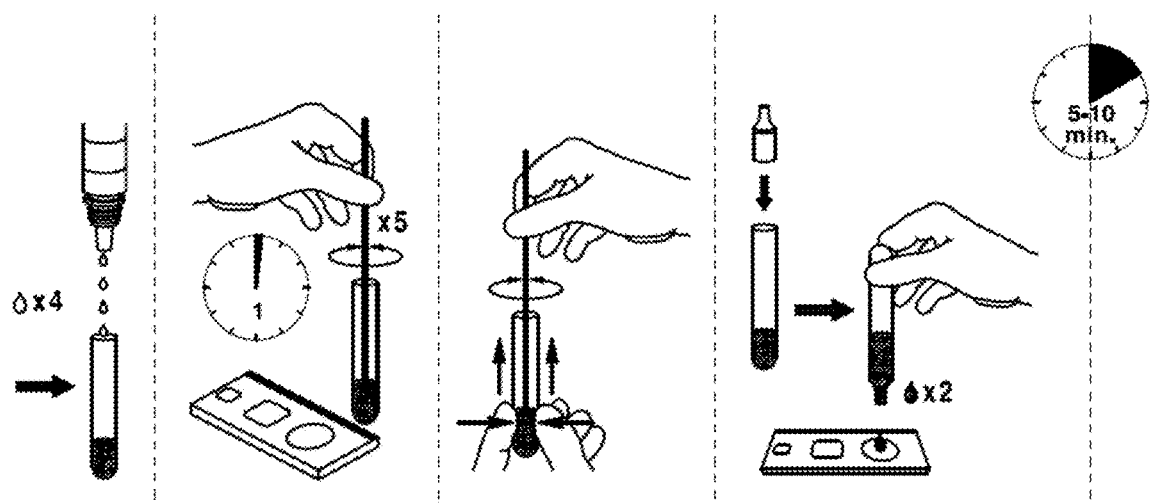
FIG. 26 schematically illustrates one variation of an assay similar to the assay shown in FIGS. 24A-24D for diagnosing sinusitis.

Following sampling with a device as described above for the collection device, the swab with the sample is inserted into the lysis buffer by fully extending the swab tip and inserting into an appropriate volume of lysis buffer, as shown in FIG. 26. In this example, the swab positive end goes into a tube with the lysis buffer (the swab may be the swab of a sample device, such as shown in FIG. 25K). The swab may be mixed or agitated in the buffer, and removed (e.g., after between 1-30 sec). The bacteria may be lysed within the sample buffer by the action of the lysing buffer. See FIGS. 28 and 29 for examples of lysing buffer (FIG. 28) and dilution buffer (FIG. 29). The sample buffer may then be directly applied to the assay or it may be diluted (e.g., 1:10) in the lysis buffer or a second buffer (a dilution buffer, e.g., a Tris buffer), which may aid in wicking on the membrane. 100-200 microliters of sample may then be loaded into the port on a lateral flow cartridge, possibly followed by loading an additional volume (e.g., 100-200 microliters) of buffer to induce wicking (as a "chaser"). An assay configured similar to that shown in FIGS. 24A-24D and described above may be used (e.g., a lateral flow assay) in which there are three separate regions arranged in sequence (adjacent each other) followed by a control region. This configuration is one variation of a multiplexed arrangement. Alternatively or additional one or more of the bound antibody-containing regions (sensing/detection regions) may be present in a parallel region that is fed by the same or a different port. In these examples the antigen binding agents are antibodies, including a pair of antibodies is directed to each antigen specific to one of the bacterial types; a tethered (e.g., in the detection region) antibody (e.g., antigen binding agent) and a soluble (detection) antibody (antigen binding agent) which may be linked to a visible marker (readout) such as colloidal gold or a visible dye (e.g., colored latex bead). In some variations the assay may be read in about 5 minutes (e.g., following 2-3 min of lysis or less and 3-5 min on the cartridge or cassette). The time to a positive or negative result (as shown by the positive control, which may be cross-reactive to the detection antibody, e.g., tethered antimouse antibody within a downstream control region), may depend on the wicking of the sample in the membrane. Typically after adding the sample to the assay device ("cartridge" or "cassette"), the sample wicks through a sample pad into a conjugate pad, then into the membrane, where the markers may be captured by capture antibody, concentrating antibody also bound to the marker (antigen) and having a readout (e.g., colloidal gold) so that it can be visualized.

As mentioned, the capture antibodies may be laid down on the membrane in different characteristic positions (e.g., marked/labeled), and may depend on the wicking capacity of the membrane.

FIGS. 30A-30C illustrate proof-of-concept data showing sensitivity ranges for assays as described herein for detection of each of S. pneumo, M. cat, and H. flu, respectively.

In FIG. 30A, an assay using a first antigen binding agent that is labeled and that binds to OMP-P2 and/or OMP-P5 and a fourth tethered antigen binding agent that binds specifically to another region of the same antigen (e.g., OMP-P2 and/or OMP-P5) were used. The first and fourth antigen binding agents specific to H. influenzae but not M. catarrhalis or S. pneumoniae. In this example, a lateral-flow assay was prepared with these antigen binding agents, a mucosal sample (which may be taken using a sampling device such as the ones shown in FIGS. 15A-23C and the steps of FIGS. 25A-25K). To generate the curve shown, the sample used may be from a cultured example of the bacteria, so that the concentration may be determined accurately. The sample was re-suspended a lysis buffer such as the buffer shown in FIG. 28 (e.g., lysis Buffer #1), so that all three types of bacteria being sampled (e.g., H. flu, M. cat, and S. pneumo) were lysed appropriate following approximately 30 sec to 1 min of lysis. The solution was then diluted and applied to the sample port 3201 of a lateral flow cartridge such as the one shown in FIG. 32, so that it may be fluidically channeled a conjugation region (e.g., chamber or bad) containing the labeled and untethered first antigen binding agent. In this example, the antigen binding agent is a monoclonal antibody conjugated to a particle (e.g., colloidal gold or dyed bead) that can be visualized through the window of the cartridge after travelling (e.g., via capillary action) from the conjugation region onto and/or across the portion of the solid phase structure to which the fourth antigen binding agent is tethered. As illustrated in FIG. 30A, different concentrations of sample bacteria (H. flu) were used to generate the sensitivity curve. In FIGS. 30A-30C, the detection was performed manually and visually, however higher sensitivity may be achieved by using a reader (e.g., optical reader) as mentioned above.

In this example, as described above, a single lysis buffer was used for lysing the sample so that multiple (e.g., M. cat, H. flu and S. pneumo) bacterial types could be simultaneously tested for from the same sample, even after a very brief lysis (e.g., between 5 seconds and 15 minutes, between 5 seconds and 10 minutes, between 5 seconds and 5 minutes, between 5 seconds and 4 minutes, between 5 seconds and 3 minutes, between 5 seconds and 2 minutes, between 5 seconds and 1 minute, between 5 seconds and 45 seconds, etc., or less than 15 minutes, less than 10 minutes, less than 5 minutes, less than 1 minute, etc.). The particular composition (and combination) of lysing agents described herein are surprisingly effective at quickly, completely and gently lying the multiple different types/classes of bacteria without disrupting the antigens or their ability to be recognized by the antigen binding agents used.

In FIG. 30B, M. cat was detected in parallel (e.g., by loading a sample of the lysed solution into the second port 3207 of the cartridge shown in FIG. 32, and S. pneumo was detected by loading the solution into the third port 3209 in FIG. 32. Alternatively concurrent detection may be performed using a cartridge 3100 such as the one shown in FIG. 31. With respect to detection of Moraxella catarrhalis (M. cat) a pair of antigen binding agents (second and fifth antigen binding agents or just agents) that are specific to the antigen Protein C (an outer member protein) at different portion of the antigen were used; the second antigen biding agent is labeled as described above (e.g., using colloidal gold), and the fifth antigen binding agent is tethered to a specific region of the solid phase substrate (e.g., a membrane within the cartridge). Similarly detection of Streptococcus pneumoniae (S. pneumo) in FIG. 30C may be performed using the lateral flow cartridge such as the one shown in FIG. 32 (applying the sample into the port 3209). The antigen in this example is a PsaA antigen that is recognized by both the third and sixth antigen binding agents, where the third agent is labeled and the sixth is tethered. Thus, the second agent binds specifically to a second antigen specific to M. catarrhalis but not H. influenzae or S. pneumoniae. Similarly, the third and sixth agents bind specifically to the third antigen specific to S. pneumoniae but not M. catarrhalis or H. influenzae.

In FIGS. 30A-30C, the sensitivities for detection of cells (expressed as colony forming units (CFU)/sample) show thresholds for visual detection between $10^3$-$10^5$ per 100 µl sample. As mentioned above, this sensitivity may be increased, for example by using a reader to read the cartridge.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A nasal sampling device for obtaining a sinus secretion sample from a subject's sinus, wherein the nasal sampling device includes:
an elongate body having a distal end region that is bent relative to a proximal region by between 15 degrees and 30 degrees;
a sample collector on a distal end of an extendable shaft, wherein the sample collector is configured to collect a sample of sinus fluid, further wherein the sample collector is housed entirely within the distal end of the elongate body in a retracted position; and
a control coupled to the extendable shaft, the control having a first set point wherein the sample collector is extended distally out of a distal opening of the distal end region of the elongate body a first distance between 0.5 cm to 3 cm, the control having a second set point, wherein the sample collector is retracted and housed entirely within the distal end of the elongate body, the control having a third set point, wherein the sample collector is extended distally out of the distal opening of the distal end region of the elongate body a second distance that is greater than the first distance.

2. The nasal sampling device of claim 1, further comprising a spacer on the extendable shaft proximal to the sample collector, wherein the spacer is configured to prevent the sample collector from contacting an inner surface of the elongate body when the sample collector is retracted into the distal end of the elongate body.

3. The nasal sampling device of claim 1, wherein the control comprises a releasable stop configured to prevent the control from selecting the third set point until the stop is released.

4. The nasal sampling device of claim 3, wherein the stop comprises a detachable handle configured to releasably couple to the distal end of the extendable shaft.

5. The nasal sampling device of claim 4, wherein the stop comprises a releasable connector connecting the extendable shaft to the stop.

6. The nasal sampling device of claim 1, wherein the second distance is 1.0 cm or greater than the first distance.

7. The nasal sampling device of claim 1, wherein the sample collector comprises a swab.

8. The nasal sampling device of claim 1, wherein the control is coupled to a handle at the proximal end of the device.

9. The nasal sampling device of claim 1, further comprising a handle body extending proximally from the elongate body, wherein the extendable shaft extends through the elongate body and into an internal channel within the handle body.

10. The nasal sampling device of claim 1, wherein the distal end region of the elongate body is between 1.5 and 3.5 cm long.

11. The nasal sampling device of claim 1, wherein the proximal region of the elongate body is greater than 1 cm long.

12. The nasal sampling device of claim 1, wherein the extendable shaft comprises a flexible elongate shaft.

13. The nasal sampling device of claim 1, wherein the extendable shaft is configured to slide within the elongate body.

14. The nasal sampling device of claim 1, wherein the control comprises a slider.

15. The nasal sampling device of claim 1, wherein the control comprises a finger ring.

16. The nasal sampling device of claim 1, wherein the control comprises a compression actuator configured to be compressed to select the third set point in which the sample collector is extended distally out of the distal opening of the distal end region of the elongate body the second distance.

17. The nasal sampling device of claim 1, wherein the control is configured to be distally advanced to select the first set point in which the sample collector is extended distally out of the distal opening of the distal end region of the elongate body the first distance.

18. The nasal sampling device of claim 1, wherein the control comprises a push button configured to be depressed to select the third set point in which the sample collector is extended distally out of the distal opening of the distal end region of the elongate body the second distance.

19. The nasal sampling device of claim 1, further comprising a lock configured to lock the control at one or more of: the first set point, the second set point or the third set point.

20. The nasal sampling device of claim 1, further comprising a depth gauge configured to display a position of the sample collector to a user of the device.

21. The nasal sampling device of claim 1, wherein the distal end region is configured to have an open configuration when the sample collector is advanced out of the distal end region of the elongate body, and a closed configuration when the sample collector is in the retracted position.

22. The nasal sampling device of claim 1, further comprising a depth stop.

* * * * *